United States Patent
Bungard et al.

(10) Patent No.: US 8,119,681 B2
(45) Date of Patent: Feb. 21, 2012

(54) 2-[1-PHENYL-5-HYDROXY OR METHOXY-4ALPHA-METHYL-HEXAHYDROCYCLOPENTA[ƒ]INDAZOLE-5-YL]ETHYL PHENYL DERIVATIVES AS GLUCOCORTICOID RECEPTOR LIGANDS

(75) Inventors: Christopher J. Bungard, Lansdale, PA (US); Jesse J. Manikowski, Perkiomenville, PA (US); James J. Perkins, Churchville, PA (US); Robert Meissner, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 323 days.

(21) Appl. No.: 12/445,901

(22) PCT Filed: Oct. 23, 2007

(86) PCT No.: PCT/US2007/022463
§ 371 (c)(1),
(2), (4) Date: Apr. 16, 2009

(87) PCT Pub. No.: WO2008/051532
PCT Pub. Date: May 2, 2008

(65) Prior Publication Data
US 2010/0311709 A1 Dec. 9, 2010

Related U.S. Application Data

(60) Provisional application No. 60/853,655, filed on Oct. 23, 2006, provisional application No. 60/923,337, filed on Apr. 13, 2007.

(51) Int. Cl.
*A61K 31/415* (2006.01)
*C07D 231/54* (2006.01)

(52) U.S. Cl. .................. 514/406; 548/359.1

(58) Field of Classification Search .............. 514/406; 548/359.1
See application file for complete search history.

(56) References Cited

U.S. PATENT DOCUMENTS

| 6,846,839 B1 * | 1/2005 | Tang et al. ............ 514/397 |
| 7,411,073 B2 * | 8/2008 | Ali et al. ............. 548/359.1 |

FOREIGN PATENT DOCUMENTS

| WO | WO 03061651 A1 | 7/2003 |
| WO | WO 03086294 A2 | 10/2003 |
| WO | WO 2004075840 A2 | 9/2004 |
| WO | WO 2004093805 A2 | 11/2004 |

* cited by examiner

*Primary Examiner* — Rei-tsang Shiao
(74) *Attorney, Agent, or Firm* — Yong Zhao; Valerie J. Camara

(57) ABSTRACT

The present invention is directed to 2-[1-phenyl-5-hydroxy or methoxy-4alpha-methyl-hexahydrocyclopenta[f]indazol-5-yl]ethyl phenyl derivatives of formula I (I) as glucocorticoid receptor ligands useful for treating a variety of autoimmune and inflammatory diseases or conditions. Pharmaceutical compositions and methods of use are also included.

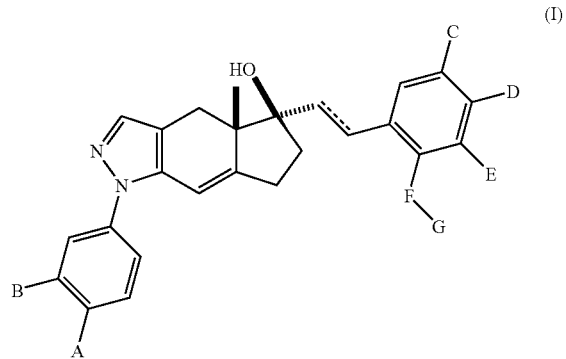

17 Claims, No Drawings

2-[1-PHENYL-5-HYDROXY OR METHOXY-4ALPHA-METHYL-HEXAHYDROCYCLOPENTA [f]INDAZOLE-5-YL]ETHYL PHENYL DERIVATIVES AS GLUCOCORTICOID RECEPTOR LIGANDS

CROSS REFERENCE TO RELATED APPLICATIONS

This application is a U.S. National Phase application under 35 U.S.C. §371 of PCT Application No. PCT/US2007/022463, filed Oct. 23, 2007 which claims priority under 35 U.S.C. §119(e) from U.S. Provisional Application Ser. No. 60/853,655, filed Oct. 23, 2006 and U.S. Provisional Application Ser. No. 60/923,337, filed Apr. 13, 2007.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor has an essential role in regulating human physiology and immune response. Steroids that interact with the glucocorticoid receptor have been shown to be potent anti-inflammatory agents, although cross-reactivity with other steroid hormone receptors such as the mineralocorticoid, progesterone and androgen receptors can lead to problematic ancillary pharmacology.

The dissociation of transactivation from transrepression at the glucocorticoid receptor is believed to be an approach toward improving the side-effect profile related to steroid therapy. The beneficial anti-inflammatory activity of GR modulators, such as steroids, is believed to occur through the transrepression of genes encoding for proinflammatory cytokines, adhesion molecules and enzymes. Many of the undesirable side-effects associated with such agents are believed to occur through the transactivation, or induction, of gene transcription leading to the downstream perturbation of homeostatic endocrine function. Some of these affected metabolic processes include induced gluconeogenesis, induced amino acid degradation, osteoporosis, suppression of HPA axis, induction of secondary adrenal suppression, changes in electrolyte concentration, changes in lipid metabolism, growth retardation, impaired wound healing and skin thinning. Weak, partial and full agonism of GR related to transrepression and transactivation, including potential antagonism of the receptor regarding transactivation, may be applied to the treatment of inflammatory and autoimmune diseases such as rheumatoid arthritis and asthma. For recent reviews see: (a) *Recent Advances in Glucocorticoid Receptor Action*; Cato, A. C. B., Schacke, H., Asadullah, K., Eds.; Springer-Verlag: Berlin-Heidelberg, Germany, 2002. (b) Coghlan, M. J.; Elmore, S. W.; Kym, P. R.; Kort, M. E. In *Annual Reports in Medicinal Chemistry*; Doherty, A. M., Hagmann, W. K., Eds.; Academic Press: San Diego, Calif., USA, 2002; Vol. 37, Ch. 17, pp 167-176.

Glucocorticoid receptor modulators are described in WO 2003/061651, WO2003/086294, WO2004/026248, WO2004/075840 and WO2004093805. An object of the invention is the discovery of novel compounds that modulate the glucocorticoid receptor. Another object of the invention is the discovery of novel glucocorticoid receptor modulators with superior transactivation and transrepression activity profiles. It is believed that such compounds would have potent anti-inflammatory and immunosuppressive activity and possess advantages over current steroid therapies with respect to side effects, efficacy, toxicity and/or metabolism.

SUMMARY OF THE INVENTION

The present invention is directed to 2-[1-phenyl-5-hydroxy or methoxy-4alpha-methyl-hexahydrocyclopenta[f]indazol-5-yl]ethyl phenyl derivatives as glucocorticoid receptor ligands useful for treating a variety of autoimmune and inflammatory diseases or conditions. Pharmaceutical compositions and methods of use are also included.

DETAILED DESCRIPTION OF THE INVENTION

The invention encompasses a genus of compounds of Formula I

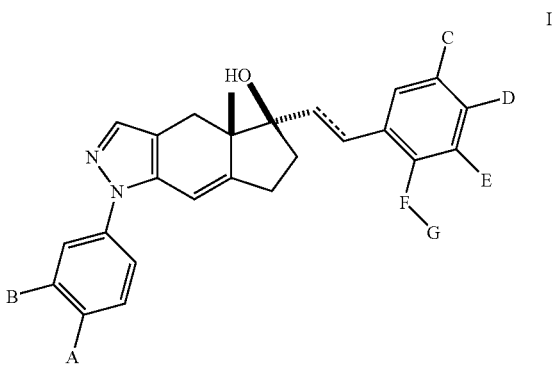

or a pharmaceutically acceptable salt thereof, wherein
------ is an optional double bond;
A and B are independently selected from the group consisting of: H and F;
C, D and E are independently selected from the group consisting of: H, F, —CH$_3$ and —CF$_3$;
F is selected from the group consisting of: a bond, —C(R$^1$)(R$^2$)— and —C(R$^1$)(R$^2$)—C(R$^3$)(R$^4$)—;
G is selected from the group consisting of: —CN, —OH, —O—C(O)—N(R)(R), —O—C(O)—O—R, —C(O)—R, —C(O)—O—R, —NRR, aryl, substituted aryl, heteroaryl, substituted heteroaryl, —C(R$^a$)(R$^b$)—N(R)(R), —C(O)—N(R)(R), —C(O)—N(R)—C(R$^a$)(R$^b$)—R, —C(O)—N(R)—C(R$^a$)(R$^b$)—C(O)—OR, —C(O)—N(R)—C(R$^a$)(R$^b$)—C(O)—NRR, —N(R)—C(O)—R, —N(R)—C(O)—OR, —N(R)—C(O)—N(R)(R), —N(R)—S(O)$_n$—X, —S(O)$_n$—N(R)(R), —N(R)—S(O)$_n$—N(R)(R) and —S(O)$_n$—X, wherein n is 0, 1 or 2;
each R is independently selected from the group consisting of: H, C$_{1-8}$alkyl, haloC$_{1-8}$alkyl, C$_{2-8}$alkenyl, haloC$_{2-8}$alkenyl, C$_{1-8}$alkoxy and C$_{3-6}$cycloalkyl-C$_{1-4}$alkyl-, and
two R groups attached to the same nitrogen atom can be joined together with the nitrogen atom to which they are attached to form a 3- to 7-membered monocyclic ring, said ring optionally substituted with oxo and said ring further optionally substituted with 1 to 3 substituents independently selected from the group consisting of: halo, hydroxyl, C$_{1-4}$alkyl and C$_{1-4}$alkoxy;
X is selected from the group consisting of: H, C$_{1-8}$alkyl, haloC$_{1-8}$alkyl, C$_{2-8}$alkenyl, haloC$_{2-8}$alkenyl, C$_{1-8}$alkoxy, $C_{3-6}$cycloalkyl, $C_{3-6}$cycloalkyl-$C_{1-4}$alkyl-, —CH2-S(O)$_k$—CH$_3$, wherein k is 0, 1 or 2, aryl, substituted aryl, heteroaryl and substituted heteroaryl;

$R^1$, $R^2$, $R^3$ and $R^4$ are independently selected from the group consisting of: H, $C_{1-4}$alkyl, $C_{1-4}$haloalkyl and hydroxy, and $R^1$ and $R^2$ may be joined together with the carbon atom to which they are attached to form a 3- to 6-membered mono-cyclic ring;

$R^a$ and $R^b$ are independently selected from the group consisting of: H, $C_{1-4}$alkyl, $C_{1-4}$haloalkyl and hydroxy or $R^a$ and $R^b$ may be joined together with the carbon atom to which they are attached to form a 3- to 6-membered mono-cyclic ring; and substituted aryl and substituted heteroaryl mean aryl and heteroaryl respectively, each substituted with one to three substituents independently selected from the group consisting of: halo, $C_{1-4}$alkyl, $C_{1-4}$haloalkyl and —CN.

Within the genus, the invention encompasses a first sub-genus of compounds of Formula I wherein F is a bond and the optional double bond is not present.

Within the first sub-genus, the invention encompasses a class of compounds of Formula I wherein G is selected from the group consisting of: —C(O)—N(R)(R), —C(O)—N(R)—C($R^a$)($R^b$)—R, —C(O)—N(R)—C($R^a$)($R^b$)—C(O)—OR and —C(O)—N(R)—C($R^a$)($R^b$)—C(O)—NRR.

Also within the first sub-genus, the invention encompasses a class of compounds of Formula I wherein G is —S(O)$_n$—N(R)(R).

Also within the genus, the invention encompasses a second sub-genus of compounds of Formula I wherein F is —C($R^1$)($R^2$)— and the optional double bond is not present.

Within the second sub-genus, the invention encompasses a class of compounds of Formula I wherein $R^1$ and $R^2$ are H.

Within the class of the second sub-genus, the invention encompasses a sub-class of compounds of Formula I wherein G is —N(R)—S(O)$_n$—X.

Also within the class of the second sub-genus, the invention encompasses a sub-class of compounds of Formula I wherein G is OH.

Also within the class of the second sub-genus, the invention encompasses a sub-class of compounds of Formula I wherein G is —C(O)—N(R)(R).

Also within the genus, the invention encompasses a third sub-genus of compounds of Formula I wherein A is F.

The invention also encompasses a compound selected from Examples 1 to 164 described below or a pharmaceutically acceptable salt of any of these compounds.

Another embodiment of the invention encompasses a pharmaceutical composition comprising a compound of Formula I in combination with a pharmaceutically acceptable carrier.

Another embodiment of the invention encompasses a method for treating a glucocorticoid receptor mediated disease or condition in a mammalian patient in need of such treatment comprising administering the patient a compound of Formula I in an amount that is effective for treating the glucocorticoid receptor mediated disease or condition.

Within this embodiment is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyarthritis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another embodiment of the invention encompasses a method of selectively modulating the activation, repression, agonism and antagonism effects of the glucocorticoid receptor in a mammal comprising administering to the mammal a compound of Formula I in an amount that is effective to modulate the glucocorticoid receptor.

Exemplifying the invention are the compounds of the Examples disclosed hereunder.

DEFINITIONS

The invention is described using the following definitions unless otherwise indicated.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Haloalkyl" means alkyl as defined above wherein one or more of the hydrogen atoms are replaced with a halo atom, up to the maximum number of substitutable positions.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Haloalkenyl" means alkenyl as defined above wherein one or more of the hydrogen atoms are replaced with a halo atom, up to the maximum number of substitutable positions.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic saturated carbocyclic rings having the indicated number of carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, adamantanyl and the like.

"Aryl" means mono- or bicyclic aromatic rings containing only carbon atoms and aryl groups fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means mono- or bicyclic aromatic rings containing at least one heteroatom selected from N, O and S, with each ring containing 5 to 6 atoms, and heteroaryl groups fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen and monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halo" means F, Cl, Br and I.

Abbreviations

The following abbreviations have the indicated meanings:
AIBN=2.2'-azobisisobutyronitrile
B.P.=benzoyl peroxide
Bn=benzyl
$CCl_4$=carbon tetrachloride
D=—$O(CH_2)_3O$—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—$CH_2SCH_2CH_2Ph$
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Optical Isomers-Diastereomers-Geometric Isomers-Tautomers Compounds of Formulas I or J contain one or more asymmetric centers and can thus occur as racemates and racemic mixtures, single enantiomers, diastereomeric mixtures and individual diastereomers. The present invention is meant to comprehend all such isomeric forms of the compounds of Formulas I or J.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formulas I or J.

Compounds of the Formulas I or J may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formulas I or J may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Dose Ranges

It will be understood that, as used herein, references to the compounds of Formulas I or J are meant to also include the pharmaceutically acceptable salts.

The magnitude of prophylactic or therapeutic dose of a compound of Formulas I or J will, of course, vary with the nature and the severity of the condition to be treated and with the particular compound of Formulas I and J and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of glucocorticoid receptor mediated diseases the compound of Formulas I and J may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formulas I and J may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formulas I and J are employed. (For purposes of this application, topical application shall include mouth washes and gargles.) Topical formulations may generally be comprised of a pharmaceutical carrier, cosolvent, emulsifier, penetration enhancer, preservative system, and emollient.

For compounds of the invention with poor solubility, the following formulation technologies may be adopted: conventional solid with a surfactant/polymer, solid dispersion (spray dried or hot melt extrusion), liquid filled capsules or nanomilled formulation. Such technologies are known in the art.

Utilities

The ability of the compounds of Formulas I and J to modulate glucocorticoid receptors makes them useful for treating, preventing or reversing the progression of a variety of inflammatory and autoimmune diseases and conditions. Thus, the compounds of the present invention are useful to treat, prevent or ameliorate the following diseases or conditions: inflammation, tissue rejection, auto-immunity, various malignancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, hypertension, cardiac arrhythmias, obesity and metabolic syndrome.

The compounds of the present invention are also useful for treating, preventing or reversing the progression of disease states involving systemic inflammation such as inflammatory bowel disease, systemic lupus erythematosus, polyarthritis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, stress and urge related urinary incontinence, age related sarcopenia, ulcerative colitis, autoimmune chronic active hepatitis, rejection of transplanted organ, prevention of organ transplant rejection, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, neoplasm, HPA axis dysregulation in psychiatric disease, schizophrenia, bipolar disorder, psychotic major depression, posttraumatic syndrome, The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IIL-I expression, natural killer cell development, lymphocytic leukemia, and treatment of retinitis pigmentosa. Cognitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, prevention of cluster headache, schizophrenia, stroke, sleep disorders, and anxiety.

The compounds of the invention are also useful for treating sarcoidosis, disease with enlarged lymph tissue, spleen and liver, follicular b-cell lymphoma, chronic malignant t-cell lymphoma of the skin, a group of lymphomas of the skin, non-hodgkin's lymphoma, diffuse large b-cell lymphoma, type of leukemia—acute lymphocytic leukemia, type of leukemia—chronic lymphocytic, leukemia, increased calcium in the blood from cancer, thyroid gland inflammation, condition caused by excess secretion of male hormones, addison's disease, asthma, worsening of asthma decreased function of the adrenal gland, inflammation of the joints due to gout, disease in which body has immune response against itself, destruction of red blood cells by body's own antibodies, infiltration of white blood cells into the lungs, crohn's disease, inflammatory bowel disease a hereditary progressive anemia of unknown cause, anemia from too few young red blood cells, low platelet count and bleeding of unknown cause, decreased platelets due to a disease state or a drug, multiple sclerosis, inflammation of the heart with rheumatic fever, inflammation of the nose due to an allergy, vocal cord swelling, beryllium poisoning, nephrotic syndrome, atopic dermatitis, contact dermatitis, chronic inflammatory skin disease marked by blisters, blistering skin diseases, erythema multiforme, skin rash with sloughing, psoriasis associated with arthritis, psoriasis, skin condition, systemic lupus erythematosus, diffuse proliferative lupus nephritis—a kidney disease, inflammation of skin and muscles all over the body, rheumatoid arthritis, joint inflammatory disease in children and young adults, rheumatic disease causing pain & stiffness in backbone, inflammation of the elbow and surrounding tissue, muscle or bone disorder, giant hives, allergic reaction caused by a drug, body's rejection of a transplanted organ, prevention of transplant rejection, allergic reaction causing serum sickness, disease causing arthritis & urethral & eyelid inflammation, increased calcium in the blood from sarcoidosis, breast cancer that has spread to another part of the body, multiple myeloma, pure red cell aplasia associated with chronic lymphocytic leukemia, a tumor formed of blood vessels, breast cancer, cancer of the prostate gland, joint disease which may include attacks of acute arthritis, brief muscle spasms in an infant, cluster headache prevention, paralysis of one side of the face, myasthenia gravis, rheumatic fever, inflammation of the covering of the heart or pericardium, inflammation of the heart, periarteritis nodosa, inflammation of the artery in the temple area, vasculitis, presence of polyps in the nose, obstructive pulmonary disease, canker sore, failure of small intestines to digest and absorb food, group of skin disorders that resemble blisters, muscle pain and stiffness in shoulder, neck and pelvis, inflammation of several cartilages of the body, fever due to cancer, prevention of cardiac transplant rejection, and prevention of lung transplant rejection.

Preferably, the compounds of the invention are useful for treating the diseases or conditions set for the below.

1. Allergic States

Control of severe or incapacitating allergic conditions not responsive to adequate trials of conventional treatment; seasonal or perennial allergic rhinitis; bronchial asthma; contact dermatitis; atopic dermatitis; serum sickness; and drug hypersensitivity reactions.

2. Rheumatic Disorders

As adjunctive therapy for short-term administration during an acute episode or exacerbation of: psoriatic arthritis; rheumatoid arthritis including juvenile rheumatoid arthritis (selected cases may require low-dose maintenance therapy); ankylosing spondylitis; acute and subacute bursitis; acute nonspecific tenosynovitis; acute gouty arthritis; post-traumatic osteoarthritis; synovitis of osteoarthritis; and epicondylitis 3. Dermatologic Diseases Ppemphigus; bullous dermatitis herpetiformis; severe erythema multiforme (Stevens-Johnson syndrome); exfoliative dermatitis; mycosis fungoïdes; severe psoriasis; and severe seborrheic dermatitis.

4. Ophthalmic Diseases

Severe acute and chronic allergic and inflammatory processes involving the eye and its adnexa such as: allergic conjunctivitis; keratitis; allergic corneal marginal ulcers; herpes zoster ophthalmicus; iritis and iridocyclitis; chorioretinitis; anterior segment inflammation; diffuse posterior uveitis and choroiditis; optic neuritis; and sympathetic ophthalmia.

5. Endocrine Disorders

Primary or secondary adrenocortical insufficiency; congenital adrenal hyperplasia; nonsuppurative thyroiditis; and hypercalcemia associated with cancer.

6. Respiratory Diseases

Symptomatic sarcoidosis; Löffler's syndrome not manageable by other means; berylliosis; fulminating or disseminated pulmonary tuberculosis when concurrently accompanied by appropriate antituberculous chemotherapy; and aspiration pneumonitis.

7. Hematologic Disorders

Idiopathic thrombocytopenic purpura in adults; secondary thrombocytopenia in adults; acquired (autoimmune) hemolytic anemia; erythroblastopenia (RBC anemia); and congenital (erythroid) hypoplastic anemia.

8. Neoplastic Diseases

For palliative management of: leukemias and lymphomas in adults; and acute leukemia of childhood.

For the treatment of diverse neoplastic diseases such as brain cancer, bone cancer, basal cell carcinoma, adenocarcinoma, lip cancer, mouth cancer, esophageal cancer, small bowel cancer, stomach cancer, colon cancer, rectal cancer, liver cancer, bladder cancer, pancreas cancer, ovary cancer, cervical cancer, lung cancer, breast cancer, head and neck cancer, skin cancer, prostate cancer, gall bladder cancer, thyroid cancer and renal cell carcinoma.

9. Edematous States

To induce a diuresis or remission of proteinuria in the nephrotic syndrome without uremia, of the idiopathic type or that due to lupus erythematosus. Compounds of Formulas I and J may be used to treat patients with cerebral edema from various causes. It may be used also in the preoperative preparation of patients with increased intracranial pressure secondary to brain tumors, and also for palliation of patients with inoperable or recurrent brain neoplasms, and in the management of cerebral edema associated with neurosurgery. Some patients with cerebral edema due to head injury or pseudotumor cerebri also may benefit from therapy with compounds of Formulas I and J.

10. Gastrointestinal Diseases

During a critical period of the disease in: ulcerative colitis and regional enteritis.

11. Miscellaneous

Tuberculous meningitis with subarachnoid block or impending block when concurrently accompanied by appropriate antituberculous chemotherapy; Trichinosis with neurologic or myocardial involvement; During an exacerbation or as maintenance therapy in selected cases of: Systemic lupus erythematosus and acute rheumatic carditis; in combination with ondansetron for the management of nausea and vomiting associated with cisplatin and non-cisplatin emetogenic chemotherapy.

The compounds of the invention are also useful for treating or preventing hypertension, vascular inflammation, urinary incontinence and multiple sclerosis.

12. CNS Diseases

For the treatment of HPA axis dysregulation in psychiatric disease, schizophrenia, bipolar disorder, psychotic major depression and posttraumatic syndrome.

Combination Therapy

The invention also encompasses a method for treating a glucocorticoid receptor mediated disease comprising concomitantly administering to a patient in need of such treatment a compound of Formulas I or J and one or additional more agents. For treating or preventing asthma or chronic obstructive pulmonary disease, the compounds of Formulas I or J may be combined with one or more agents selected from the group consisting of: □-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formulas I or J may be combined with one or the following: a salicylate, including acetylsalicylic acid, a non-steroidal antiinflammatory drug, including indomethacin, sulindac, mefenamic, meclofenamic, tolfenamic, tolmetin, ketorolac, diclofenac, ibuprofen, naproxen, fenoprofen, ketoprofen, flurbiprofen and oxaprozin, a TNF inhibitor, including etanercept and infliximab, an IL-1 receptor antagonist, a cytotoxic or immunosuppressive drug, including methotrexate, leflunomide, azathioprine and cyclosporine, a gold compound, hydroxychloroquine or sulfasalazine, penicillamine, darbufelone, and a ρ38 kinase inhibitor. The compound of Formulas I or J may also be used in combination with bisphonates such as alendronate, SERMs (selective estrogen receptor modulators) or cathepsin K inhibitors to treat a glucocorticoid mediated disease and simultaneously causes osteopenia or osteoporosis. The compound of Formulas I or J may also be used in combination with bone anabolic agents such as PTH, Androgens, SARMs (selective androgen receptor modulators), to treat a glucocorticoid mediated disease and simultaneously induces bone loss as exhibited by osteopenia or osteoporosis.

The compound of Formulas I or J may also be used in combination with drugs used to treat age-related sarcopenia or cachexia to treat a glucocorticoid mediated diseases and simultaneously inhibit muscle loss, sarcopenia and frailty.

METHODS OF SYNTHESIS AND EXAMPLES

Compounds of the invention can be synthesized by following the following general synthetic scheme.

(i) all operations were carried out at room or ambient temperature, that is, at a temperature in the range 18-25° C., (ii) evaporation of solvent was carried out using a rotary evaporator under reduced pressure (600-4000 pascals: 4.5-30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L

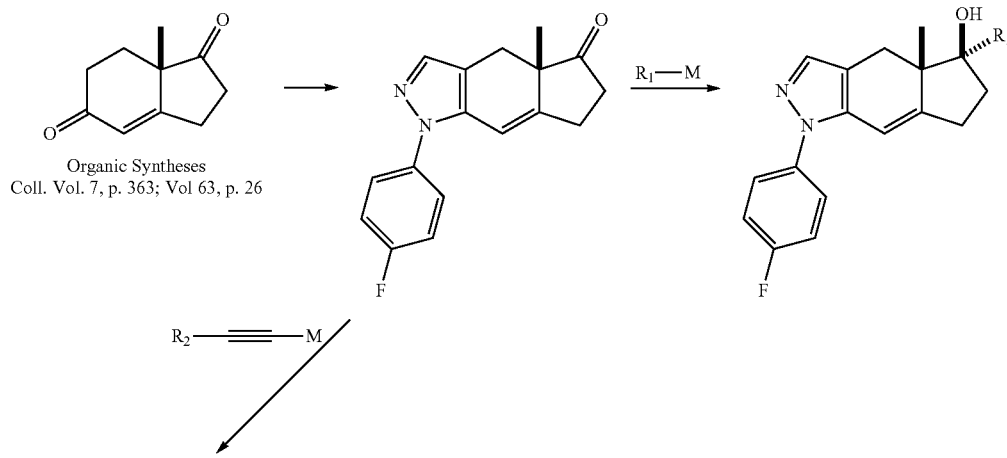

Organic Syntheses
Coll. Vol. 7, p. 363; Vol 63, p. 26

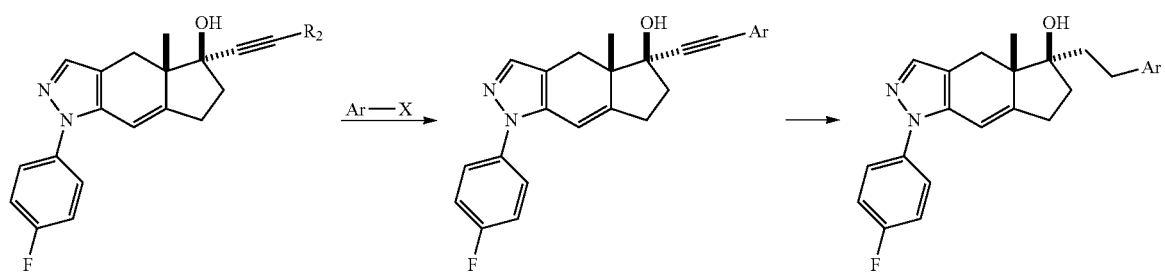

The invention will now be illustrated by the following non-limiting examples in which, unless stated otherwise:

(liter(s)), mL (milliliters), g (gram(s)), mg (milligrams(s)), mol (moles), mmol (millimoles), eq (equivalent(s)).

Example 1

SYNTHESIS of 2-{2-[(4αS,5R)-1-(4-Fluorophenyl)-5-hydroxy-4α-methyl-1,4,4α,5,6,7-hexahydrocyclopenta[f]indazol-5-yl]ethyl}benzoic acid

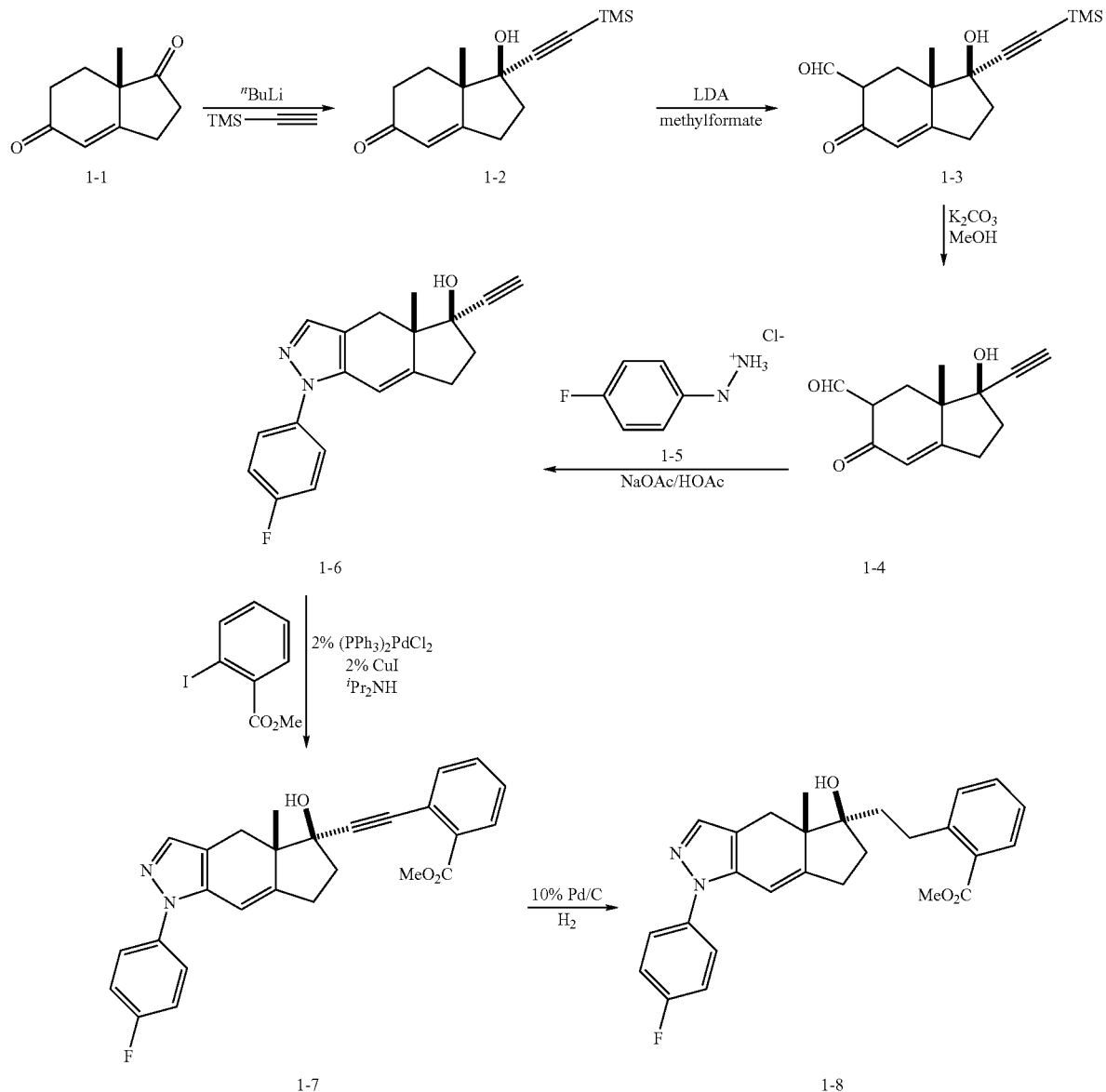

The combined organic extracts were dried over anhydrous MgSO₄ and the solvent removed in vacuo. Purification by flash chromatography on 120 g of silica, eluting with a gradient of 0-55% EtOAc in hexanes afforded 9.54 g, 80% of 1-2 as a white solid.

MS (ESI): m/z=263.25 (MH⁺).

(1S,7αS)-1-Hydroxy-7α-methyl-1-[(trimethylsilyl)ethynyl]-1,2,3,6,7,7α-hexahydro-5H-inden-5-one (1-2)

A 2.5M solution of ⁿBuLi (27.4 mL, 68.5 mmol) in hexanes was added dropwise to a solution of trimethylsilylacetylene (9.48 mL, 68.5 mmol) in THF (90 mL) at −78° C. The resulting solution was stirred at −78° C. for 30 min, then a solution of Hajos-Parrish Ketone (See *Organic Syntheses*, Coll. Vol. 7, p. 363; Vol 63, p. 26) (1-1, 7.5 g g, 45.7 mmol) in THF (90 mL) was added and the resulting solution stirred at −78° C. for 30 min. The reaction was quenched with saturated aqueous KH₂PO₄ and the crude product extracted with EtOAc (×3).

(3S,3αS)-3-Hydroxy-3α-methyl-6-oxo-3-[(trimethylsilyl)ethynyl]-2,3,3α,4,5,6-hexahydro-1H-indene-5-carbaldehyde (1-3)

A 1.5 M solution of lithium diisopropylamide mono(tetrahydrofuran) in cyclohexane (121 mL, 182 mmol) was added to a solution of 1-2 (9.54 g, 36.4 mmol) in THF (400 mL) at −78° C. and the resulting solution stirred at this temperature for 1 hour to afford a thick suspension. Methyl formate (22.6 mL, 364 mmol) was added dropwise over about 15 min and the resulting suspension stirred at −78° C. for 5 hours. The reaction was quenched at −78° C. with 1 M aqueous HCl solution and the aqueous layer checked to ensure it was acidic. The crude product was extracted with EtOAc (×3) and the combined organic extracts were dried over anhydrous MgSO$_4$ and the solvent removed in vacuo to afford crude 1-3 (78% pure) that was used directly in the next step without purification.

MS (ESI): m/z=291.18 (MH$^+$).

(3R,3αS)-3-Ethynyl-3-hydroxy-3α-methyl-6-oxo-2, 3,3α,4,5,6-hexahydro-1H-indene-5-carbaldehyde (1-5)

K$_2$CO$_3$ (5.03 g, 72.8 mmol) was added to a solution of crude 1-4 in MeOH (300 mL) and the resulting suspension stirred at ambient temperature for 90 min. The MeOH was removed in vacuo and 1M aqueous HCl was added to the residue and the crude product extracted with EtOAc (×3). The combined organic extracts were dried over anhydrous MgSO$_4$ and the solvent removed in vacuo. Purification by flash chromatography on 330 g of silica, eluting with a gradient of 0-70% EtOAc in hexanes afforded 5.94 g, 75% of 1-6 as a tan solid.

MS (ESI): m/z=219.25 (MH$^+$).

(4αS,5R)-5-Ethynyl-1-(4-fluorophenyl)-4α-methyl-1,4,4α,5,6,7-hexahydrocyclopenta[f]indazol-5-ol (1-6)

NaOAc (41.3 g, 504 mmol) was added to a solution of 1-5 (100 g, 458 mmol) and 4-fluorophenylhydrazine hydrochloride (1-5) (82 g, 504 mmol) in acetic acid (916 mL) and the resulting suspension stirred at ambient temperature for 1 hour. The reaction was quenched slowly (caution CO$_2$ evolution) with saturated aqueous NaHCO$_3$ solution and the crude product extracted with EtOAc (×3). The combined organic extracts were dried over anhydrous MgSO$_4$ and the solvent removed in vacuo. Purification by flash chromatography on 1.5 Kg of silica, eluting with a gradient of 0-100% EtOAc in hexanes afforded 133 g, 94% of 1-6 as a tan solid.

MS (ESI): m/z=309.2 (MH+).

Methyl 2-{[(4αS,5R)-1-(4-fluorophenyl)-5-hydroxy-4α-methyl-1,4,4α,5,6,7-hexahydrocyclopenta[f]indazol-5-yl]ethynyl}benzoate (1-7)

Diisopropylamine (2.85 mL, 20.0 mmol) was added to a solution of 1-6 (6.16 g, 20.0 mmol), methyl 2-iodobenzoate (6.28 g, 24.0 mmol), bis(triphenylphosphine)palladium (II) chloride (280 mg, 0.400 mmol), and CuI (76.0 mg, 0.400 mmol) in anhydrous THF (73 mL) at ambient temperature. The resulting solution was stirred at ambient temperature for 3.5 hours, then diluted with diethyl ether, filtered through a pad of celite and the solvent removed in vacuo. Purification by flash chromatography on 330 g of silica, eluting with a gradient of 0-90% EtOAc in hexanes afforded 8.47 g, 96% of 1-7 as an off white foamy solid.

MS (ESI): m/z=443.2 (MH$^+$).

Methyl 2-{2-[(4αS,5R)-1-(4-fluorophenyl)-5-hydroxy-4α-methyl-1,4,4α,5,6,7-hexahydrocyclopenta[f]indazol-5-yl]ethyl}benzoate (1-8)

10% Pd/C (8.16 g) was added to a solution of 1-7 (8.48 g, 19.2 mmol) in EtOAc (128 mL) at ambient temperature and the flask evacuated and backfilled with hydrogen. The resulting suspension was stirred at ambient temperature under a balloon of hydrogen for 45 min, filtered through a pad of celite and the solvent removed in vacuo to afford 7.92 g, 93% of 1-8 as a pale yellow solid.

MS (ESI): m/z=447.2 (MH$^+$).

Example 2

Synthesis of 2-{2-[(4αS,5R)-1-(4-fluorophenyl)-5-hydroxy-4α-methyl-1,4,4α,5,6,7-hexahydrocyclopenta[f]indazol-5-yl]ethyl}-N-ethylbenzamide

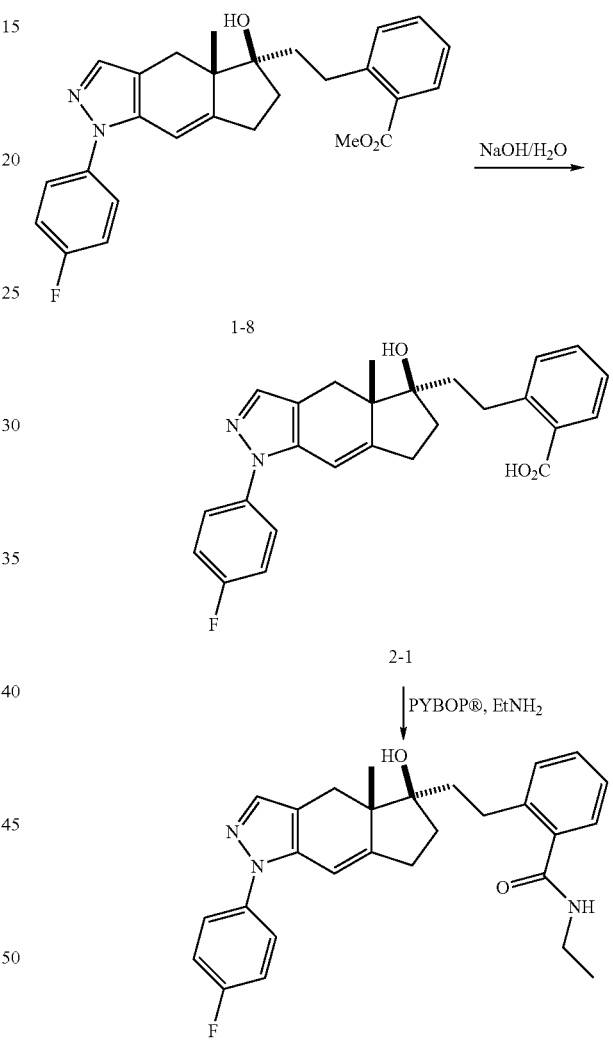

2-{2-[(4αS,5R)-1-(4-Fluorophenyl)-5-hydroxy-4α-methyl-1,4,4α,5,6,7-hexahydrocyclopenta[f]indazol-5-yl]ethyl}benzoic acid (2-1)

A 1M aqueous solution of NaOH (35.5 mL, 35.5 mmol) was added to a solution of 1-8 (7.92 g, 17.7 mmol) in MeOH (71 mL) and the resulting suspension heated at 100° C. for 1 hour. The methanol was removed in vacuo and saturated aqueous KH$_2$PO$_4$ solution was added and the crude product was extracted with EtOAc (×3). The combined organic extracts were dried over anhydrous MgSO$_4$ and the solvent removed in vacuo to afford 7.67 g, 100% of 1-9 as a pale yellow solid.

MS (ESI): m/z=433.2 (MH$^+$).

2-{2-[(4αS,5R)-1-(4-Fluorophenyl)-5-hydroxy-4α-methyl-1,4,4α,5,6,7-hexahydrocyclopenta[f]indazol-5-yl]ethyl}-N-ethylbenzamide (2-2)

A 2.0M solution of ethylamine in THF (5.55 mL, 11.10 mmol), PYBOP® (5.05 g, 9.71 mmol) and Hünig's Base (4.85 mL, 27.7 mmol) were added to a solution of 2-1 in anhydrous DMF (20 mL) at 0° C. The resulting solution was allowed to slowly warm to ambient temperature and stirred overnight (20 hours). The DMF was removed in vacuo, water was added and the crude product was extracted with EtOAc (×3). The combined organic extracts were washed with saturated sodium bicarbonate solution, dried over anhydrous MgSO$_4$, filtered and the solvent removed in vacuo. Purification by flash chromatography on 330 g of silica, eluting with a gradient of 10-100% [(CHCl$_3$/EtOAc/MeOH) (70/25/5)] in CHCl$_3$ afforded 3.04 g, 72% of 2-2 as an off white foamy solid.

MS (ESI): m/z=460.2395 (MH$^+$).

Example 3

SYNTHESIS of N-Ethyl-n'-(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl urea

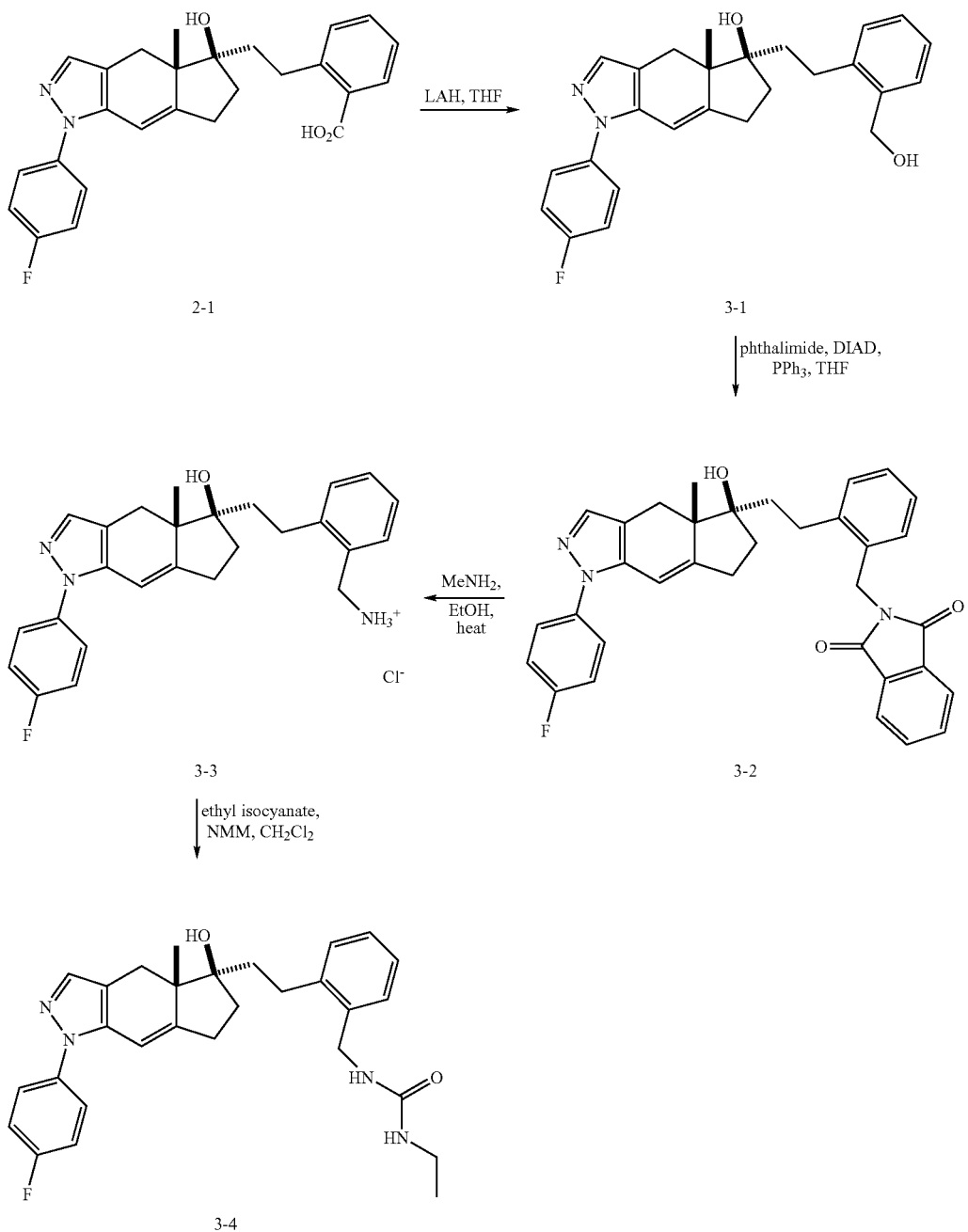

(4αS,5R)-1-(4-Fluorophenyl)-5-(2-[2-(hydroxymethyl)phenyl]ethyl)-4α-methyl-1,4,4α,5,6,7-hexahydrocyclopenta(f)indazol-5-ol (3-1)

A 1 M solution of lithium aluminum hydride in THF (27.7 mL, 27.7 mmol) was added to a stirred, 0° C. mixture of 2-1 (4.0 g, 9.25 mmol) in THF (50 mL) and the resulting mixture was allowed to warm to ambient temperature and then stirred for 30 min. The resulting reaction was heated at reflux for 1 hour cooled, diluted with aqueous ammonium chloride (saturated), and then extracted with ethyl acetate. The combined organic fractions were washed with brine, dried over anhydrous MgSO$_4$, filtered and the solvent was removed in vacuo. Purification by flash chromatography on 120 g of silica, eluting with a gradient of 0-100% EtOAc in hexanes afforded 3.2 g, 83% of 3-1 as a white solid.

MS (ESI): m/z=419.13 (MH$^+$).

2-(2-(2-[(4αS,5R)-1-(4-Fluorophenyl)-5-hydroxy-4α-methyl-1,4,4α,5,6,7-hexahydrocyclopenta(f)indazol-5-yl]ethyl)benzyl)-1H-isoindole-1,3(2H)-dione (3-2)

A solution of diisopropyl azodicarboxylate (1.6 mL, 9.03 mmol) was added to a solution of 3-1 (3.15 g, 7.53 mmol), phthalimide (1.33 g, 9.03 mmol), and triphenylphosphine (2.37 g, 9.03 mmol) in THF (35 mL) at 0° C. and the resulting solution warmed to ambient temperature and then stirred for 30 min. A solution of aqueous sodium carbonate (5%, 100 mL) was added and the mixture was extracted with ethyl acetate. The combined organic extracts were dried over anhydrous MgSO$_4$ and the solvent removed in vacuo. Purification by flash chromatography on 120 g of silica, eluting with a gradient of 0-100% EtOAc in hexanes afforded 4.0 g, 97% of 3-2 as a white solid.

MS (ESI): m/z=548.15 (MH$^+$).

(4αS,5R)-1-(4-Fluorophenyl)-5-(2-[2-(aminomethyl)phenyl]ethyl)-4α-methyl-1,4,4α,5,6,7-hexahydrocyclopenta(f)indazol-5-ol hydrochloride (3-3)

H$_2$O (20 mL) followed by a 2M solution of MeNH$_2$ in EtOH (20 mL, 40 mmol) were added to a solution of 3-2 (4.0 g, 7.30 mmol) in EtOH (50 mL) and the resulting solution heated at reflux. After 4 hours, the reaction was allowed to cool to ambient temperature and the EtOH was removed in vacuo. The mixture was diluted with EtOAc and then washed with 1N NaOH, brine, dried over anhydrous MgSO$_4$ and the solvent removed in vacuo. The resulting residue was dissolved in 50 mL EtOH, and 50 mL sat HCl/EtOH was added. After 10 minutes the solvent was removed in vacuo and the residue triturated with Et$_2$O to afford 3.2 g, 97% of 3-3 as the hydrochloride salt.

MS (ESI): m/z=418.21 (MH$^+$).

N-Ethyl-N'-(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl urea (3-4)

Ethyl isocyanate (22.6 mg, 0.317 mmol) was added to a stirred solution of 3-3 (120 mg, 0.264 mmol) and 4-methylmorpholine (0.116 mL, 1.06 mmol) in CH$_2$Cl$_2$ (1 mL). The mixture was stirred for 1 hour, diluted with EtOAc and washed with H$_2$O, sat NaHCO$_3$, brine, dried over anhydrous MgSO$_4$, filtered and the solvent was removed in vacuo to afford 129 mg, 88% of 3-4 as a white solid.

HRMS (APCI): m/z=489.2658 (MH$^+$).

Example 4

SYNTHESIS OF N-(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl cyclopropanecarboxamide

N-(2-(2-[(4αS,5R)-1-(4-Fluorophenyl)-5-hydroxy-4α-methyl-1,4,4α,5,6,7-hexahydrocyclo

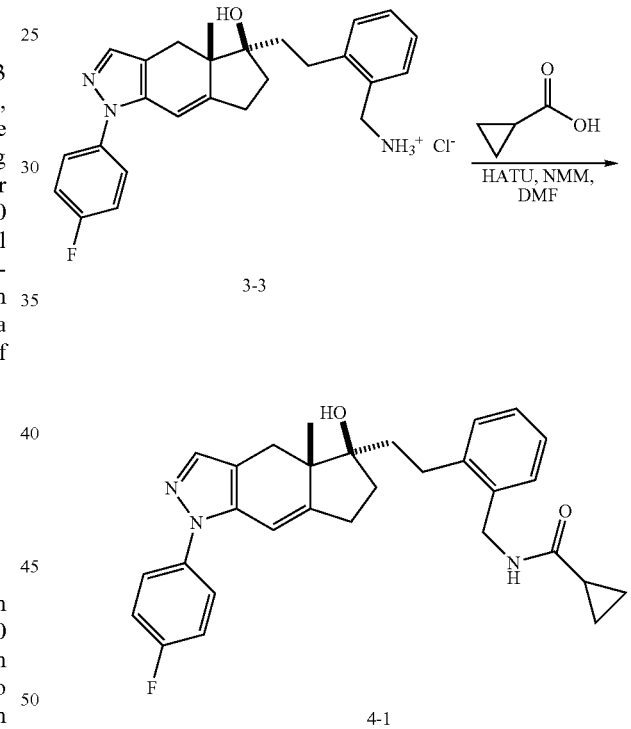

penta(f)indazol-5-yl]ethyl)benzyl)cyclopropanecarboxamide (4-1)

HATU (120 mg, 0.264 mmol) was added to a stirred solution of 3-3 (120 mg, 0.264 mmol), cyclopropane carboxylic acid (27.3 mg, 0.317 mmol), 4-methylmorpholine (0.116 mL, 1.06 mmol) and DMF (1 mL). The mixture was stirred for 16 hours and then was diluted with EtOAc and washed with H$_2$O, sat NaHCO$_3$, brine, dried over anhydrous MgSO$_4$, filtered and the solvent was removed in vacuo to afford 80 mg, 62% of 4-1 as a yellow foam.

HRMS (APCI): m/z=486.2571 (MH$^+$).

Example 5

SYNTHESIS of N-(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl cyclopropanesulfonamide

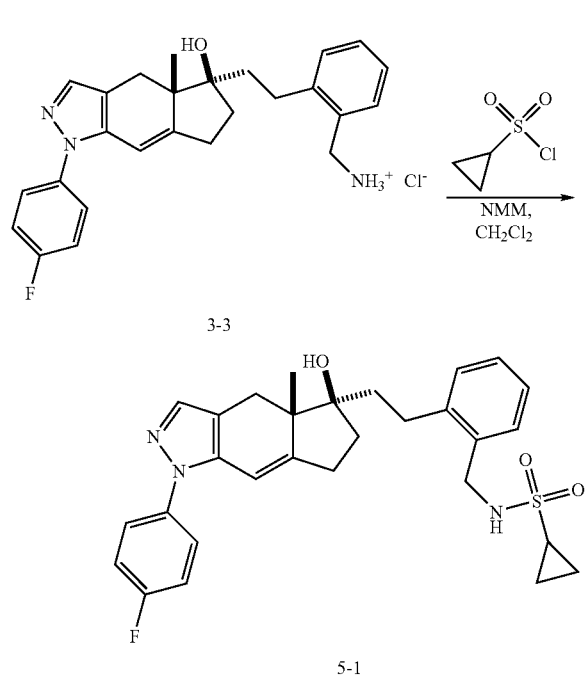

Example 6

SYNTHESIS of Ethyl(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl carbamate

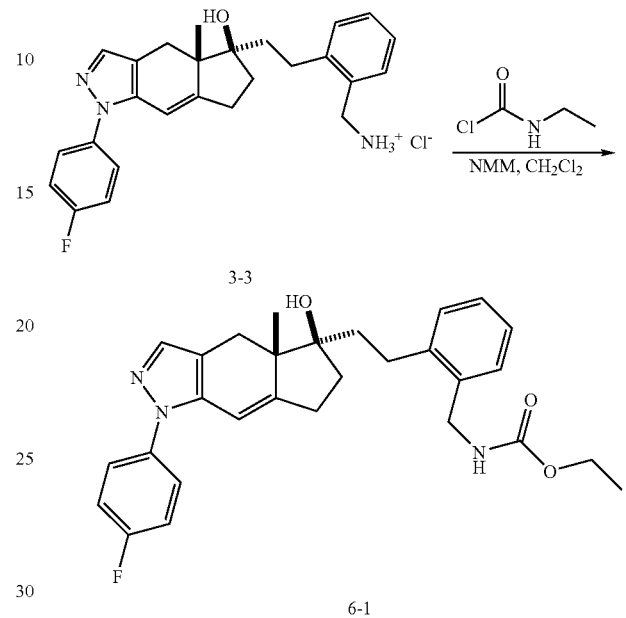

N-(2-(2-[(4αS,5R)-1-(4-Fluorophenyl)-5-hydroxy-4α-methyl-1,4,4α,5,6,7-hexahydrocyclopenta(f)indazol-5-yl]ethyl)benzyl)cyclopropanesulfonamide (5-1)

Cyclopropane sulfonyl chloride (44.6 mg, 0.317 mmol) was added to a stirred solution of 3-3 (120 mg, 0.264 mmol) and 4-methyl morpholine (0.116 mL, 1.06 mmol) in CH$_2$Cl$_2$ (1 mL). The mixture was stirred for 1 hour, diluted with EtOAc and washed with H$_2$O, sat NaHCO$_3$, brine, dried over anhydrous MgSO$_4$, filtered and the solvent removed in vacuo. Purification by flash chromatography on 12 g of silica, eluting with a gradient of 0-100% EtOAc in hexanes afforded 138 mg, 58% of 5-1 as a colorless foam.

HRMS (APCI): m/z=522.2230 (MH$^+$).

Ethyl(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl)carbamate (6-1)

Ethyl chloroformate (34.4 mg, 0.317 mmol) was added to a stirred solution of 3-3 (120 mg, 0.264 mmol) and 4-methyl morpholine (0.116 mL, 1.06 mmol) in CH$_2$Cl$_2$ (1 mL). The mixture was stirred for 1 hour and then was diluted with EtOAc and washed with H$_2$O, sat NaHCO$_3$, brine, dried over anhydrous MgSO$_4$, filtered and the solvent was removed in vacuo. Purification by flash chromatography on 12 g of silica, eluting with a gradient of 0-100% EtOAc in hexanes afforded (30 mg, 23%) of 6-1 as a colorless foam.

HRMS (APCI): m/z=490.2525 (MH$^+$).

Example 7

SYNTHESIS of N-[1-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)cyclopropyl]cyclopropanesulfonamide

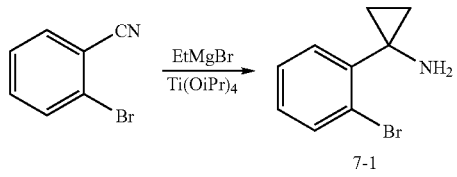

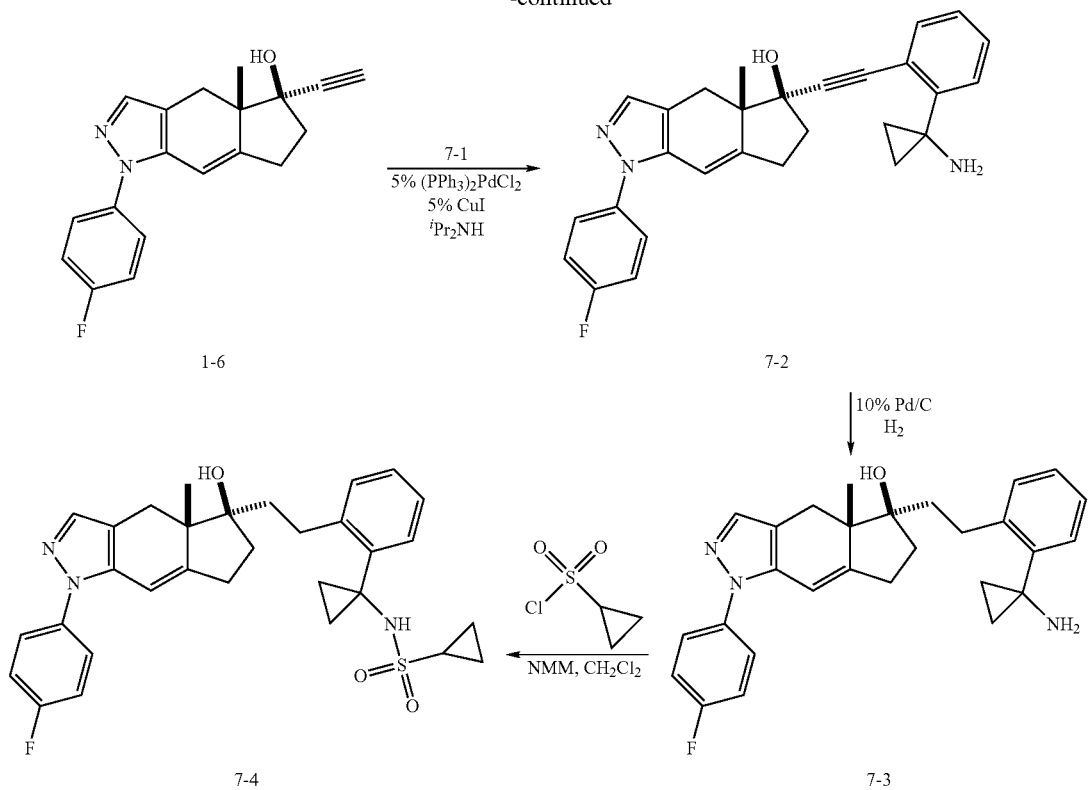

1-(2-Bromophenyl)cyclopropanamine (7-1)

Ethyl magnesium bromide (20.14 ml, 60.4 mmol) was added dropwise to a stirred, cooled −78° C. mixture of 2-bromobenzonitrile (5.0 g, 27.5 mmol) and titanium isopropoxide (8.59 g, 30.2 mmol) in ether (100 ml) and the mixture was stirred at −78° C. for 10 minutes. The yellow solution was warmed to ambient temperature and held for 1 hour. Boron trifluoride etherate (7.8 g, 54.9 mmol) was added dropwise and the mixture was stirred for 1 hour. 1 N HCl (90 ml) was added and the mixture was stirred for 10 minutes. Added 300 ml 1N NaOH and then extracted with ether. The organic portion was washed with brine, dried (MgSO$_4$) and the solvent removed in vacuo. Purification by flash chromatography on 80 g of silica, eluting with a gradient of 0-100% EtOAc in hexanes afforded 0.80 g, 14% of 7-1 as yellow oil.

MS (ESI): m/z=213.11 (MH$^+$).

(4αS,5R)-5-{2-(1-Aminocyclopropyl)phenyl]ethynyl}-1-(4-fluorophenyl)-4α-methyl-1,4,4α,5,6,7-hexahydrocyclopenta[f]indazol-5-ol (7-2)

Diisopropylamine (0.14 ml, 0.973 mmol) was added to a solution of 1-6 (300 mg, 0.973 mmol), 7-1 (206 mg, 0.973 mmol), bis(triphenylphosphine)palladium (II) chloride (34.1 mg, 0.049 mmol), and CuI (9.3 mg, 0.049 mmol) in anhydrous THF (5 ml) at ambient temperature. The resulting solution was heated at 70° C. for 18 hours, then diluted with diethyl ether, filtered through a pad of celite and the solvent removed in vacuo. Purification by flash chromatography on 40 g of silica, eluting with a gradient of 0-100% EtOAc in hexanes afforded 428 mg, 51% of 7-2 as an orange oil.

MS (ESI): m/z=440.16 (MH$^+$).

(4αS,5R)-5-{2-[2-(1-Aminocyclopropyl)phenyl]ethyl}-1-(4-fluorophenyl)-4α-methyl-1,4,4α,5,6,7-hexahydrocyclopenta[f]indazol-5-ol (7-3)

10% Pd/C (300 mg) was added to a solution of 7-2 (220 mg, 0.50 mmol) in EtOAc (10 ml) at ambient temperature and the flask evacuated and backfilled with hydrogen. The resulting suspension was stirred at ambient temperature under a balloon of hydrogen for 6 hours, filtered through a pad of celite and the solvent removed in vacuo to afford 95 mg, 43% of 7-3 as a yellow oil.

MS (ESI): m/z=444.24 (MH$^+$).

N-[1-(2-(2-[(4αS,5R)-1-(4-Fluorophenyl)-5-hydroxy-4α-methyl-1,4,4α,5,6,7-hexahydrocyclopenta(f)indazol-5-yl]ethyl}phenyl)cyclopropyl]cyclopropanesulfonamide (7-4)

Cyclopropane sulfonyl chloride (30.9 mg, 0.220 mmol) was added to a stirred solution of 7-3 (75 mg, 0.169 mmol) and 4-methyl morpholine (0.074 ml, 0.676 mmol) in CH$_2$Cl$_2$ (1 ml). The mixture was stirred for 16 hours, diluted with EtOAc and washed with H$_2$O, sat NaHCO$_3$, brine, dried over anhydrous MgSO$_4$, filtered and the solvent removed in vacuo. Purification by flash chromatography on 12 g of silica, eluting with a gradient of 0-100% EtOAc in hexanes afforded 42 mg, 45% of 7-4 as a colorless foam.

HRMS (ESI): m/z=548.2386 (MH$^+$).

Example 8

SYNTHESIS of N-[(1R)-1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]cyclopropanesulfonamide

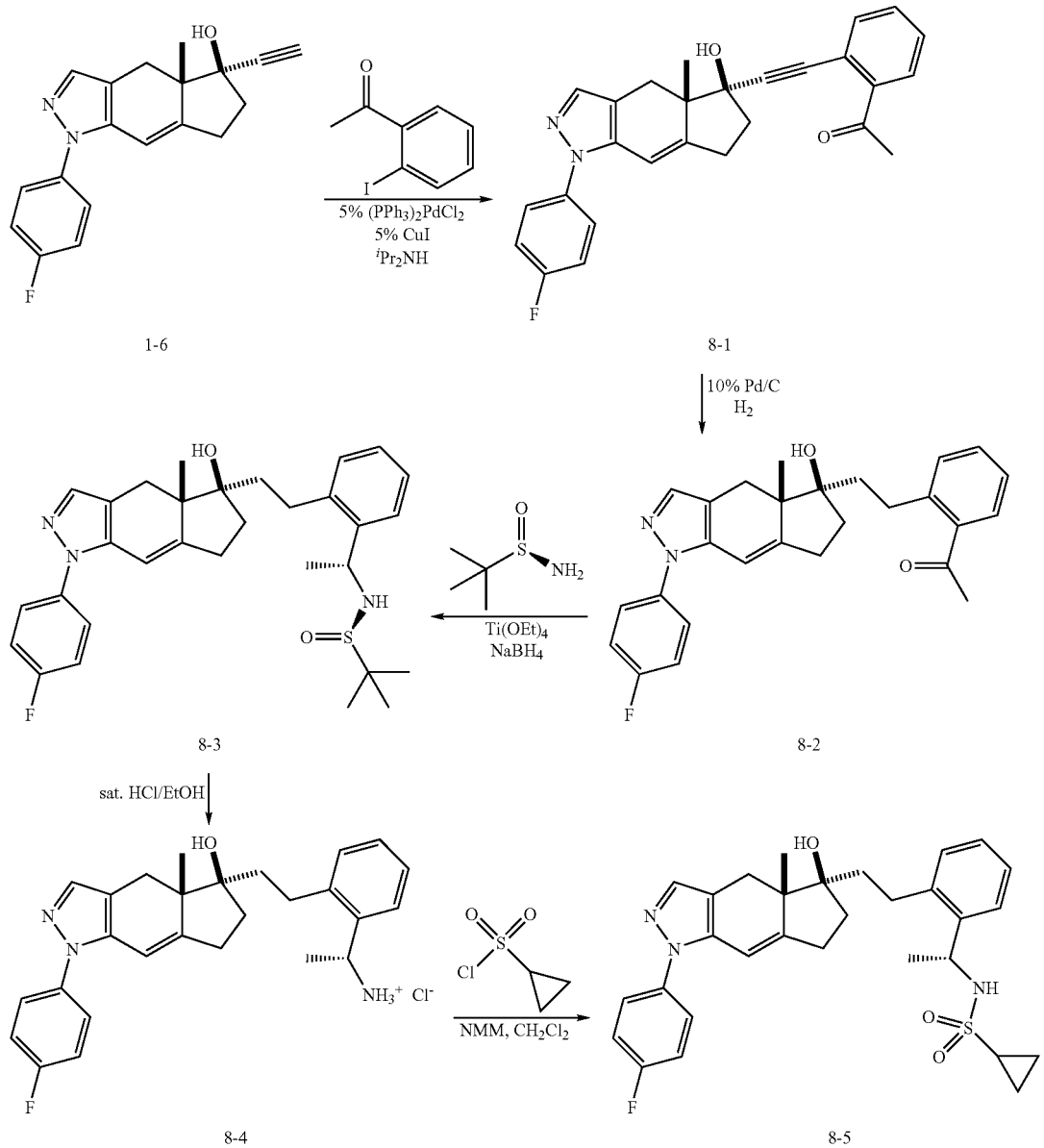

pad of celite and the solvent removed in vacuo. Purification by flash chromatography on 120 g of silica, eluting with a gradient of 0-100% EtOAc in hexanes afforded 2.6 g, 94% of 8-1 as an orange oil.

MS (ESI): m/z=427.22 (MH$^+$).

1-(2-{[(4αS,5R)-1-(4-Fluorophenyl)-5-hydroxy-4α-methyl-1,4,4α,5,6,7-hexahydrocyclopenta[f]indazol-5-yl]ethynyl}phenyl)ethanone (8-1)

Diisopropylamine (0.924 ml, 6.49 mmol) was added to a solution of 1-6 (2.0 g, 6.49 mmol), 1-(2-iodophenyl)ethanone (1-91 g, 7-78 mmol), bis(triphenylphosphine)palladium (II) chloride (228 mg, 0.324 mmol), and CuI (62 mg, 0.324 mmol) in anhydrous THF (20 ml) at ambient temperature. The resulting solution was stirred at ambient temperature for 18 hours, then diluted with diethyl ether, filtered through a 1-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)ethanone (8-2)

10% Pd/C (1.00 g) was added to a solution of 8-1 (2.50 g, 5.86 mmol) in EtOAc (50 ml) at ambient temperature and the flask evacuated and backfilled with hydrogen. The resulting suspension was stirred at ambient temperature under a balloon of hydrogen for 6 hours, filtered through a pad of celite and the solvent removed in vacuo. Purification by flash chromatography on 120 g of silica, eluting with a gradient of 0-100% EtOAc in hexanes afforded 2.30 g, 95% of 8-2 as a white solid.

MS (ESI): m/z=431.11 (MH$^+$).

N-[(1R)-1-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl]ethyl}ethyl]-2-(R)-methylpropane-2-sulfinamide (8-3)

Ti(OEt)$_4$ (1.2 ml, 5.81 mmol) was added to a stirred solution of ketone 8-2 (500 mg, 1.16 mmol) and R-(+)-methyl-2-propanesulfinamide (176 mg, 1.45 mmol) and the resulting solution was heated to 80° C. for 1 hour, cooled to −20° C. and then NaBH$_4$ (44 mg, 1.16 mmol) was added. After 1 hour, MeOH (5 ml) was added (vigorous bubbling). After 10 minutes, the cooling bath was removed and 20 ml brine and celite were added to produce a thick suspension. The mixture was filtered through a fritted funnel and the solids were washed with EtOAc. The organic portion was separated, dried (MgSO$_4$) and the solvent removed in vacuo. Purification by flash chromatography on 120 g of silica, eluting with a gradient of 0-100% EtOAc in hexanes afforded 355 mg, 57% of 8-3 as a colorless oil.

MS (ESI): m/z=536.20 (MH$^+$).

(1R)-1-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)ethanaminium chloride (8-4)

Saturated HCl/EtOH (2 ml) was added to a stirred solution of 8-3 (350 mg, 0.653 mmol) in EtOH (5 ml). The solution was stirred for 1 hour and the solvent removed in vacuo to afford 305 mg, 100% of 8-4 as yellow solid MS (ESI): m/z=432.26 (MH$^+$).

N-[(1R)-1-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)ethyl]cyclopropanesulfonamide (8-5)

Cyclopropane sulfonyl chloride (22.5 mg, 0.160 mmol) was added to a stirred solution of 8-4 (50 mg, 0.107 mmol) and 4-methyl morpholine (0.047 ml, 0.427 mmol) in CH$_2$Cl$_2$ (1 ml). The mixture was stirred for 16 hours, diluted with EtOAc and washed with H$_2$O, sat NaHCO$_3$, brine, dried over anhydrous MgSO$_4$, filtered and the solvent removed in vacuo. Purification by flash chromatography on 12 g of silica, eluting with a gradient of 0-100% EtOAc in hexanes afforded 22 mg, 38% of 8-5 as a colorless foam.

HRMS (ESI): m/z=536.2387 (MH$^+$).

Example 9

SYNTHESIS of 2-(2-[(4αS,5R)-1-(4-fluorophenyl)-5-hydroxy-4α-methyl-1,4,4α,5,6,7-hexahydrocyclopenta(f)indazol-5-yl]ethyl)benzyl)ethylcarbamate

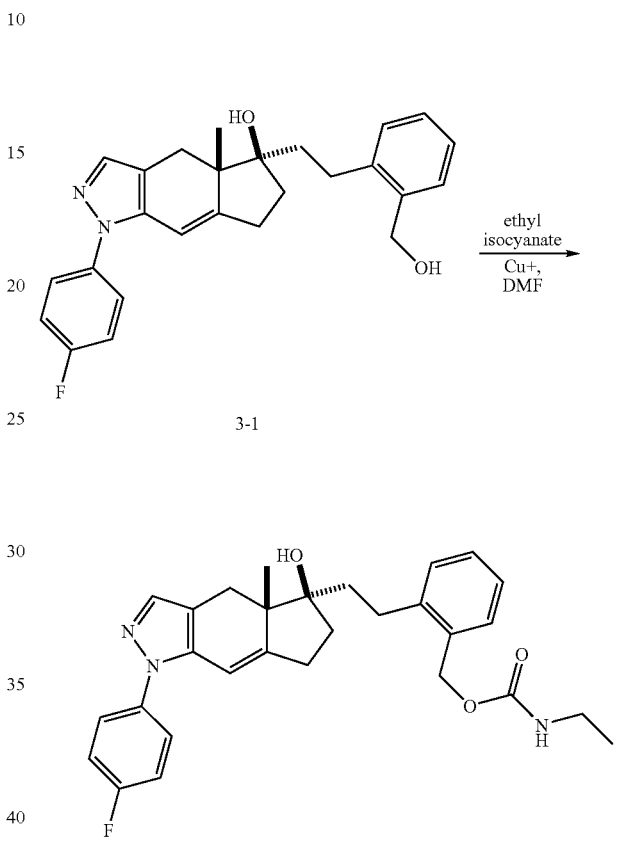

2-(2-[(4αS,5R)-1-(4-Fluorophenyl)-5-hydroxy-4α-methyl-1,4,4α,5,6,7-hexahydrocyclopenta(f)indazol-5-yl]ethyl)benzyl)ethylcarbamate (9-1)

A solution of 3-1 (100 mg, 0.239 mmol), in DMF (1 mL) was purged with nitrogen for 5 minutes and then ethyl isocyanate (20.4 mg, 0.287 mmol) and copper(I) trifluoromethanesulfonate benzene complex (72.8 mg, 0.239 mmol) were added to the degassed solution. The flask was sealed and the mixture was stirred for 5 hours then EtOAc (2 mL) was added followed by NH$_4$Cl solution (saturated, 1 mL) and NH$_4$OH (1 mL). The mixture was stirred for 5 minutes. The organic portion was separated and then was washed with brine, dried over anhydrous MgSO$_4$, filtered and the solvent was removed in vacuo. Purification by flash chromatography on 12 g of silica, eluting with a gradient of 0-100% EtOAc in hexanes afforded 30 mg, 26% of 9-1 as a yellow foam.

HRMS (APCI): m/z=490.2521 (MH$^+$).

Example 10
SYNTHESIS of (4αs,5r)-1-(4-fluorophenyl)-5-{2-[2-(6-fluoropyridin-3-yl)phenyl]ethyl}-4α-methyl-1,4,4α,5,6,7-hexahydrocyclopenta[f]indazol-5-ol
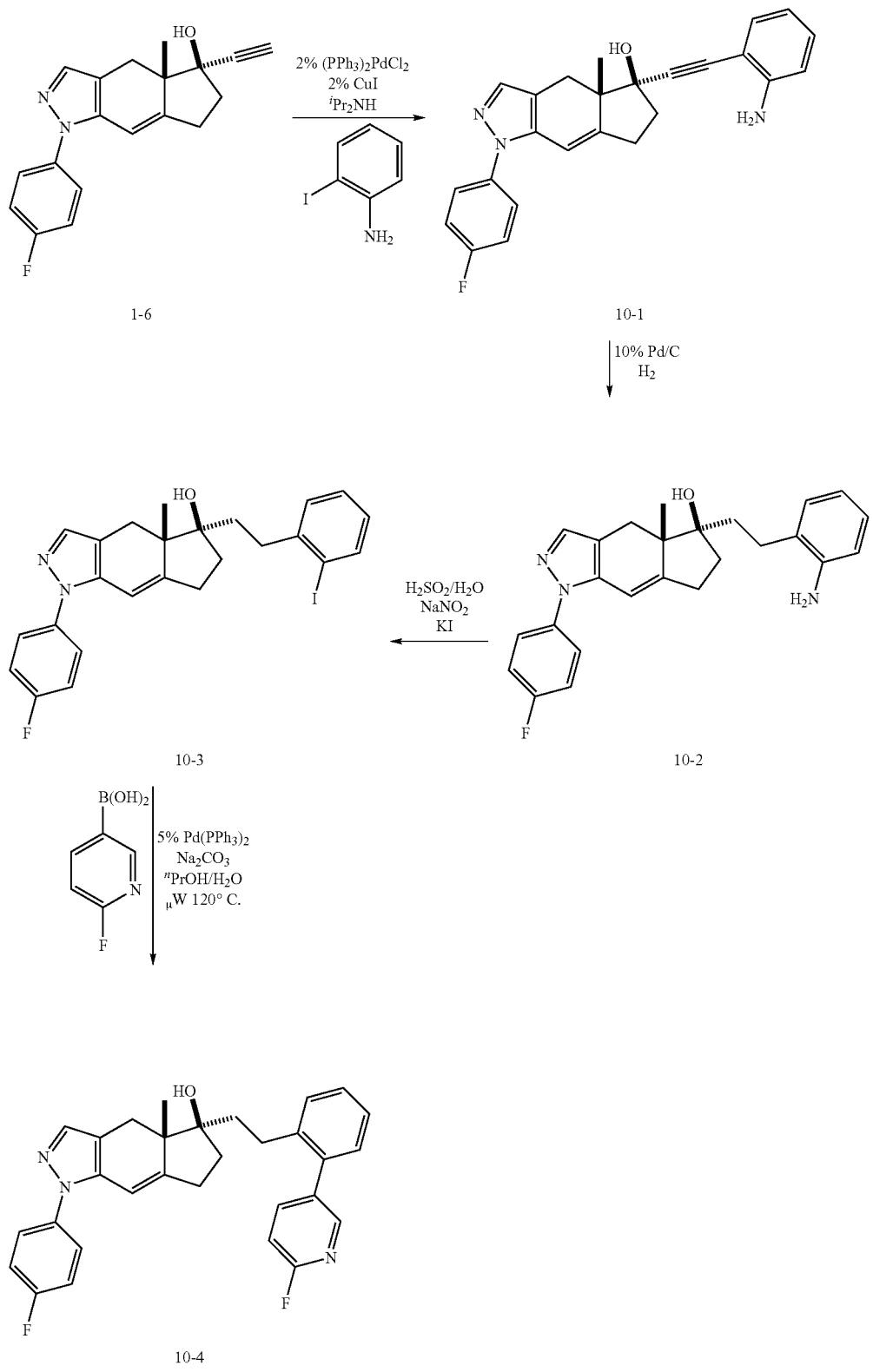

(4αS,5R)-5-[(2-Aminophenyl)ethynyl]-1-(4-fluorophenyl)-4α-methyl-1,4,4α,5,6,7-hexahydrocyclopenta[f]indazol-5-ol (10-1)

Diisopropylamine (1.39 mL, 9.73 mmol) was added to a solution of 1-6 (3.00 g, 9.73 mmol), 2-iodoaniline (2.56 g, 11.7 mmol), bis(triphenylphosphine)palladium (II) chloride (137 mg, 0.195 mmol), and CuI (37.0 mg, 0.195 mmol) in anhydrous THF (35 mL) at ambient temperature. The resulting solution was stirred 70° C. overnight, then diluted with diethyl ether, filtered through a pad of celite and the solvent removed in vacuo. Purification by flash chromatography on 120 g of silica, eluting with a gradient of 0-100% EtOAc in hexanes afforded 3.11 g, 80% of 10-1 as a tan solid.

MS (ESI): m/z=400.2 (MH$^+$).

(4αS,5R)-5-[2-(2-Aminophenyl)ethyl]-1-(4-fluorophenyl)-4α-methyl-1,4,4α,5,6,7-hexahydrocyclopenta[f]indazol-5-ol (10-2)

10% Pd/C (3.31 g) was added to a solution of 10-1 (3.11 g, 7.79 mmol) in EtOAc (50 mL) at ambient temperature and the flask evacuated and backfilled with hydrogen. The resulting suspension was stirred at ambient temperature under a balloon of hydrogen for 2 hours, filtered through a pad of celite and the solvent removed in vacuo to afford 3.14 g, 100% of 10-2 as a white solid.

MS (ESI): m/z=404.2 (MH$^+$).

(4αS,5R)-1-(4-Fluorophenyl)-5-[2-(2-iodophenyl)ethyl]-4a-methyl-1,4,4α,5,6,7-hexahydrocyclopenta[f]indazol-5-ol (10-3)

Concentrated sulfuric acid was added to a suspension of 10-2 (1.97 g, 4.88 mmol) in water (10 mL) at 0° C. A solution of NaNO$_2$ (337 mg, 4.88 mmol) in water (2 mL) was added and the resulting yellow solution stirred at 0° C. for 15 min. A solution of KI (2.43 g, 14.6 mmol) in water (2 mL) was added and the resulting suspension was warmed to ambient temperature and stirred for 40 min. The reaction was quenched with water and the crude product extracted with EtOAc (×3). The combined organic extracts were washed with 10% w/v Na$_2$S$_2$O$_3$ solution, dried over anhydrous MgSO$_4$ and the solvent removed in vacuo. Purification by flash chromatography on 40 g of silica, eluting with a gradient of 0-60% EtOAc in hexanes afforded 1.68 g, 67% of 10-3 as a white solid.

MS (ESI): m/z=515.1 (MH$^+$).

(4αS,5R)-1-(4-Fluorophenyl)-5-{2-[2-(6-fluoropyridin-3-yl)phenyl]ethyl}-4α-methyl-1,4,4a,5,6,7-hexahydrocyclopenta[f]indazol-5-ol (10-4)

A solution of 8-3 (30 mg, 0.058 mmol), (6-fluoropyridin-3-yl)boronic acid (9.9 mg, 0.070 mmol), Pd(PPh$_3$)$_4$ (3.4 mg, 2.9 µmmol), and Na$_2$CO$_3$ (12 mg, 0.12 mmol) in "propanol:water 3:1 (0.30 mL) was heated at 120° C. for 15 min in a microwave reactor. The reaction was quenched with water and the crude product extracted with EtOAc (×3). The combined organic extracts were dried over anhydrous MgSO$_4$ and the solvent removed in vacuo. Purification by flash chromatography on 4 g of silica, eluting with a gradient of 0-100% EtOAc in hexanes afforded 23 mg, 81% of 10-4 as a tan solid.

MS (ESI): m/z=484.2 (MH$^+$).

Example 11

SYNTHESIS of (4αs,5r)-1-(4-fluorophenyl)-5-{2-[2-(6-fluoropyridin-3-yl)phenyl]ethyl}-4α-methyl-1,4,4α,5,6,7-hexahydrocyclopenta[f]indazol-5-ol

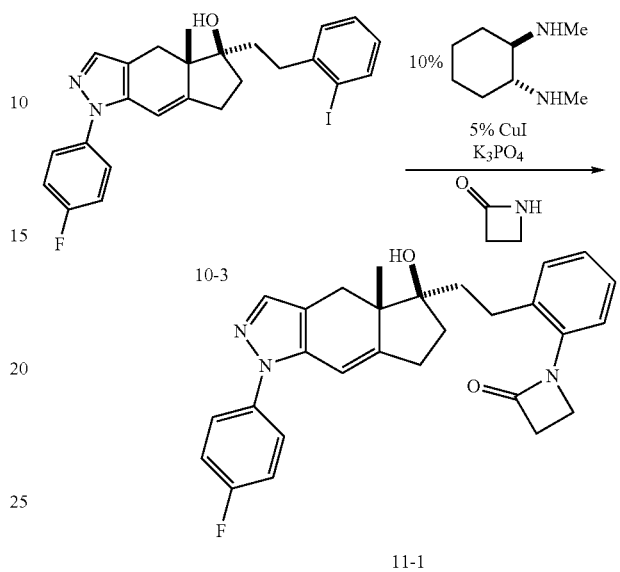

11-1

(4αS,5R)-1-(4-Fluorophenyl)-5-{2-[2-(6-fluoropyridin-3-yl)phenyl]ethyl}-4α-methyl-1,4,4a,5,6,7-hexahydrocyclopenta[f]indazol-5-ol (11-1)

A solution of 10-3 (50 mg, 0.097 mmol), azetidin-2-one (6.9 mg, 0.097 mmol), CuI (0.93 mg, 24.9 µmol), trans-(1R, 2R)—N,N'-bismethyl-1,2-cyclohexane diamine (1.40 mg, 9.72 µmol) and K$_3$PO$_4$ (12 mg, 0.12 mmol) in toluene (389 µL) was heated at 100° C. for 18 hours The reaction was quenched with water and the crude product extracted with EtOAc (×3). The combined organic extracts were dried over anhydrous MgSO$_4$ and the solvent removed in vacuo. Purification by flash chromatography on 4 g of silica, eluting with a gradient of 0-100% EtOAc in hexanes afforded 41 mg, 91% of 11-1 as a white solid.

MS (ESI): m/z=458.2 (MH$^+$).

Example 12

SYNTHESIS of Ethyl(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)carbamate

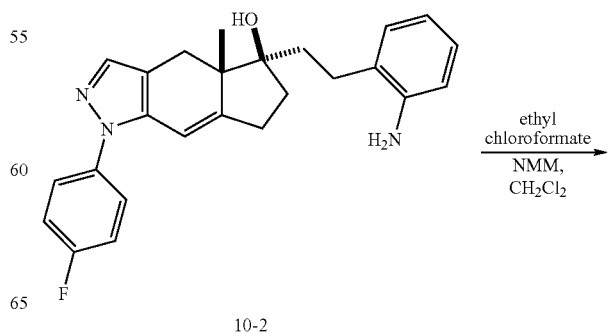

10-2

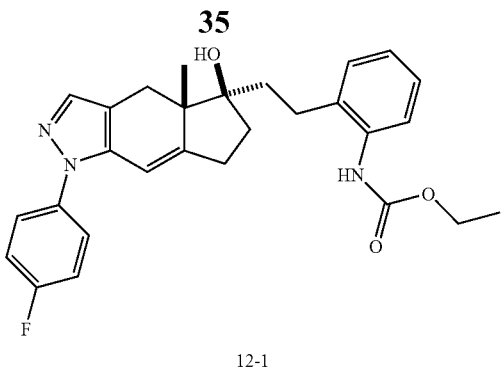

12-1

Ethyl(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)carbamate (4-2)

Ethyl chloroformate (13.5 mg, 0.124 mmol) was added to a stirred solution of 10-2 (50 mg, 0.124 mmol), DMAP (5 mg) and 4-methyl morpholine (0.054 ml, 0.496 mmol) in CH₂Cl₂ (1 ml). The mixture was stirred for 16 hours and then was diluted with CH₂Cl₂ and washed with H₂O, sat NaHCO₃, brine, dried over anhydrous MgSO₄, filtered and the solvent was removed in vacuo. Purification by flash chromatography on 12 g of silica, eluting with a gradient of 0-100% EtOAc in hexanes afforded (26 mg, 44%) of 12-1 as colorless foam.
HRMS (ESI): m/z=476.2335 (MH⁺).

Example 13

SYNTHESIS of N-ethyl-N'-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl urea

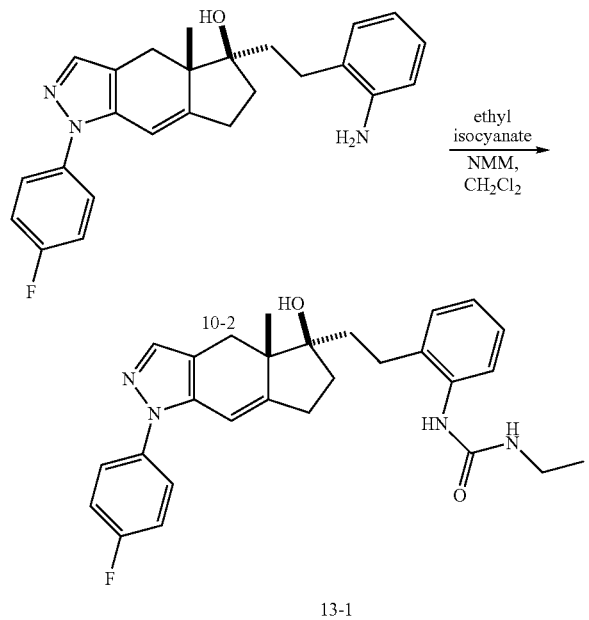

13-1

N-Ethyl-N'-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)urea (13-1)

Ethyl isocyanate (11.0 mg, 0.155 mmol) was added to a stirred solution of 10-2 (50 mg, 0.124 mmol), DMAP (5 mg) and 4-methyl morpholine (0.054 ml, 0.496 mmol) in CH₂Cl₂ (1 ml). The mixture was stirred for 6 hours then diluted with CH₂Cl₂, washed with H₂O, sat NaHCO₃, brine, dried over anhydrous MgSO₄, filtered and the solvent was removed in vacuo. Purification by flash chromatography on 12 g of silica, eluting with a gradient of 0-100% EtOAc in hexanes afforded (28 mg, 48%) of 13-1 as a colorless foam.
HRMS (ESI): m/z=475.2494 (MH⁺).

Example 14

SYNTHESIS of N-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetamide

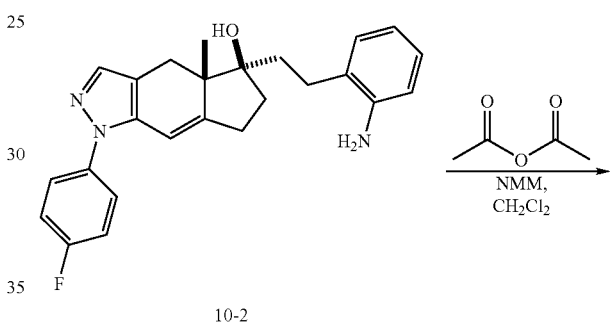

10-2

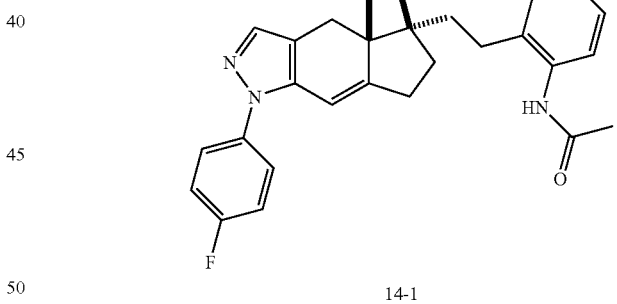

14-1

N-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)acetamide (14-1)

Acetic anhydride (15.2 mg, 0.149 mmol) was added to a stirred solution of 10-2 (50 mg, 0.124 mmol), DMAP (5 mg) and 4-methyl morpholine (0.054 ml, 0.496 mmol) in CH₂Cl₂ (1 ml). The mixture was stirred for 6 hours and then was diluted with CH₂Cl₂ and washed with H₂O, sat NaHCO₃, brine, dried over anhydrous MgSO₄, filtered and the solvent was removed in vacuo. Purification by flash chromatography on 12 g of silica, eluting with a gradient of 0-100% EtOAc in hexanes afforded (22 mg, 40%) of 14-1 as a colorless foam.
HRMS (ESI): m/z=446.2239 (MH⁺).

Example 15

SYNTHESIS of N-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)cyclopropanesulfonamide

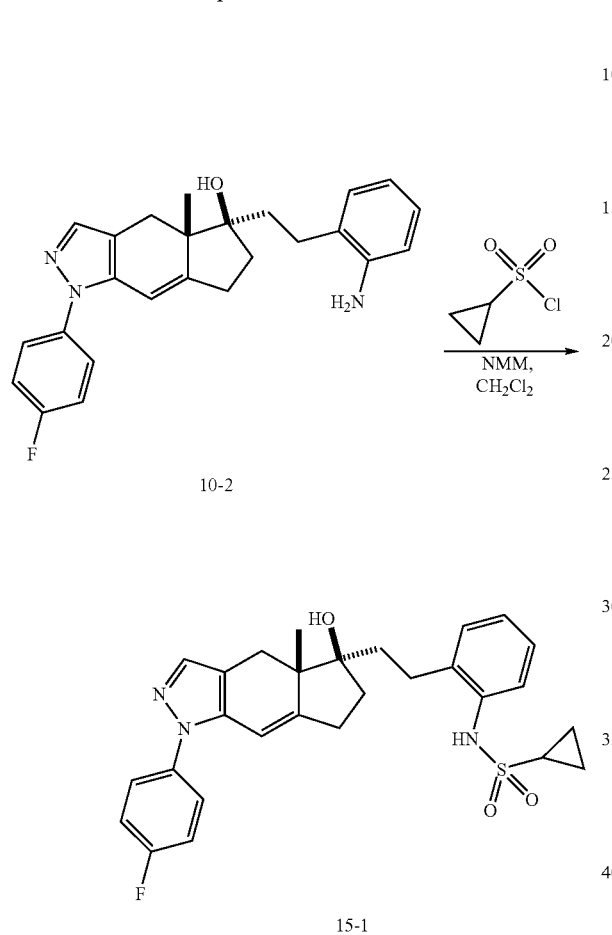

N-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)cyclopropanesulfonamide (15-1)

Cyclopropane sulfonyl chloride (20.9 mg, 0.149 mmol) was added to a stirred solution of 10-2 (50 mg, 0.124 mmol), DMAP (5 mg) and 4-methyl morpholine (0.054 ml, 0.496 mmol) in CH$_2$Cl$_2$ (1 ml). The mixture was stirred for 6 hours and then was diluted with CH$_2$Cl$_2$ and washed with H$_2$O, sat NaHCO$_3$, brine, dried over anhydrous MgSO$_4$, filtered and the solvent was removed in vacuo. Purification by flash chromatography on 12 g of silica, eluting with a gradient of 0-100% EtOAc in hexanes afforded (15 mg, 24%) of 15-1 as a colorless foam.

HRMS (ESI): m/z=508.2055 (MH$^+$).

Example 16

SYNTHESIS of (4αS,5R)-1-(4-fluorophenyl)-5-[2-(2-hydroxyphenyl)ethyl]-4α-methyl-1,4,4α,5,6,7-hexahydrocyclopenta[f]indazol-5-ol

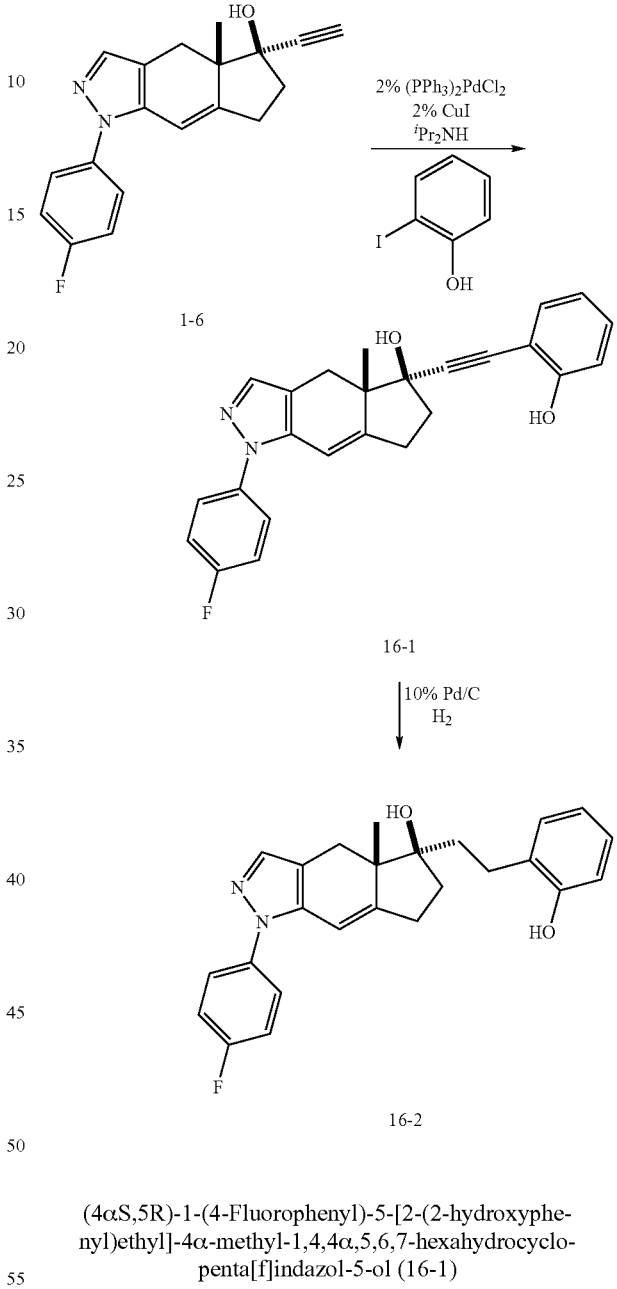

(4αS,5R)-1-(4-Fluorophenyl)-5-[2-(2-hydroxyphenyl)ethyl]-4α-methyl-1,4,4α,5,6,7-hexahydrocyclopenta[f]indazol-5-ol (16-1)

Diisopropylamine (116 µL, 0.811 mmol) was added to a solution of 1-6 (250 mg, 0.811 mmol), 2-iodophenol (214 mg, 0.973 mmol), bis(triphenylphosphine)palladium (II) chloride (11.4 mg, 0.016 mmol), and CuI (3.1 mg, 0.016 mmol) in anhydrous THF (3 mL) at ambient temperature. The resulting solution was stirred 70° C. overnight, then diluted with diethyl ether, filtered through a pad of celite and the solvent removed in vacuo. Purification by flash chromatography on 12 g of silica, eluting with a gradient of 0-65% EtOAc in hexanes afforded 265 mg, 82% of 16-1 as a white solid.

MS (ESI): m/z=401.2 (MH$^+$).

(4αS,5R)-1-(4-Fluorophenyl)-5-[(2-hydroxyphenyl) ethynyl]-4α-methyl-1,4,4α,5,6,7-hexahydrocyclopenta[f]indazol-5-ol (16-2)

10% Pd/C (282 mg) was added to a solution of 10-1 (265 mg, 0.662 mmol) in EtOAc (4.5 mL) at ambient temperature and the flask evacuated and backfilled with hydrogen. The resulting suspension was stirred at ambient temperature under a balloon of hydrogen for 45 mins, filtered through a pad of celite and the solvent removed in vacuo. Purification by flash chromatography on 12 g of silica, eluting with a gradient of 0-80% EtOAc in hexanes afforded 183 mg, 68% of 16-2 as a white solid.

MS (ESI): m/z=405.2 (MH$^+$).

Example 17

SYNTHESIS of Ethyl-2-(2-[(4αS,5R)-1-(4-fluorophenyl)-5-hydroxy-4α-methyl-1,4,4α,5,6,7-hexahydrocyclopenta(f)indazol-5-yl]ethyl)phenylcarbonate

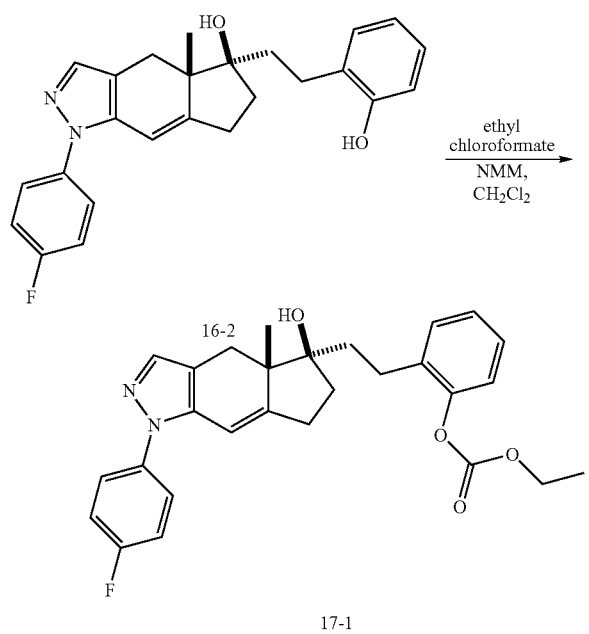

Ethyl-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)carbonate (17-1)

Ethyl chloroformate (13.4 mg, 0.124 mmol) was added to a stirred solution of 16-2 (50 mg, 0.124 mmol), DMAP (5 mg) and 4-methyl morpholine (0.054 ml, 0.496 mmol) in CH$_2$Cl$_2$ (1 ml). The mixture was stirred for 6 hours and then was diluted with CH$_2$Cl$_2$ and washed with H$_2$O, sat NaHCO$_3$, brine, dried over anhydrous MgSO$_4$, filtered and the solvent was removed in vacuo. Purification by flash chromatography on 12 g of silica, eluting with a gradient of 0-100% EtOAc in hexanes afforded (36 mg, 61%) of 17-1 as a colorless foam.

HRMS (ESI): m/z=477.2173 (MH$^+$).

Example 18

SYNTHESIS of 2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)ethylcarbamate

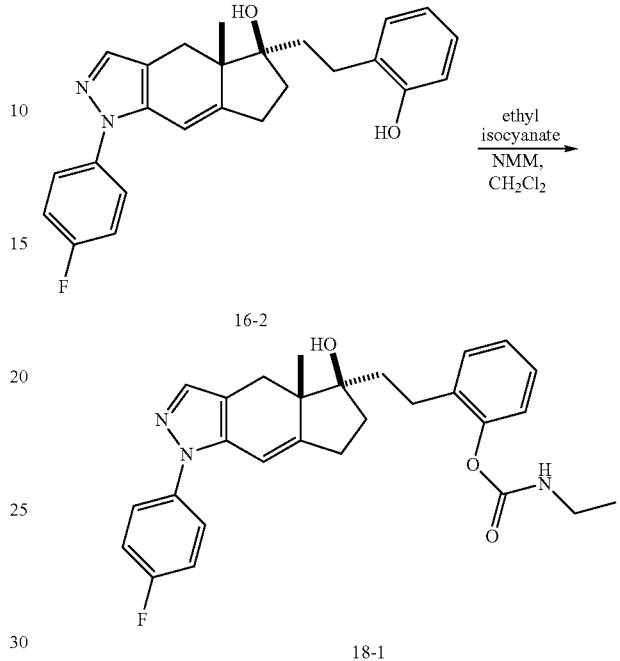

2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)ethylcarbamate (18-1)

Ethyl isocyanate (22.6 mg, 0.317 mmol) was added to a stirred solution of 16-2 (50 mg, 0.124 mmol), DMAP (5 mg) and 4-methyl morpholine (0.054 ml, 0.496 mmol) in CH$_2$Cl$_2$ (1 ml). The mixture was stirred for 6 hours and then was diluted with CH$_2$Cl$_2$ and washed with H$_2$O, sat NaHCO$_3$, brine, dried over anhydrous MgSO$_4$, filtered and the solvent was removed in vacuo. Purification by flash chromatography on 12 g of silica, eluting with a gradient of 0-100% EtOAc in hexanes afforded (38 mg, 65%) of 18-1 as a colorless foam.

HRMS (ESI): m/z=476.2335 (MH$^+$).

Example 19

SYNTHESIS of (4αS,5R)-1-(4-fluorophenyl)-4α-methyl-5-{2-[2-(methylsulfonyl)phenyl]ethyl}-1,4,4α,5,6,7-hexahydrocyclopenta[f]indazol-5-ol

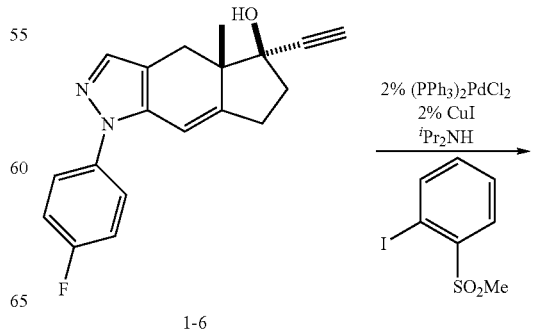

Example 20

SYNTHESIS of 2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile

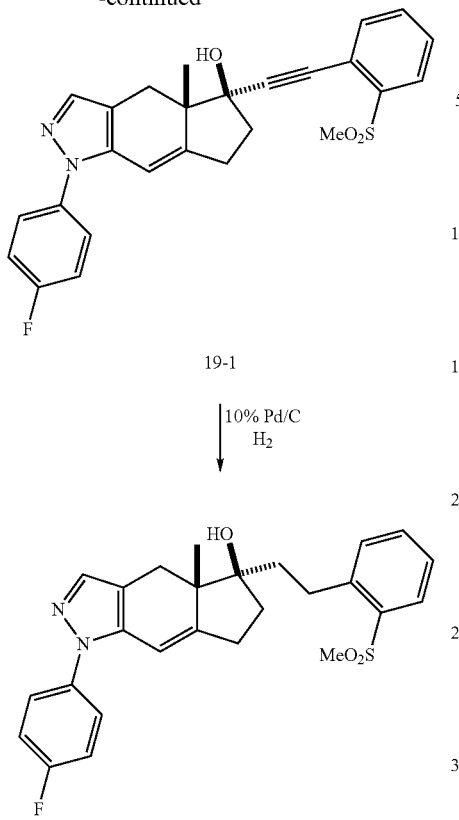

19-1

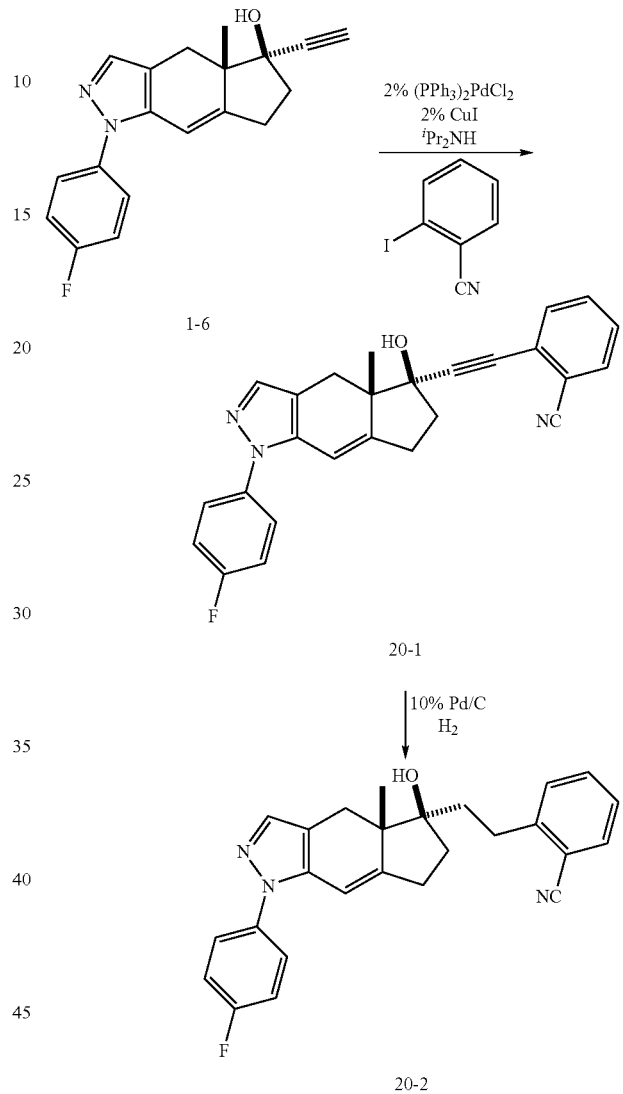

(4αS,5R)-1-(4-Fluorophenyl)-4α-methyl-5-{[2-(methylsulfonyl)phenyl]ethynyl}-1,4,4α,5,6,7-hexahydrocyclopenta[f]indazol-5-ol (19-1)

Diisopropylamine (0.048 mL, 0.334 mmol) was added to a solution of 1-6 (103 mg, 0.334 mmol), 1-iodo-2-(methylsulfonyl)benzene (113 mg, 0.401 mmol), bis(triphenylphosphine)palladium (II) chloride (23.5 mg, 0.033 mmol), and CuI (6.36 mg, 0.033 mmol) in anhydrous THF (1.0 mL) at ambient temperature. The resulting solution was stirred in an oil bath at 70° C. for 1.5 hours, then diluted with diethyl ether, filtered through a pad of celite and the solvent removed in vacuo. Purification by flash chromatography on 40 g of silica, eluting with a gradient of 0-100% EtOAc in hexanes afforded 117 mg, 83% of the 19-1 as a white foamy solid.
MS (ESI): m/z=463.1 (MH$^+$).

(4αS,5R)-1-(4-Fluorophenyl)-4α-methyl-5-{2-[2-(methylsulfonyl)phenyl]ethyl}-1,4,4α,5,6,7-hexahydrocyclopenta[f]indazol-5-ol (19-2)

10% Pd/C (125 mg) was added to a solution of 19-1 (117 mg, 0.253 mmol) in EtOAc (3.5 mL) at ambient temperature and the flask evacuated and backfilled with hydrogen. The resulting suspension was stirred at ambient temperature under a balloon of hydrogen for 4 hours, filtered through a pad of celite and the solvent removed in vacuo. Purification by flash chromatography on 80 g of silica, eluting with a gradient of 40-100% EtOAc in hexanes afforded 63 mg, 53% of 19-2 as a white foamy solid.
MS (ESI): m/z=467.2 (MH$^+$).

2-{[(4αS)-1-(4-Fluorophenyl)-5-hydroxy-4α-methyl-1,4,4α,5,6,7-hexahydrocyclopenta[f]indazol-5-yl]ethynyl}benzonitrile (20-1)

Diisopropylamine (0.052 mL, 0.364 mmol) was added to a solution of 1-6 (112 mg, 0.363 mmol), 2-iodobenzonitrile (113 mg, 0.401 mmol), bis(triphenylphosphine)palladium (II) chloride (5.10 mg, 0.008 mmol), and CuI (1.38 mg, 0.008 mmol) in anhydrous THF (1.0 mL) at ambient temperature. The resulting solution was stirred at ambient temperature for 2.0 hours, then diluted with diethyl ether, filtered through a pad of celite and the solvent removed in vacuo. Purification by flash chromatography on 40 g of silica, eluting with a gradient of 0-90% EtOAc in hexanes afforded 50 mg, 33% of 20-1 as a yellow foamy solid.
MS (ESI): m/z=410.2 (MH$^+$).

2-{2-[(4αS,5R)-1-(4-Fluorophenyl)-5-hydroxy-4α-methyl-1,4,4α,5,6,7-hexahydrocyclopenta[f]indazol-5-yl]ethyl}benzonitrile (20-2)

10% Pd/C (52 mg) was added to a solution of 20-1 (50 mg, 0.122 mmol) in EtOAc (1.5 mL) at ambient temperature and the flask evacuated and backfilled with hydrogen. The resulting suspension was slowly stirred at ambient temperature under a balloon of hydrogen for 4 hours, filtered through a pad of celite and the solvent removed in vacuo. Purification by flash chromatography on 12 g of silica, eluting with a gradient of 0-80% EtOAc in hexanes afforded 37 mg, 73% of 20-2 as a white foamy solid.

MS (ESI): m/z=414.2 (MH+).

Example 21

SYNTHESIS of 2-(2-[(4αS,5R)-1-(4-fluorophenyl)-5-hydroxy-4α-methyl-1,4,4α,5,6,7-hexahydrocyclopenta(f)indazol-5-yl]ethyl)benzaldehyde

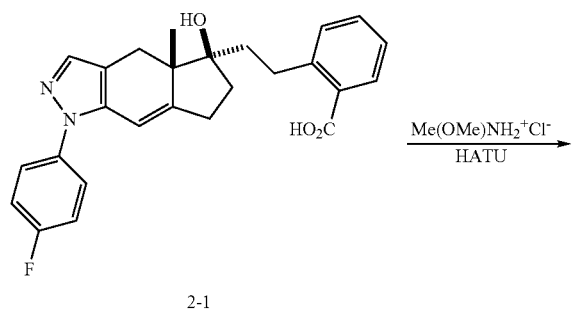

2-1

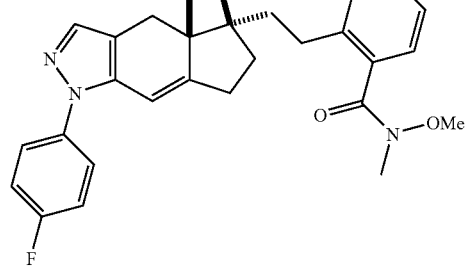

21-1

| Dibal-H,
| THF

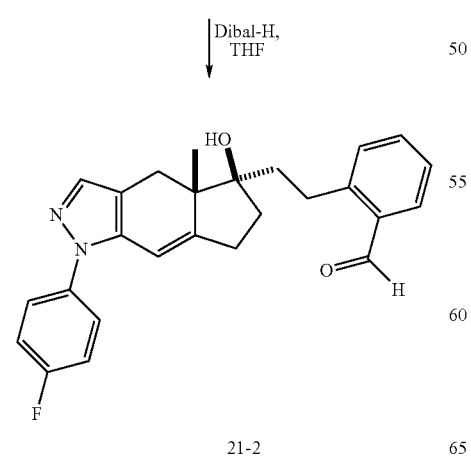

21-2

2-{2-[(4αS,5R)-1-(4-Fluorophenyl)-5-hydroxy-4α-methyl-1,4,4α,5,6,7-hexahydrocyclopenta[f]indazol-5-yl]ethyl}-N-methoxy-N-methylbenzamide (21-1)

HATU (3.17 g, 8.32 mmol) was added to a stirred solution of 2-1 (3.0 g, 6.94 mmol), methoxy(methylammonium)chloride (880 mg, 9.02 mmol), 4-methylmorpholine (3.06 ml, 27.7 mmol) and DMF (20 ml). The mixture was stirred for 72 hours and then was diluted with EtOAc and washed with $H_2O$, sat $NaHCO_3$, brine, dried over anhydrous $MgSO_4$, filtered and the solvent was removed in vacuo to afford 3.30 g, 100% of 21-1 as a tan foam.

MS (ESI): m/z=476.16 (MH+).

2-{2-[(4αS,5R)-1-(4-Fluorophenyl)-5-hydroxy-4α-methyl-1,4,4α,5,6,7-hexahydrocyclopenta[f]indazol-5-yl]ethyl}benzaldehyde (21-2)

A solution of Dibal-H (15.27 ml, 15.27 mmol, 1M) was added to a solution of 21-1 (3.3 g, 6.94 mmol) in THF (3 ml) at −78° C. and the resulting solution was stirred for 2 hours. A solution of aqueous saturated Rochelle's salt (30 ml) was added followed by the removal of the cooling bath. The mixture was stirred for 1 hour and then was extracted with $CH_2Cl_2$ (200 ml). The organic extracts were washed with brine, dried over anhydrous $MgSO_4$ and the solvent removed in vacuo to afford 2.60 g, 90% of 21-2 as a tan foam.

HRMS (ESI): m/z=417.1969 (MH+).

Example 22

SYNTHESIS of 2-{[(4αS,5R)-1-(4-fluorophenyl)-5-hydroxy-4α-methyl-1,4,4α,5,6,7-hexahydrocyclopenta(f)indazol-5-yl]ethyl}benzene sulfonamide

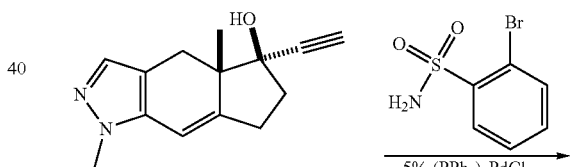

1-6

| 5% $(PPh_3)_2PdCl_2$
| 5% CuI
| $^iPr_2NH$

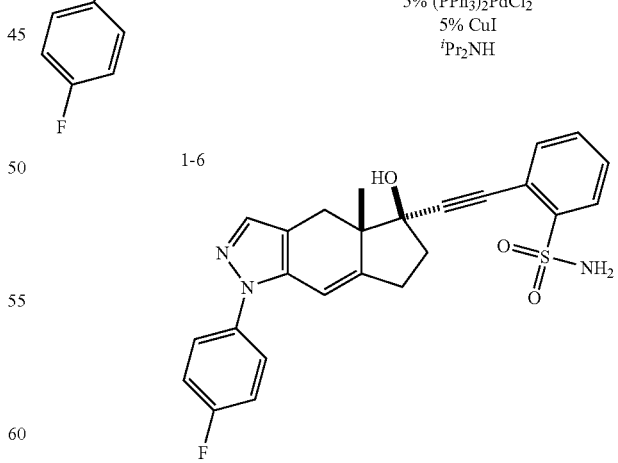

22-1

| 10% Pd/C
| $H_2$

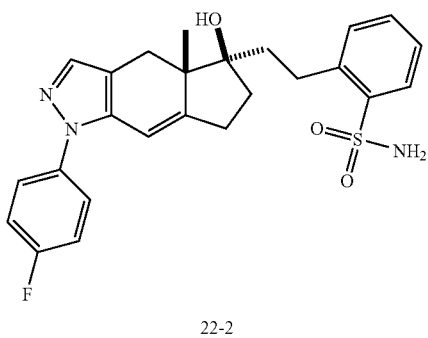

2-{[(4αS,5R)-1-(4-Fluorophenyl)-5-hydroxy-4α-methyl-1,4,4α,5,6,7-hexahydrocyclopenta[f]indazol-5-yl]ethynyl}benzenesulfonamide (22-1)

Diisopropylamine (0.051 ml, 0.357 mmol) was added to a solution of 1-6 (110 mg, 0.357 mmol), 2-bromobenzenesulfonamide (84 mg, 0.357 mmol), bis(triphenylphosphine) palladium (II) chloride (12.5 mg, 0.018 mmol), and CuI (3.4 mg, 0.018 mmol) in anhydrous THF (2 ml) at ambient temperature. The resulting solution was stirred at 60° C. for 18 hours, then diluted with diethyl ether, filtered through a pad of celite and the solvent removed in vacuo. Purification by flash chromatography on 12 g of silica, eluting with a gradient of 0-100% EtOAc in hexanes afforded 90 mg, 54% of 22-1 as an orange oil.

MS (ESI): m/z=464.16 (MH$^+$).

2-{[(4αS,5R)-1-(4-Fluorophenyl)-5-hydroxy-4α-methyl-1,4,4α,5,6,7-hexahydrocyclopenta[f]indazol-5-yl]ethyl}benzenesulfonamide (22-2)

10% Pd/C (200 mg) was added to a solution of 22-1 (80 mg, 0.173 mmol) in EtOAc (5 ml) at ambient temperature and the flask evacuated and backfilled with hydrogen. The resulting suspension was stirred at ambient temperature under a balloon of hydrogen for 4 hours, filtered through a pad of celite and the solvent removed in vacuo. Purification by flash chromatography on 12 g of silica, eluting with a gradient of 0-100% EtOAc in hexanes afforded 33 mg, 41% of 22-2 as a white solid.

MS (ESI): m/z=468.1768 (MH$^+$).

Example 23

SYNTHESIS of 2-(2-{2-[(4αS,5R)-1-(4-fluorophenyl)-5-hydroxy-4α-methyl-1,4,4α,5,6,7-hexahydrocyclopenta(f)indazol-5-yl]ethyl}phenyl)-N-methylacetamide

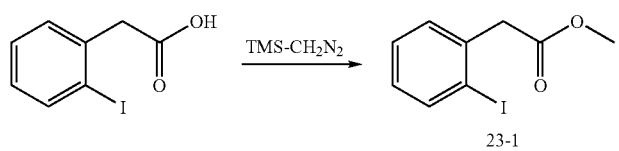

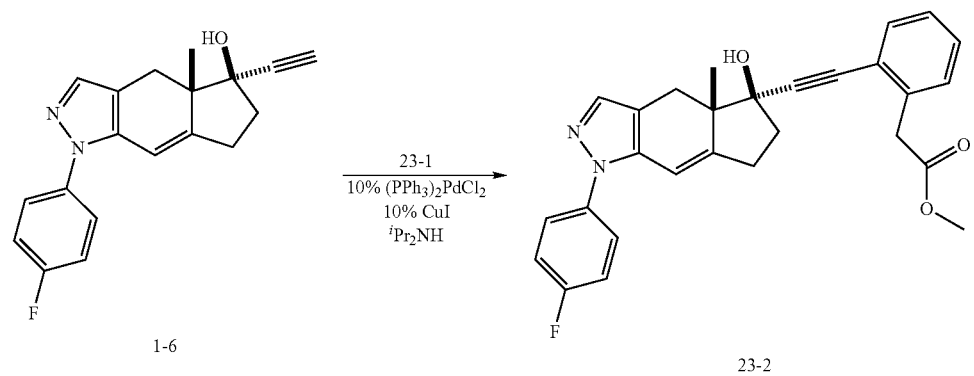

-continued

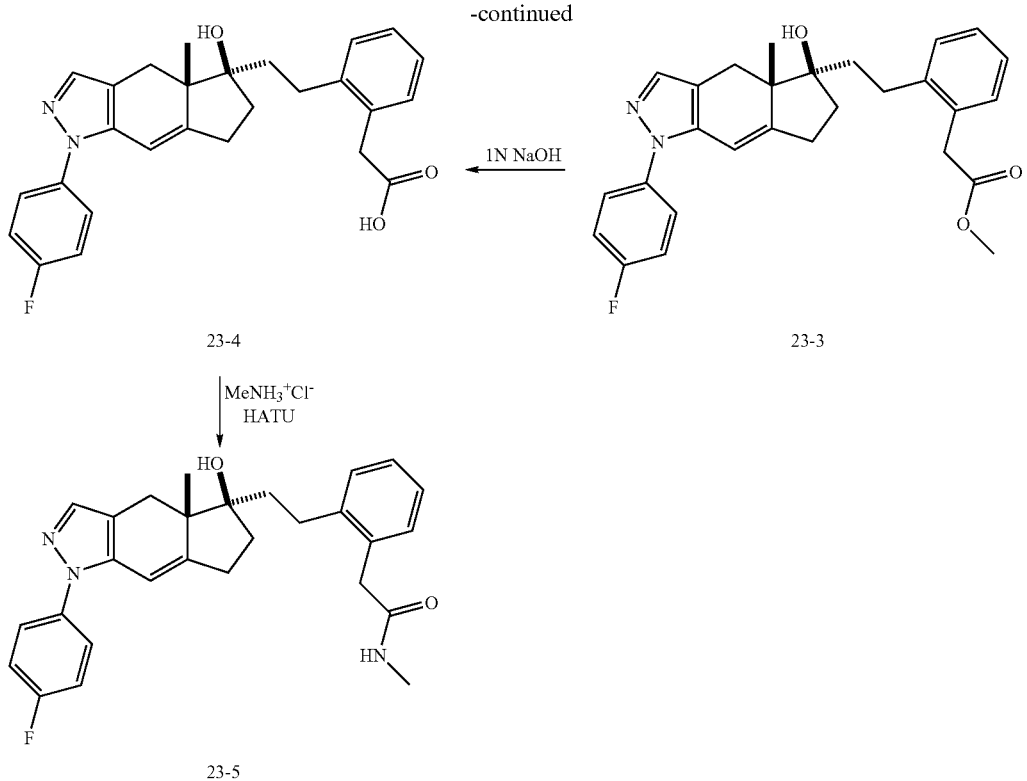

Methyl(2-iodophenyl)acetate (23-1)

Trimethylsilyl diazomethane (15.3 ml, 30.6 mmol, 2.0 M in diethyl ether) was added dropwise to a stirred, cooled 0° C. solution of (2-iodophenyl)acetic acid (4.0 g, 15.3 mmol) and MeOH (10 ml) in $CH_2Cl_2$ (50 ml) and the solution was stirred at 0° C. for 1 hour. The yellow solution was purged with nitrogen for 10 minutes. The solvent removed in vacuo and the residue was azeotroped with THF (3×25 ml) to afford 4.2 g, 100% of 23-1 as a yellow oil.

Methyl-(2-{[(4αS,5R)-1-(4-fluorophenyl)-5-hydroxy-4α-methyl-1,4,4α,5,6,7-hexahydrocyclopenta[f]indazol-5-yl]ethynyl}phenyl)acetate (23-2)

Diisopropylamine (0.693 ml, 4.86 mmol) was added to a solution of 1-6 (1.5 g, 4.86 mmol), 23-1 (2.01 g, 7.30 mmol), bis(triphenylphosphine)palladium (II) chloride (341 mg, 0.486 mmol), and CuI (9.3 mg, 0.486 mmol) in anhydrous THF (20 ml) at ambient temperature. The resulting solution was stirred at 70° C. for 2 hours, then diluted with diethyl ether, filtered through a pad of celite and the solvent removed in vacuo. Purification by flash chromatography on 120 g of silica, eluting with a gradient of 0-100% EtOAc in hexanes afforded 2.0 g, 90% of 23-2 as an orange oil.
MS (ESI): m/z=457.19 (MH$^+$).

Methyl 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetate (23-3)

10% Pd/C (3.0 g) was added to a solution of 23-2 (2.0 g, 4.38 mmol) in EtOAc (20 ml) at ambient temperature and the flask evacuated and backfilled with hydrogen. The resulting suspension was stirred at ambient temperature under a balloon of hydrogen for 1.5 hours, filtered through a pad of celite and the solvent removed in vacuo to afford 1.95 g, 97% of 23-3 as a yellow foam.
MS (ESI): m/z=461.20 (MH$^+$).

2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)acetic acid (23-4)

1M NaOH (10 ml, 10 mmol) was added to a solution of 23-3 (1.95 g, 4.23 mmol) in EtOH (20 ml) at ambient temperature. The solution was stirred at ambient temperature for 1 hour, acidified with 1N HCl and then extracted with EtOAc. The organic extract was washed with brine, dried over anhydrous MgSO$_4$, filtered and the solvent removed in vacuo to afford 1.9 g, 100% of 23-4 as a yellow solid.
MS (ESI): m/z=447.3 (MH$^+$).

2-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)-N-methylacetamide (23-5)

HATU (63.9 g, 0.168 mmol) was added to a stirred solution of 23-4 (75 mg, 0.168 mmol), methyl amine hydrochloride (17.1 mg, 0.210 mmol), 4-methylmorpholine (0.074 ml, 0.672 mmol) and DMF (1 ml). The mixture was stirred for 16 hours and then was diluted with EtOAc and washed with H$_2$O, sat NaHCO$_3$, brine, dried over anhydrous MgSO$_4$, filtered and the solvent was removed in vacuo. Purification by flash chromatography on 12 g of silica, eluting with a gradient of 0-100% EtOAc in hexanes afforded 80 mg, 60% of 23-5 as a colorless solid. MS (ESI): m/z=460.2395 (MH$^+$).

Example 107

SYNTHESIS of 2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)-acetamide 2-(2-Iodophenyl)acetamide 107-2

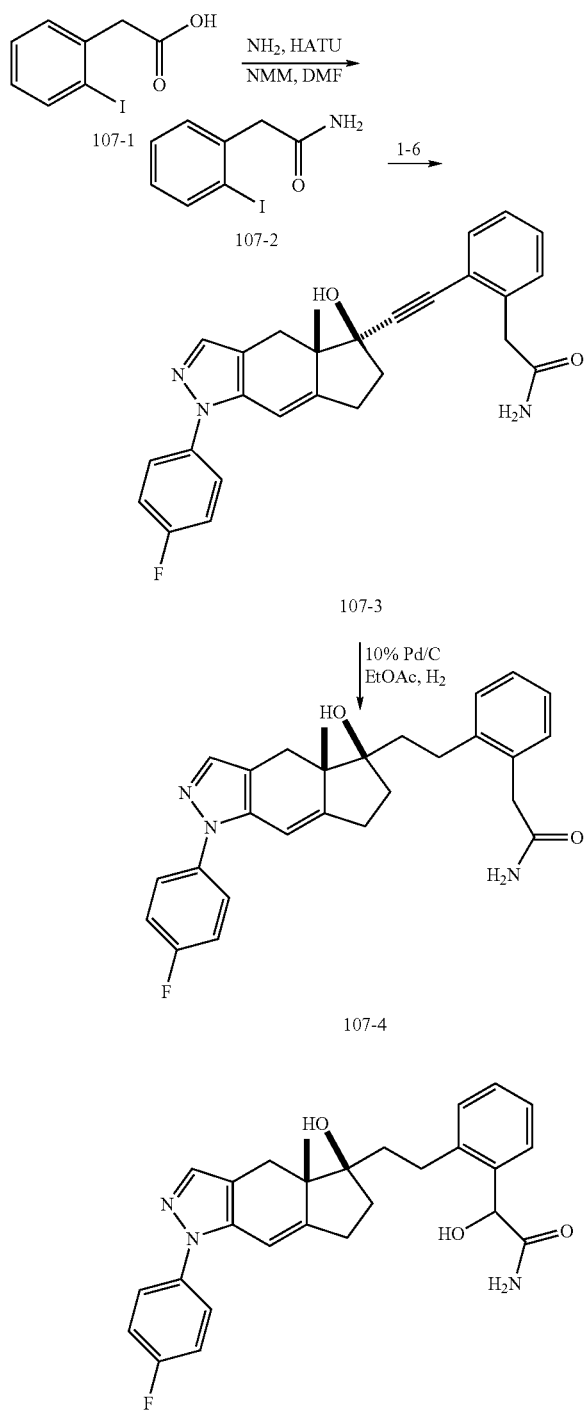

HATU (50.8 g, 134 mmol) was added to a stirred solution of 107-1 (28 g, 107 mmol), NH$_3$ (321 ml, 160 mmol, 0.5 M/dioxane), N-methylmorpholine (23.5 ml, 214 mmol) in DMF (300 ml). The mixture was stirred for 16 hours and then was diluted with EtOAc and washed with H$_2$O, sat NaHCO$_3$, brine, dried over anhydrous MgSO$_4$, filtered and ⅔ solvent was removed in vacuo. The solid was collected, washed with diethyl ether and dried in vacuo to afford 29-2 11.2 g, 40.2%) as a white solid.

$^1$H NMR (500 MHz, CDCl$_3$) δ7.88 (d, 1H, J=8 Hz), 7.36 (m, 2H), 7.00 (m, 1H), 5.38 (s, 2H), 3.75 (s, 2H).

Methyl(2-[(4αS,5R)-1-(4-fluorophenyl)-5-hydroxy-4α-methyl-1,4,4α,5,6,7-hexahydrocyclopenta(f)indazol-5-yl]ethynyl)phenyl)acetamide 107-3

A mixture of 1-6 (5.0 g, 16.22 mmol), 29-2 (5.29 g, 20.27 mmol), CuI (154 mg, 0.811 mmol) diisopropylamine (2.29 ml, 16.22 mmol) and THF (50 ml) was purged with nitrogen for 10 minutes. Bis(triphenylphosphine)palladium(II) chloride (569 mg, 0.811 mmol) was added and the resulting mixture heated to 70° C. and then stirred for 16 hours. The mixture was allowed to cool to ambient temperature and then was diluted with Et$_2$O (100 ml). The mixture was filtered through a celite pad and then the solvent removed in vacuo. Purification by flash chromatography on 330 g of silica, eluting with a gradient hexanes to 5% MeOH/EtOAc afforded 107-3 (5.0 g, 70%) as an orange oil.

MS (ESI): m/z=442.08 (MH$^+$).

2-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)-acetamide 107-4

107-3 (5 g, 11.33 mmol) was dissolved in EtOAc (50 ml) followed by addition of 10% Pd/C (4.0 g). The mixture was stirred under 1 atm H$_2$ for 3.0 hour. The mixture was filtered through a pad of celite and then the EtOAc was removed in vacuo. Purification by flash chromatography on 330 g of silica, eluting with a gradient hexanes to 2.5% MeOH/EtOAc afforded 107-4 (3.8 g, 75%) as a white solid.

HRMS (ESI): m/z=446.2236 (MH$^+$).

Example 150

SYNTHESIS of 2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)-2-hydroxypropanamide

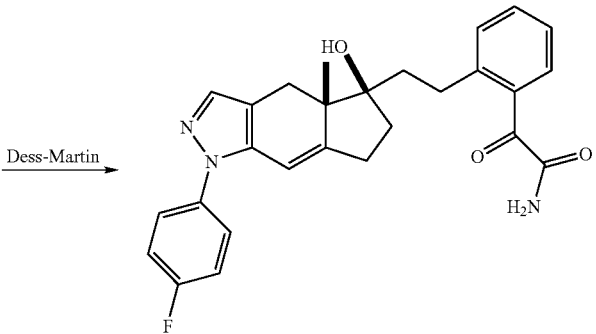

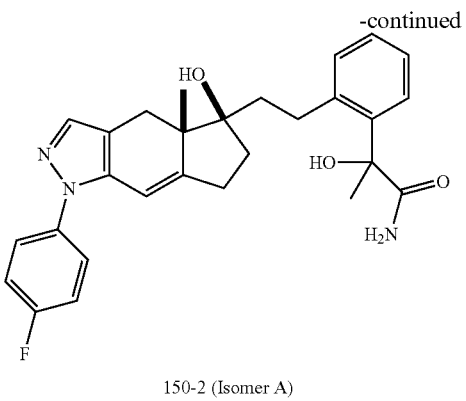

150-2 (Isomer A)

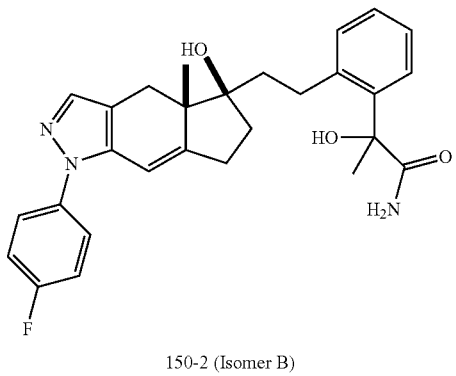

150-2 (Isomer B)

2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)-2-oxoacetamide (150-1)

A solution of 192-6(rac) (750 mg, 1.63 mmol) in $CH_2Cl_2$ (5 ml) was added to a stirred solution of Dess-Martin periodinane (758 mg, 1.79 mmol) and $CH_2Cl_2$ (10 ml). The solution was stirred for 1 hour and then was poured into a 1:1 aq solution of sat $Na_2S_2O_3$/sat $NaHCO_3$ and the mixture was stirred for 10 minutes. The aqueous portion was removed and then the organic portion was washed with brine, dried over anhydrous $MgSO_4$, filtered and the solvent was removed in vacuo. Purification by flash chromatography on 40 g of silica, eluting with a gradient of 0-100% EtOAc in hexanes afforded 150-1 (545 mg, 73%) as an orange oil.

MS (ESI): m/z=460.07 ($MH^+$).

2-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)-2-hydroxypropanamide (150-2)

A solution of methyl magnesium bromide (0.907 ml, 2.72 mmol, 3.0M diethyl ether) was added to a stirred cooled 0° C. solution of 150-1 (250 mg, 0.544 mmol) and THF (5 ml). The solution was stirred for 1 hour and then 1 M Rochelle's salt was added and the mixture was stirred for 20 minutes. The mixture was extracted with EtOAc and then the organic portion was washed with brine, dried over anhydrous $MgSO_4$, filtered and the solvent was removed in vacuo. Purification by flash chromatography on 12 g of silica, eluting with a gradient of 0-100% EtOAc in hexanes afforded the racemic mixture. Purification by preparative HPLC, 10 cm Chiracel OD, eluting with 40% IPA/hexanes 0.1% DEA afforded faster eluting 26-2 (isomer A, 110 mg, 21.2%) as a white solid and slower eluting 150-2 (isomer B, 90 mg, 17.4%) as a white solid.

Faster eluting, HRMS (ESI): m/z=476.2361 ($MH^+$).
Slower eluting, HRMS (ESI): m/z=476.2318 ($MH^+$).

Example 159

5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamideMethyl(2-iodophenyl)acetate

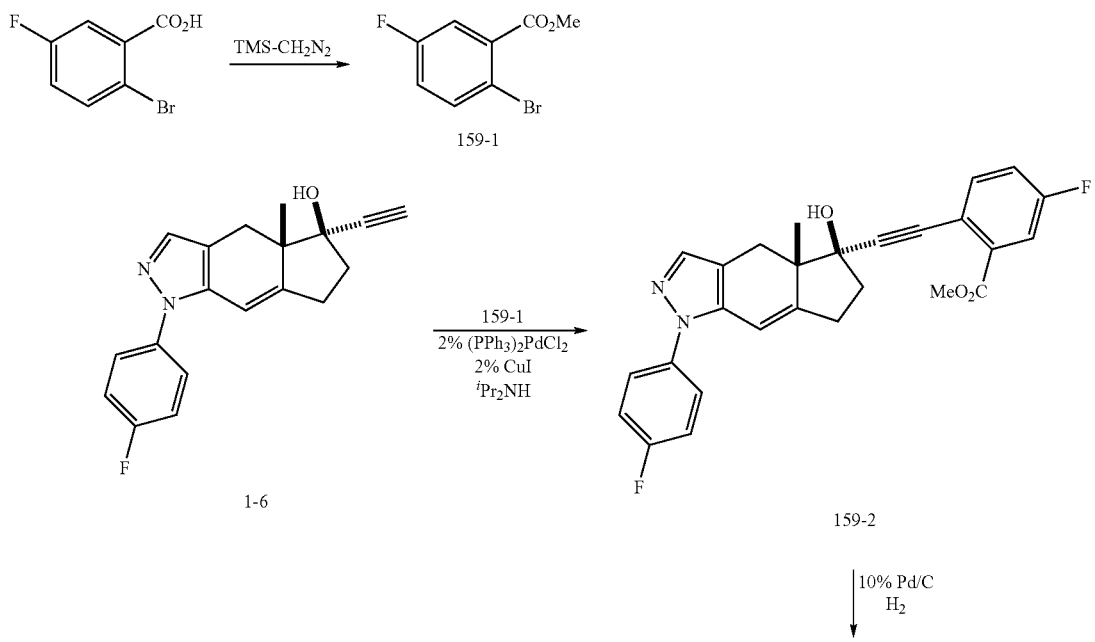

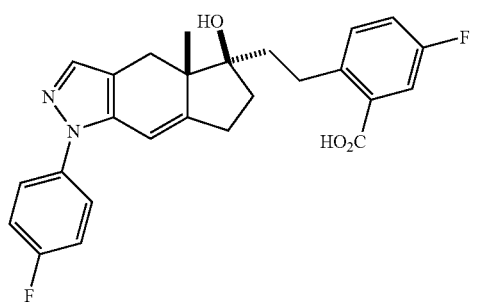

159-4

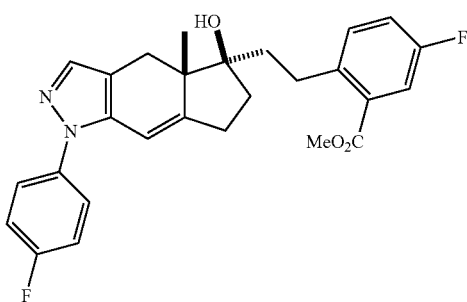

159-3

-continued

↑ 1N NaOH

| NH₃
| HATU
↓

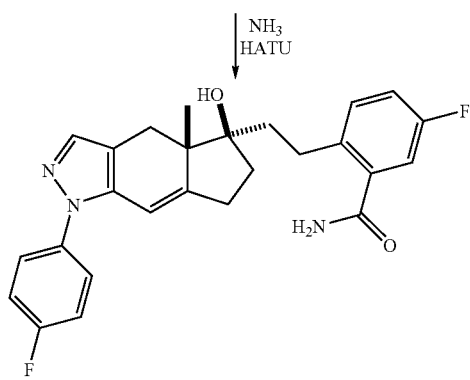

159-5

Methyl 2-bromo-5-fluorobenzoate (159-1)

Trimethylsilyl diazomethane (338 ml, 676 mmol, 2.0 M in diethyl ether) was added dropwise to a stirred, 0° C. solution of 2-bromo-5-fluorobenzoic acid (74 g, 338 mmol) in MeOH (676 ml) until a yellow color persisted. Acetic acid was added dropwise until the yellow color dissipated. The solvent was removed in vacuo, and the residue was dissolved in $CH_2Cl_2$, then filtered through a plug of silica gel, eluting with $CH_2Cl_2$. The solvent was removed in vacuo to afford 77 g, 98% of 23-1 as a yellow oil.

Methyl 5-fluoro-2-{[(4αS,5R)-1-(4-fluorophenyl)-5-hydroxy-4α-methyl-1,4,4α,5,6,7-hexahydrocyclopenta[f]indazol-5-yl]ethynyl}benzoate (159-2)

Diisopropylamine (14 ml, 97 mmol) was added to a solution of 1-6 (30 g, 97 mmol), 159-1 (27 g, 117 mmol), bis(triphenylphosphine)palladium (II) chloride (1.36 g, 1.95 mmol), and CuI (371 mg, 1.95 mmol) in anhydrous THF (354 ml) at ambient temperature. The resulting solution was stirred at 80° C. for 1 hour, then diluted with diethyl ether, filtered through a pad of celite and the solvent removed in vacuo. Purification by flash chromatography on 1.5 kg of silica, eluting with a gradient of 0-100% EtOAc in hexanes afforded 39 g, 86% of 159-2 as a white solid.

MS (ESI): m/z=461.33 (MH⁺).

Methyl 5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzoate (159-3)

10% Pd/C (17.9 g) was added to a solution of 159-2 (19.3 g, 42 mmol) in EtOAc (559 ml) at ambient temperature and the flask evacuated and backfilled with hydrogen. The resulting suspension was stirred at ambient temperature under a balloon of hydrogen for 1.5 hours, filtered through a pad of celite and the solvent removed in vacuo to afford 18.4 g, 94% of 159-3 as a white solid.

MS (ESI): m/z=465.37 (MH⁺).

5-Fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzoic acid (159-4)

1M NaOH (151 ml, 151 mmol) was added to a solution of 159-3 (35 g, 75 mmol) in EtOH (300 ml) at ambient temperature. The solution was heated at 100° C. for 1 hour, acidified with 1N HCl and then extracted with EtOAc. The organic extract was washed with brine, dried over anhydrous MgSO₄, filtered and the solvent removed in vacuo to afford 37 g, 100% of 159-4 as a white solid.

MS (ESI): m/z=451.10 (MH⁺).

5-Fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide (159-5)

A solution of ammonia in dioxane (0.5 M, 244 ml, 122 mmol), followed by HATU (31 g, 81 mmol) was added to a stirred solution of 159-4 (36.7 g, 81 mmol) and Hunigs base (43 ml, 244 mmol) in DMF (407 ml). The mixture was stirred for 1 hour, then was diluted with EtOAc and washed with sat NaHCO₃, brine, dried over anhydrous MgSO₄, filtered and the solvent was removed in vacuo. Purification by flash chromatography on 1.5 kg of silica, eluting with a gradient of 0-100% CHCl₃ to CHCl₃/EtOAc/MeOH (70:20:10) afforded 28 g, 76% of 159-5 as a white solid. The compound was dissolved in a minimal amount of boiling EtOAc, then allowed to cool slowly to ambient temperature to afford 14 g of crystalline material.

MS (ESI): m/z=450.1998 (MH⁺).

Alternate Example 159

1. Alkyne Addition

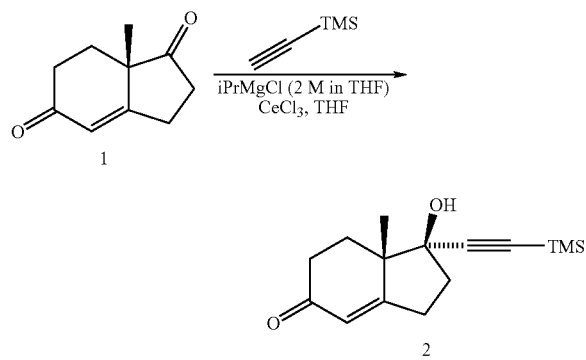

| substrate | MW | amount | mmol | equiv |
|---|---|---|---|---|
| 1 | 164 | 15 g | 91.46 | 1.0 |
| TMS alkyne | 98 | 13 g | 132.62 | 1.45 |
| iPrMgCl (1.8 M in THF) | | 71.14 mL | 128.05 | 1.4 |
| CeCl3 | 246 | 31.6 g | 128.05 | 1.4 |
| THF | | 50 + 150 + 45 mL | | |

To a round bottom flask with overhead stirring, $N_2$ inlet, thermocouple, and reflux condenser is added THF (150 mL) and anhydrous $CeCl_3$ and the resulting slurry was heated to 50° C. for 4 hr then 15 h at RT after which the flask is cooled to an internal temperature of −65° C. with a MeOH/dry ice bath.

Meanwhile, in a separate flask equipped with overhead stirring, $N_2$ inlet, and thermocouple was added THF (50 mL) and TMS alkyne and the resulting solution was cooled to an internal temperature of −5° C. iPrMgCl (1.8M in THF) is then added portionwise, while maintaining the internal temperature below 5° C. Once all the iPrMgCl is added (1.5 hr addition time), the reaction vessel is allowed to warm to room temperature and aged for 2 hr. After 2 hr, the newly formed alkyne-MgCl is cooled to 10° C. and added to the CeCl3 solution that has been previously cooled to −65° C., keeping the internal temperature below −50° C. Once all the alkyne-MgCl is added, the solution is aged for 1.5 hr at −60° C. Next, the ketone in THF (45 mL) is added via an addition funnel at −60° C. keeping the internal temperature below −50° C. Once all the ketone is added, the reaction is monitored with HPLC.

When the reaction is complete, as judged by HPLC conversion of 1, AcOH (2 mol equiv) is added (exothermic) at −50° C. and warmed to room temperature followed by addition of 30 mL of water.

The biphasic solution is then transferred to a 200 L extraction vessel containing water (30 mL) and MTBE (300 mL). After 20 min of agitation, the aqueous layer is cut and extracted with 100 mL of MTBE. The aqueous layer is cut again, checked for losses, and discarded. The combined organic layers are washed with 30 mL of fresh water then brine (30 mL), then concentrated and solvent switched to heptane to give the final composition of 1:15 of MTBE:heptane at 8-10 vol total. The resulting slurry is then aged at RT for overnight and filtered and the wetcake is washed with heptane and dried under a $N_2$ sweep. Isolated 18.5 g of the desired product (77% yield).

2. Pyrrazole Formation

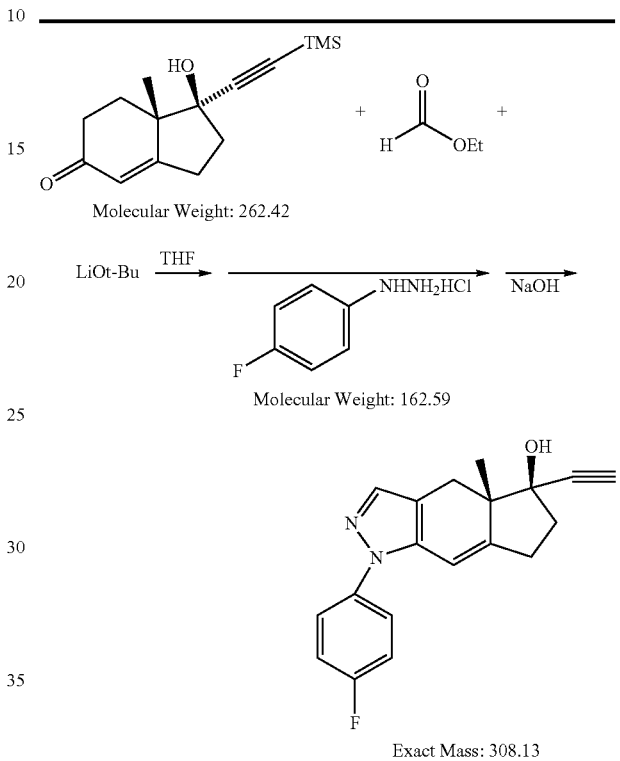

| Materials | MW | Amount | MMoles | Eq |
|---|---|---|---|---|
| Ketone SM | 260 | 11 g | 41.9 | 1.0 |
| Ethyl formate | 74 | 9.4 g | 127 | 3.0 |
| Li Ot-But | 80 | 17 g | 211 | 5.0 |
| THF | | 220 mL + 50 mL | | |
| AcOH | 60 | 25.4 g | 423 | 10 |
| MeOH | | 250 mL | | |
| p-F-phenylhydrazine HCl salt | 162.6 | 8.24 g | 51 | 1.2 |

To a freshly prepared slurry of LitOBu in THF (220 mL) at 5° C. is added a solution of the enone and ethyl formate in 20 mL of THF over 10 min. After aging at 5-10° C. for 3 h, >95% conversion is typically observed, at which point a solution of AcOH in THF (25 mL) is added slowly over 10 min, while maintaining the temperature below 25° C. During this addition, solids form almost immediately and the batch thickens momentarily but becomes more fluid with stirring. At the end of AcOH quench, 25 mL of MeOH is then added, followed by p-F phenylhydrazine HCl salt as a solid. The reaction mixture is then heated to 60° C., aged for 1 h to give a full conversion, diluted with MTBE (110 mL) and washed with 10% aqueous NaCl (110 mL). The organic layer is separated and washed one more time with 10% aqueous NaCl (100 mL). Removal of the TMS group is carried out by first diluting the organic layer with 23 mL of MeOH and 23 mL of $H_2O$, followed by 42 mL of 10M NaOH to bring the pH to >13. After aging at 35-50° C. for 1-2 h, the reaction is found complete and the batch is cooled to 25° C., washed with 110 mL of 10% aqueous brine and the organic layer is washed one more time with 170 mL of 10% aqueous brine. The organic layer is then dried over $Na_2SO_4$ (20 g) overnight, filtered and then batch concentrated under vacuum to minimum volume (about 30 mL) using 160-200 mL of acetonitrile. Product crystallized out at this point and to this slurry is added 40 mL MTBE and then 450 L heptane over 30 min at. 23° C. After stirring for 35 min, reaction mixture is then concentrated under vacuum to remove about 20 mL of solvent. The batch is then stirred for 45 min, filtered and the wet cake is washed with 20 mL of 2:1 MTBE:heptane and air dried. The product is obtained as a brown solid in 9.1 grams (70%).

3. Coupling

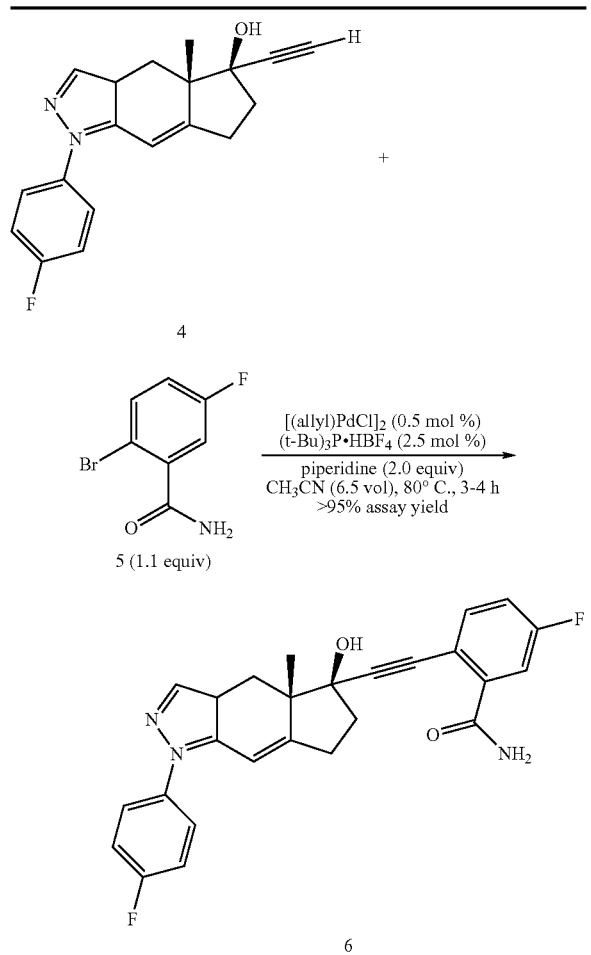

| Line | Reagent | FW | Amount | mMoles |
|---|---|---|---|---|
| 1 | Alkyne 4 | 308.35 | 9.87 gA | 32.0 |
| 2 | Bromide 5 | 218.02 | 7.67 g | 35.2 |
| 3 | Piperdine | 85.15 | 6.39 mL | 64.0 |
| 4 | [(allyl)PdCl]$_2$ | 365.89 | 58.8 mgA | 0.160 |
| 5 | (t-Bu)$_3$P•HBF$_4$ | 290.13 | 232 mgA | 0.800 |
| 6 | CH$_3$CN | 41.05 | 50 mL | |
| 8 | Toluene | 92.14 | 100 mL | |

Alkyne 4, bromide 5, acetonitrile (RM Table, line 6), and piperidine are charged successively to a round bottom flask equipped with a thermocouple, stir bar, and reflux condenser. The reagents are stirred until a reddish-brown solution is formed and the solution is degassed by 5 vacuum and nitrogen refill cycles. The phosphine ligand and palladium catalyst are then added successively and the resulting solution is degassed again. The solution is then heated to 80° C. and aged until a 99% conversion by HPLC analysis is achieved (typically 1 h). The solution is diluted with 100 mL of toluene and is then washed successively with HOAc (1.5 equiv) in 15 wt % aqueous NaCl (48 mL), saturated KHCO3 solution (40 mL), and saturated NaCl solution (40 mL). Ecosorb 941 (2.53 g) and trithiocyanuric acid (127 mg) are added to the solution and the solution was stirred between 23-25° C. for 1 hour. The black slurry is then filtered over Solka flock (10 g) through a 15-20 micron fritted funnel. The wet cake is washed with 130 mL of 2:1 toluene:CH$_3$CN. The solution is transferred to a separatory funnel and washed with 15 wt % K$_2$CO$_3$ aqueous solution (38 mL) and then diluted with toluene (26.7 mL) and CH$_3$CN (53 mL). The organic layer is washed with saturated aqueous NaCl (38 mL) and transferred to a round bottom flask. The organic layer is assayed to contain 12.76 gA of product 6 by HPLC analysis.

4. Crystallization of Coupling Product

The crude solution of 6 (12.6 g) in PhMe/MeCN is concentrated under reduced pressure to remove MeCN, while maintaining the total volume of 10 vol and the batch temperature at 20-25° C. Total of 6-vol of PhMe is used during this process. At the end of the solvent switch, the resulting slurry is heated up to 90° C. and cooled slowly to 72° C. After appropriate seeding, the product started to crystallize to give a slurry which is then aged overnight. Heptane (3.3 vol) is then added and the resulting mixture is aged until 6-8% of product remained in the mother liquor. At this point, the slurry is then filtered and the wetcake is washed with cold PhMe/Heptane (3/1, 6 vol) followed by heptane (3 vol) and dried under stream of N$_2$ overnight.

The product is isolated as pale yellow solid in 13.67 g (84.4 wt %) in 92% recovery or 81% overall yield.

5. Bromo Benzamide Preparation

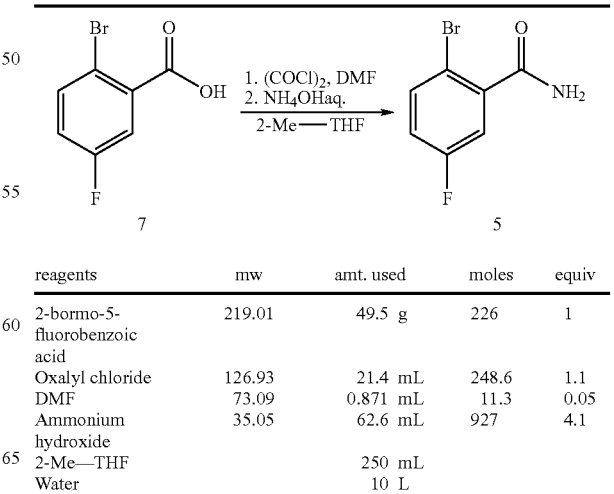

| reagents | mw | amt. used | moles | equiv |
|---|---|---|---|---|
| 2-bormo-5-fluorobenzoic acid | 219.01 | 49.5 g | 226 | 1 |
| Oxalyl chloride | 126.93 | 21.4 mL | 248.6 | 1.1 |
| DMF | 73.09 | 0.871 mL | 11.3 | 0.05 |
| Ammonium hydroxide | 35.05 | 62.6 mL | 927 | 4.1 |
| 2-Me—THF | | 250 mL | | |
| Water | | 10 L | | |

-continued

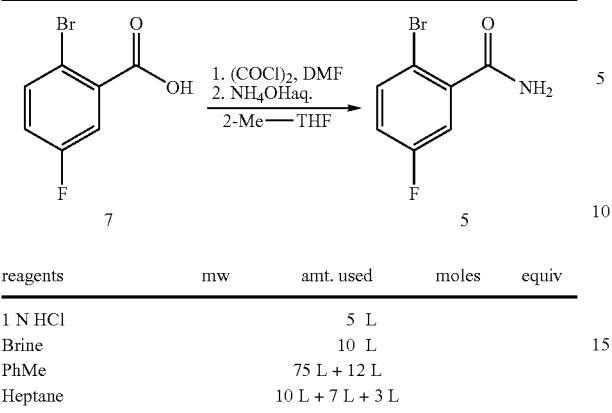

| reagents | mw | amt. used | moles | equiv |
|---|---|---|---|---|
| 1 N HCl | | 5 L | | |
| Brine | | 10 L | | |
| PhMe | | 75 L + 12 L | | |
| Heptane | | 10 L + 7 L + 3 L | | |

To a RB flask equipped with an addition funnel is charged acid 7, 2-Me-THF and DMF. The solution is then cooled to 7° C. and oxalyl chloride is added dropwise over 30 min at <15° C. After the addition is complete, the reaction mixture is warmed to rt and aged for 45 min. Upon complete consumption of the acid, the reaction mixture is then charged dropwise into another flask containing cold (9° C.) mixture of concentrated NH$_4$OH and 2-Me-THF over 1.5 h, while maintaining the temperature around 20-25° C. To the reaction mixture is added water (100 mL) to dissolve some solids and the resulting biphasic layer is transferred to a separatory funnel. The aqueous layer is separated and the organic layer is washed with 1 N HCl (50 mL) and with brine (100 mL). The final organic layer is then solvent switched to toluene to give a final slurry concentration of 15 vol. The slurry is then heated to 110° C. to get a clear solution, which is then cooled slowly to RT. Crystallization is typically observed to occur at 100° C. and after aging at rt overnight, heptane (10 vol) is then added, followed by a 1 h of age. The suspension is then filtered and the wet cake is washed with cold 1:1 heptane:toluene and dried under a stream of N$_2$ to give the product in 46.9 g (94.7%).

6. Hydrogenation-Final Crystallization

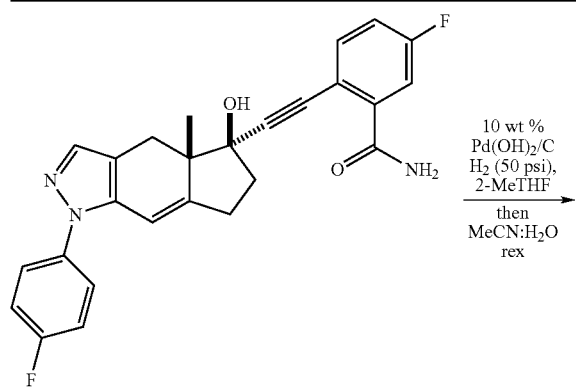

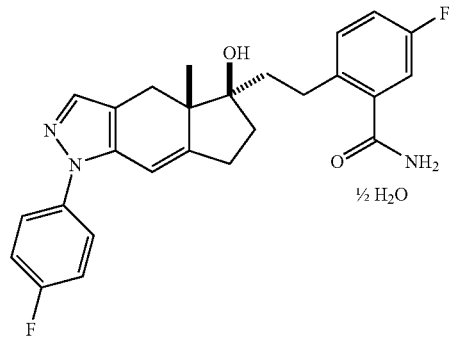

EXAMPLE 159

Hemihydrate form

| Compounds | Amount/MW | Mmol/eq |
|---|---|---|
| Alkyne 6 | 4.86 g/445.46 | 10.91/1.0 |
| Wet 20% Pd(OH)$_2$/C | 56.9 g/140.43 | 0.56/0.06 |
| Hydrogen (H$_2$) | 1 atm | 21.82/2.0 |
| 2-MeTHF | 24 mL | 5 vol |
| THF | 24 mL | 5 vol |
| Solka Floc | 425 g | 75 wt % |
| Ecosorb C941 | 114 g | 20 wt % |
| MP-TMT | 46 g | 5 wt % |
| SiO$_2$ gel | 460 g | 50 wt % |
| MeCN | ~41-42 L | |
| H$_2$O | 26 L | |

A mixture of alkyne 6 and wet 20 wt % Pd(OH)$_2$/C in 2-MeTHF (5 vol) is exposed to 1 atm of H$_2$ for 6 hours, at which a complete consumption of starting is typically observed. The slurry is then diluted with THF (8 vol) and the resulting solution is filtered through Solka Floc (75 wt %) and rinsed with more THF (10 vol). The combined filtrate is filtered through a 1 micron inline filter into a round bottom flask and treated with 20 wt % Ecosorb C941 and 5 wt % MP-TMT and aged with rigorous stirring at 25° C. for 6 hours. The slurry is then filtered through 50 wt % SiO$_2$ gel, rinsed with 10 vol of THF and the combined filtrate is then solvent switched to MeCN to give a final slurry concentration of 13 vol. The slurry is then heated to 75° C., at which a clear yellowish solution is obtained, cooled to 72° C., seeded with 4% seeds and allowed to cool to 30° C. over 5-8 hours and aged for additional 8 hours. Water (8 vol) is then added over 3 hours, while maintaining the temperature between 28-30° C. At the end of addition, the resulting slurry is allowed to cool to 4° C. over 1-2 h, aged for additional 1 h, filtered and the wet cake is washed with cold 1:1 mixture of MeCN:H$_2$O. After drying at rt under a stream of N$_2$, 4.25 g of the product is isolated as white solid (87% yield).

Example 192
SYNTHESIS of 2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)-2-hydroxyacetamide
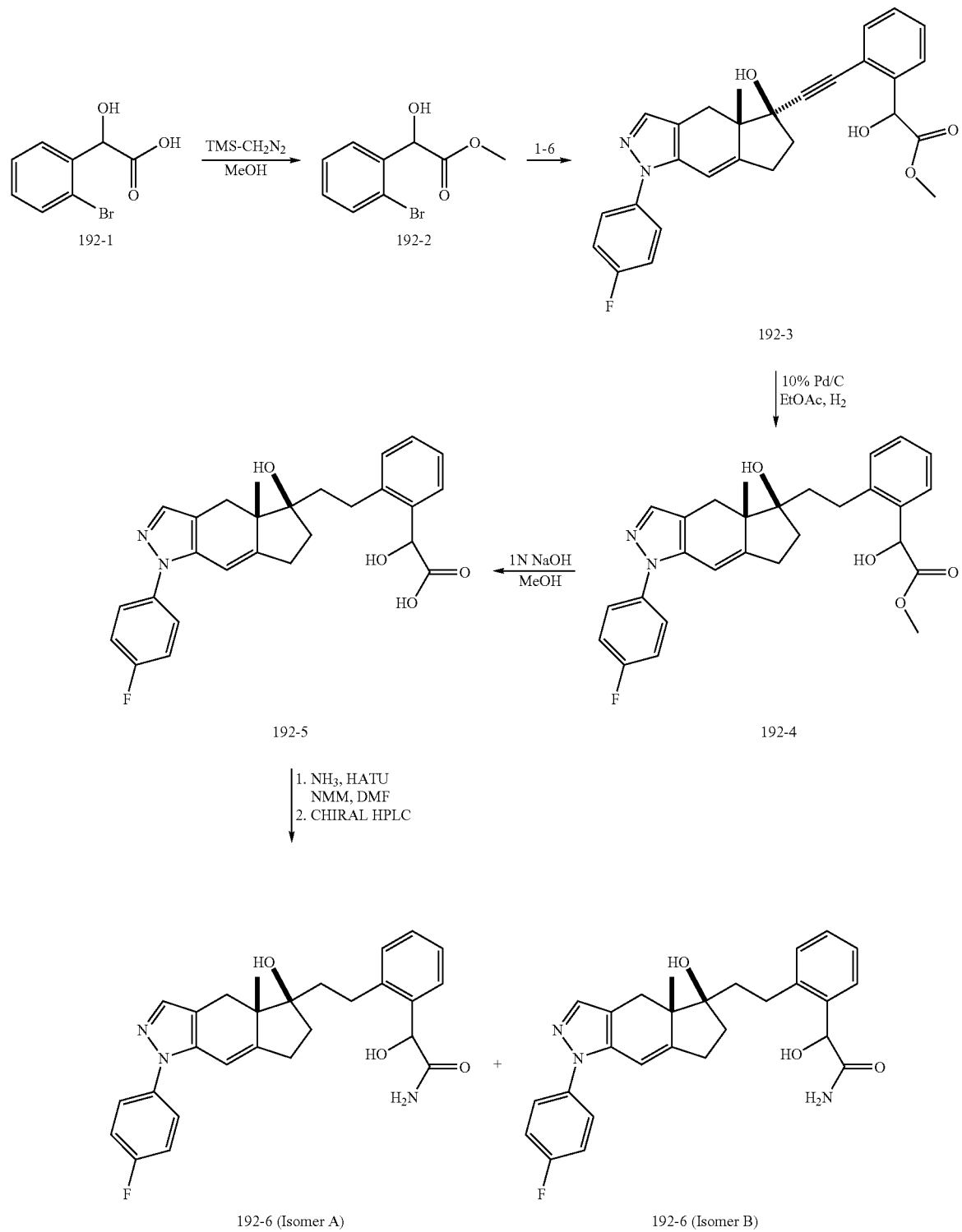

Methyl(2-bromophenyl)hydroxy acetate (192-2)

A solution of 2 M trimethylsilyldiazomethane in diethyl ether (108 ml, 216 mmol) was added to a stirred, cooled 0° C. solution of 192-1 (25 g, 108 mmol) in CH$_2$Cl$_2$ (250 mL) and MeOH (50 ml) and the solution was stirred for 60 minutes. Nitrogen was bubbled through the solution for 10 minutes. The solvent was removed in vacuo and the residue was azeotroped with THF (3×25 ml) to afford 192-2 (25.5 g, 96%) as a yellow oil.

$^1$H NMR (500 MHz, CDCl$_3$) δ 7.58 (d, 1H, J=7 Hz), 7.38 (m, 1H), 7.34 (m, 1H), 7.21 (m, 1H), 5.59 (d, 1H, J=5 Hz), 3.78 (s, 3H), 3.55 (m, 1H).

Methyl(2-[(4αS,5R)-1-(4-fluorophenyl)-5-hydroxy-4α-methyl-1,4,4α,5,6,7-hexahydrocyclopenta(f)indazol-5-yl]ethynyl)phenyl)(hydroxy)acetate (192-3)

A mixture of 1-6 (10 g, 32.4 mmol), 192-2 (8.74 g, 35.7 mmol), CuI (309 mg, 1.62 mmol) and diisopropylamine (100 ml, 701 mmol) was purged with nitrogen for 10 minutes. Tetrakis(triphenylphosphine)palladium (1.87 g, 1.622 mmol) was added and the resulting mixture heated to 90° C. and then stirred for 3 hours. The mixture was allowed to cool to ambient temperature and then was diluted with EtOAc (100 ml). The mixture was filtered and the solvent removed in vacuo. Purification by flash chromatography on 330 g of silica, eluting with a gradient of 0-100% EtOAc in hexanes afforded 192-3 (12 g, 78%) as an orange oil.

MS (ESI): m/z=472.87 (MH$^+$).

Methyl(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)(hydroxy)acetate (192-4)

192-3 (12 g, 25.4 mmol) was dissolved in EtOAc (120 ml) and then added 10% Pd/C (6.0 g). The mixture was stirred under 1 atm H$_2$ for 1.0 hour. The mixture was filtered through a pad of celite and then the EtOAc was removed in vacuo to afford 192-4 (11 g, 91%) as a yellow oil.

MS (ESI): m/z=476.96 (MH$^+$).

(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)(hydroxy)acetic acid (192-5)

A solution of 1N NaOH (50 ml, 50 mmol) was added to a stirred solution of 192-4 (11 g, 23.08 mmol) in MeOH (120 ml) and the solution was stirred for 60 minutes. The solution was acidified with 1N HCl and then the MeOH was removed in vacuo. The residue was extracted with EtOAc and the organic portion was washed with brine, dried over anhydrous MgSO$_4$, filtered and the solvent was removed in vacuo to afford 192-5 (10.5 g, 98%) as a white solid.

MS (ESI): m/z=463.01 (MH$^+$).

2-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)-2-hydroxyacetamide (192-6)

HATU (4.93 g, 12.94 mmol) was added to a stirred solution of 192-5 (5.0 g, 10.81 mmol), NH$_3$ (32.4 ml, 16.22 mmol, 0.5 M/dioxane), N-methylmorpholine (4.75 ml, 43.2 mmol) in DMF (100 ml). The mixture was stirred for 16 hours and then was diluted with EtOAc and washed with H$_2$O, sat NaHCO$_3$, brine, dried over anhydrous MgSO$_4$, filtered and the solvent was removed in vacuo to afford the racemic mixture. Purification by preparative HPLC, 10 cm Chiracel AD, 2 injections, eluting with 30% IPA/hexanes 0.1% DEA afforded faster eluting 192-6 (isomer A, 1.0 g, 20.0%) as an orange solid and slower eluting 192-6 (isomer B, 2.3 g, 46%) as an orange solid.

Faster eluting, HRMS (ESI): m/z=462.2192 (MH$^+$).
Slower eluting, HRMS (ESI): m/z=462.2196 (MH$^+$).

Example 194

SYNTHESIS of 2-(2-Fluoro-6-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetamide

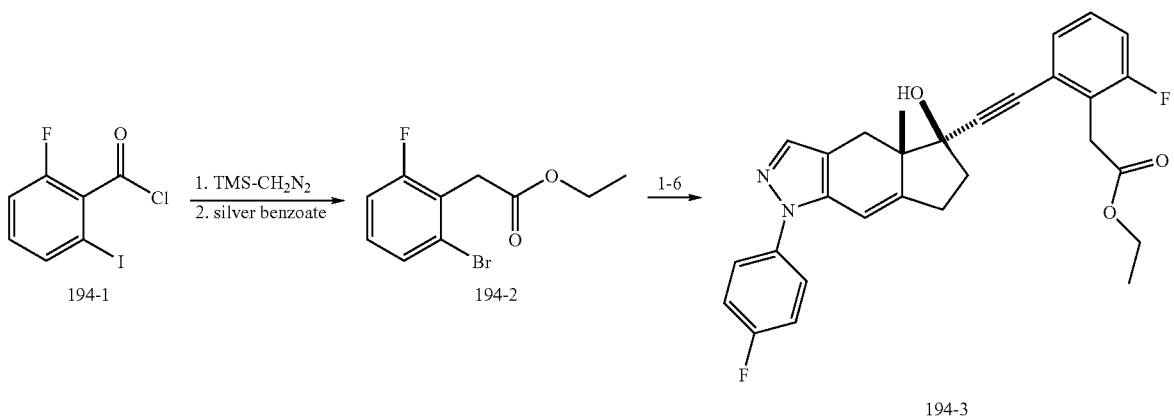

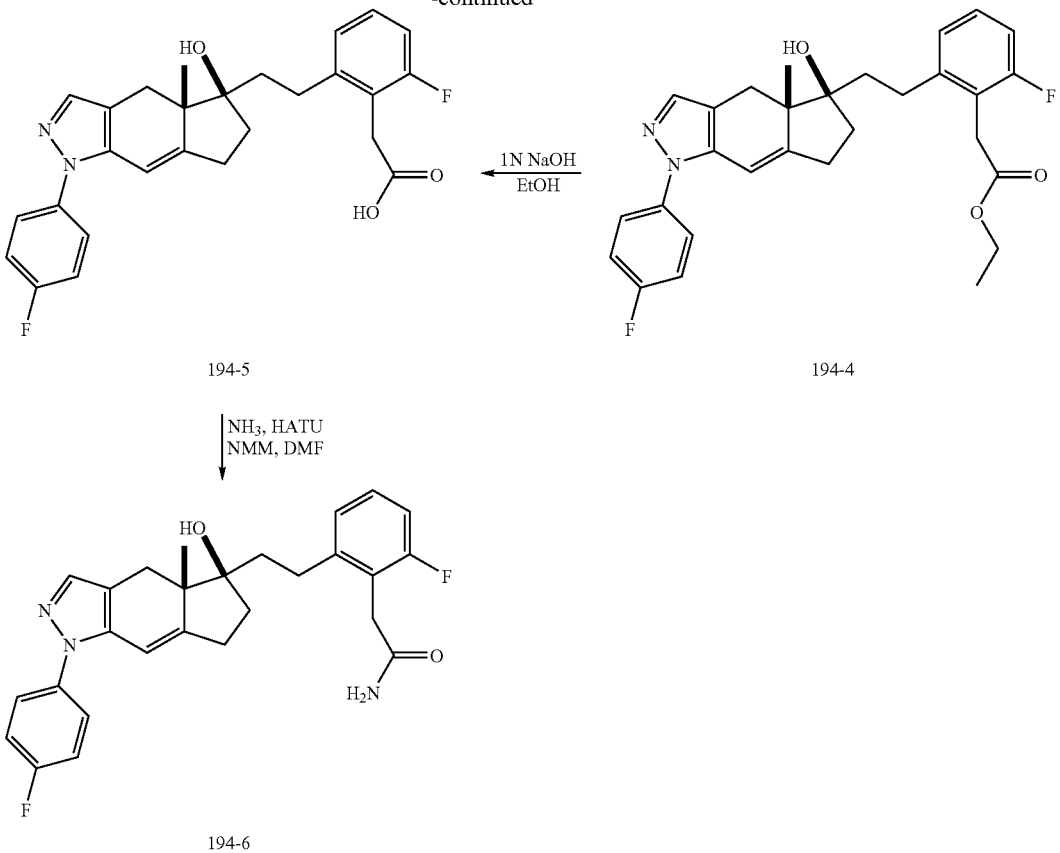

Ethyl(2-bromo-6-fluorophenyl)acetate (194-2)

194-1 (25 g, 88 mmol) was added to a stirred, cooled 0° C. solution trimethylsilyldiazomethane (65.9 ml, 132 mmol, 2M diethyl ether) and NEt$_3$ (18.37 ml, 132 mmol) in 1:1 THF/CH$_3$CN (200 mL) and the solution was kept at 0° C. for 16 hours. Nitrogen was bubbled through the solution for 10 minutes. The solvent was removed in vacuo and the residue was azeotroped with THF (3×25 mL). The residue was dissolved in EtOAc and then washed with H$_2$O, 0.1 N HCl, brine, dried over anhydrous MgSO$_4$ and the solvent removed in vacuo. The residue was dissolved in EtOH (100 ml) and then was treated with NEt3 (14.7 ml, 105.6 mmol) and silver benzoate (3.95 g, 13.2 mmol). The mixture was heated to 80° C. for 10 minutes and then allowed to cool to ambient temperature. The mixture was filtered and then the solvent was removed in vacuo. Purification by flash chromatography on 330 g of silica, eluting with a gradient of 0-20% EtOAc in hexanes afforded 194-2 (20 g, 73.6%) as a colorless oil.

$^1$H NMR (500 MHz, CDCl$_3$) δ 7.63 (d, 1H, 8 Hz), 7.07 (t, 1H, J=9 Hz), 6.99 (m, 1H), 4.19 (m, 2H), 3.87 (s, 2H), 1.27 (t, 3H, J=7 Hz).

Ethyl(2-Fluoro-6-([(4αS,5R)-1-(4-fluorophenyl)-5-hydroxy-4α-methyl-1,4,4α,5,6,7-hexahydrocyclopenta(f)indazol-5-yl]ethynyl)phenyl)acetate (194-3)

A mixture of 1-6 (4.0 g, 12.97 mmol), 194-2 (4.80 g, 15.57 mmol), CuI (247 mg, 1.30 mmol) diisopropylamine (2.02 ml, 14.27 mmol) and THF (30 ml) was purged with nitrogen for 10 minutes. Bis(triphenylphosphine)palladium(II) chloride (911 mg, 1.30 mmol) was added and the resulting mixture heated to 70° C. and then stirred for 16 hours. The mixture was allowed to cool to ambient temperature and then was diluted with Et$_2$O (100 ml). The mixture was filtered through a celite pad and then the solvent removed in vacuo. Purification by flash chromatography on 330 g of silica, eluting with a gradient of 0-100% EtOAc in hexanes afforded 194-3 (5.5 g, 87%) as an orange oil.

MS (ESI): m/z=488.87 (MH$^+$).

Ethyl(2-fluoro-6-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetate (194-4)

194-3 (5.5 g, 11.26 mmol) was dissolved in EtOAc (50 ml) and then added 10% Pd/C (5.0 g). The mixture was stirred under 1 atm H$_2$ for 3.0 hours. The mixture was filtered through a pad of celite and then the EtOAc was removed in vacuo to afford 194-4 (5.2 g, 94%) as a yellow foam.

MS (ESI): m/z=493.06 (MH$^+$).

(2-Fluoro-6-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetic acid (194-5)

A solution of 1N NaOH (25 ml, 25 mmol) was added to a stirred solution of 194-4 (5.2 g, 10.56 mmol) in EtOH (50 ml) and the solution was stirred for 2 hours. The solution was acidified with 1N HCl and then extracted with EtOAc. The organic portion was washed with brine, dried over anhydrous MgSO$_4$, filtered and the solvent was removed in vacuo to afford 194-5 (4.75 g, 97%) as a white solid MS (ESI): m/z=465.00 (MH$^+$).

2-(2-Fluoro-6-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetamide (194-6)

HATU (4.42 g, 11.63 mmol) was added to a stirred solution of 194-5 (4.5 g, 9.69 mmol), NH₃ (38.8 ml, 19.38 mmol, 0.5 M/dioxane), N-methylmorpholine (4.26 ml, 38.8 mmol) in DMF (100 ml). The mixture was stirred for 16 hours and then was diluted with EtOAc and washed with H₂O, sat NaHCO₃, brine, dried over anhydrous MgSO₄, filtered and the solvent was removed in vacuo. Purification by flash chromatography on 330 g of silica, eluting with a gradient of hexanes to 5% MeOH/EtOAc afforded 194-6 (3.3 g, 73.5%) as an orange oil.

HRMS (ESI): m/z=464.2150 (MH⁺).

Example 196

SYNTHESIS of 2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)propanamide

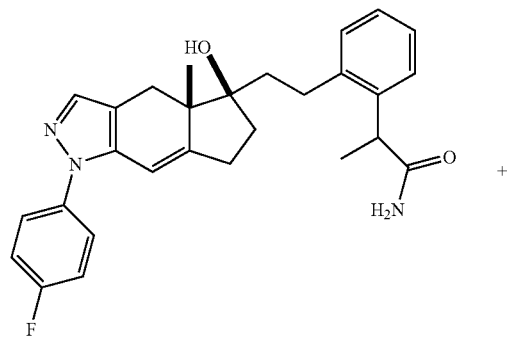

196-1 (Isomer A)

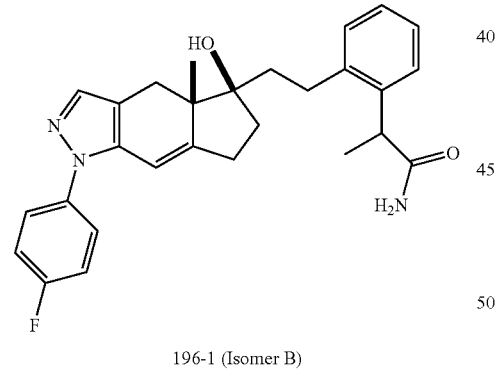

196-1 (Isomer B)

2-(2-(2-[(4αS,5R)-1-(4-Fluorophenyl)-5-hydroxy-4α-methyl-1,4,4α,5,6,7-hexahydrocyclopenta(f)indazol-5-yl]ethyl)phenyl)propanamide (196-1)

Compounds 196-1 were synthesized in accord with the general procedure outlined in Example 192. For the preparation of 2-(iodophenyl)propanoic acid see reference:

Journal of the American Chemical Society, 93, 19, 4845-4850, (1971).

Faster eluting, HRMS (ESI): m/z=460.2373 (MH⁺).
Slower eluting, HRMS (ESI): m/z=460.2372 (MH⁺).

Example 198

SYNTHESIS of 2-Fluoro-2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetamide

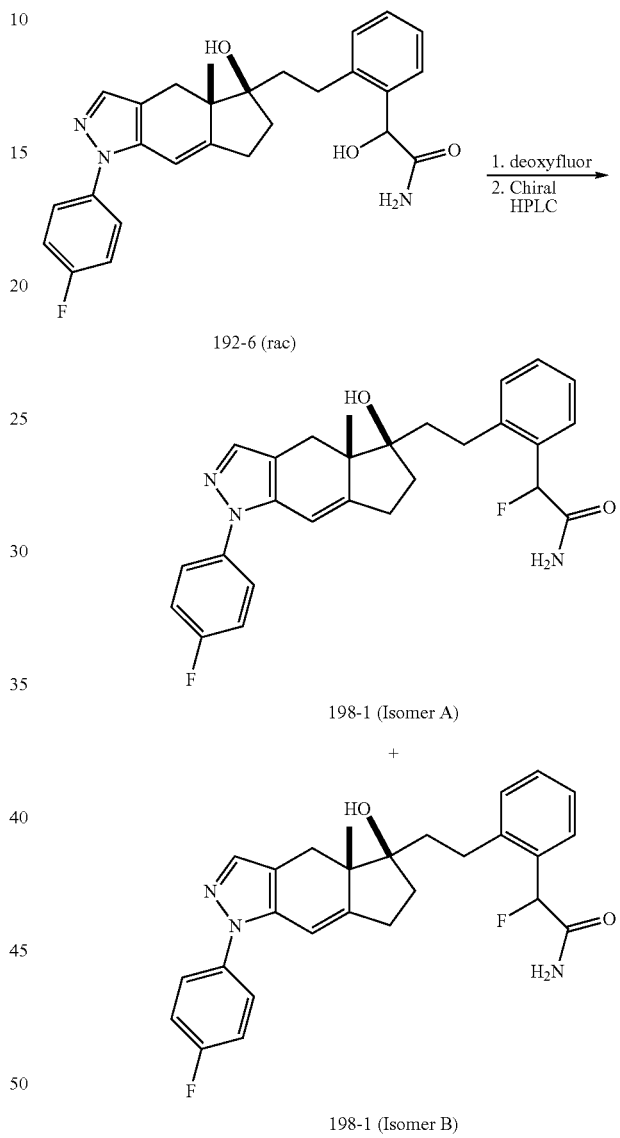

2-Fluoro-2-(2-(2-[(4αS,5R)-1-(4-fluorophenyl)-5-hydroxy-4α-methyl-1,4,4α,5,6,7-hexahydrocyclopenta(f)indazol-5-yl]ethyl)phenyl)acetamide (198-1)

192-6(rac) (250 mg, 0.542 mmol) in CH₂Cl₂ (2 ml) was added to a stirred cooled −78° C. solution of [Bis(1-methoxyethyl)-amino]sulfur trifluoride (0.150 ml, 0.813 mmol) and CH₂Cl₂ (3 ml). The solution was stirred for 3 hours and then sat. NaHCO₃ was added and the mixture was warmed to ambient temperature. The mixture was extracted with EtOAc and then the organic portion was washed with brine, dried over anhydrous MgSO₄, filtered and the solvent was removed in vacuo. Purification by flash chromatography on 40 g of silica, eluting with a gradient of 0-100% EtOAc in hexanes afforded the racemic mixture. Purification by preparative HPLC, 2 runs, 5 cm Chiracel AD, eluting with 40% IPA/hexanes 0.1% DEA afforded faster eluting 198-1 (Isomer A, 60 mg, 23.9%) as a colorless foam and slower eluting 198-1 (Isomer B, 40 mg, 15.9%) as a colorless foam.

Faster eluting, HRMS (ESI): m/z=464.2122 (MH$^+$).
Slower eluting, HRMS (ESI): m/z=464.2117 (MH$^+$).

The following examples were prepared following the general synthetic scheme and procedures analogous to the examples described above.

| Ex. | STRUCTURE | NAME | M + 1 |
|---|---|---|---|
| 2 | 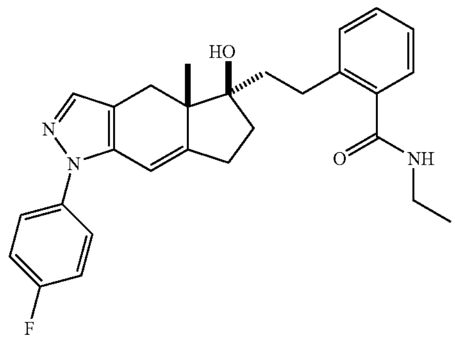 | N-ethyl-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 460.2395 |
| 5 | 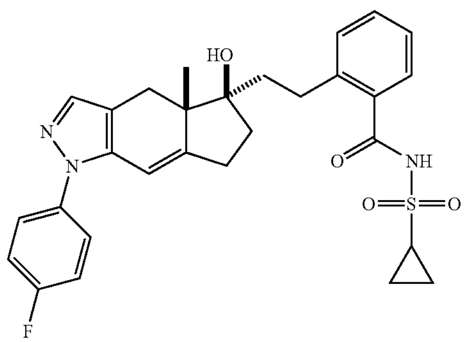 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)cyclopropanesulfonamide | 522.2230 |
| 10 | 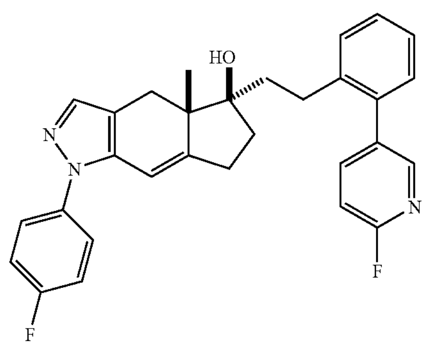 | (4αS,5R)-1-(4-fluorophenyl)-5-{2-[2-(6-fluoropyridin-3-yl)phenyl]ethyl}-4α-methyl-1,4,4α,5,6,7-hexahydrocyclopenta[f]indazol-5-ol | 484.2182 |
| 11 | 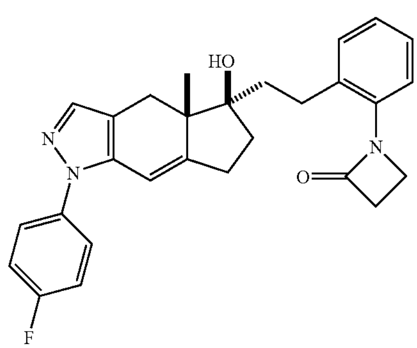 | 1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)azetidin-2-one | 458.2238 |

| Ex. | STRUCTURE | NAME | M + 1 |
|---|---|---|---|
| 12 | 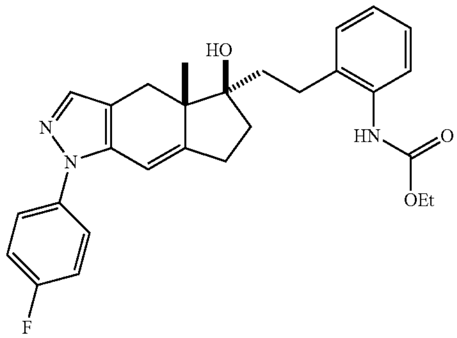 | ethyl (2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 476.2335 |
| 13 | 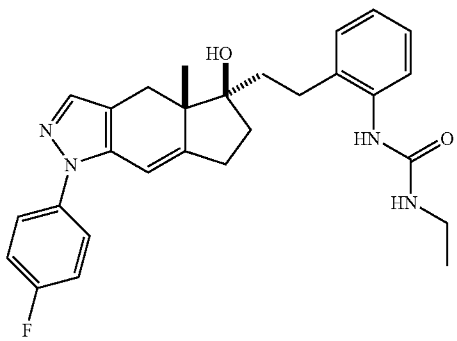 | N-ethyl-N'-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea | 475.2494 |
| 14 | 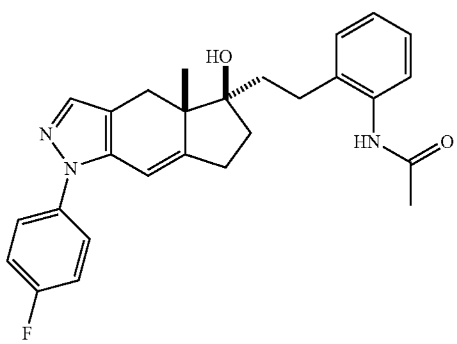 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 446.2239 |
| 15 | 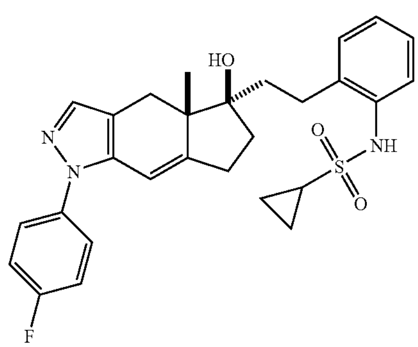 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropanesulfonamide | 508.2055 |

-continued

| Ex. | STRUCTURE | NAME | M + 1 |
|---|---|---|---|
| 18 | 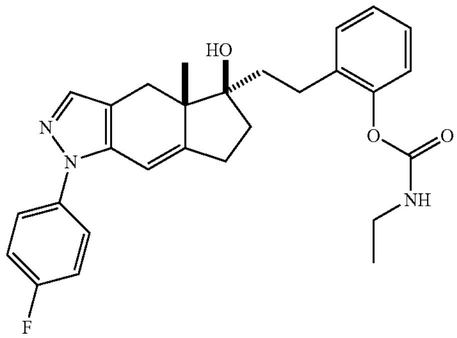 | 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl ethylcarbamate | 476.2335 |
| 19 | 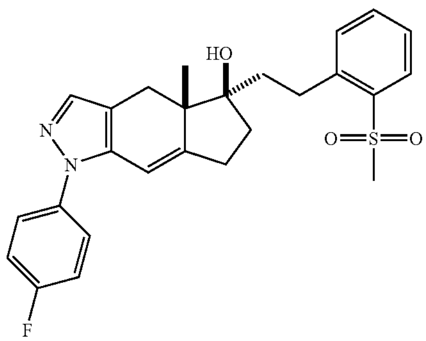 | (4αS,5R)-1-(4-fluorophenyl)-4α-methyl-5-{2-[2-(methylsulfonyl)phenyl]ethyl}-1,4,4α,5,6,7-hexahydrocyclopenta[f]indazol-5-ol | 467.1793 |
| 20 | 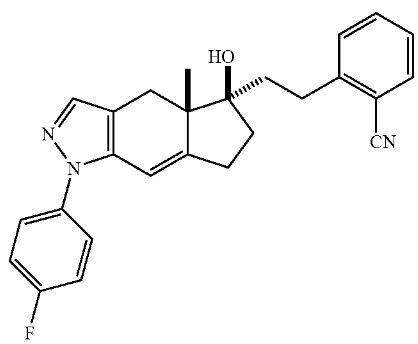 | 2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile | 414.1981 |
| 22 | 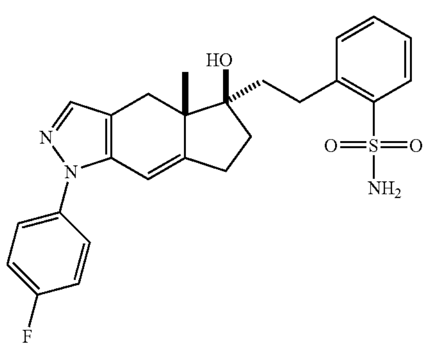 | 2-{2-[(4αS,5R)-1-(4-fluorophenyl)-5-hydroxy-4α-methyl-1,4,4α,5,6,7-hexahydrocyclopenta[f]indazol-5-yl]ethyl}benzenesulfonamide | 468.1768 |

-continued

| Ex. | STRUCTURE | NAME | M + 1 |
|---|---|---|---|
| 23 | 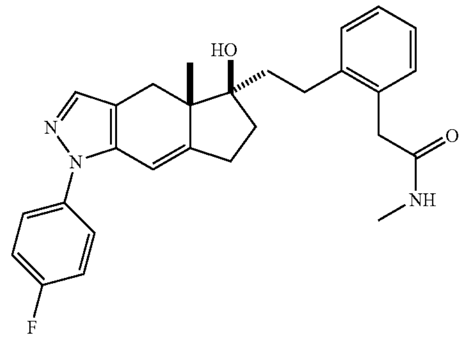 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-methylacetamide | 460.2395 |
| 24 | 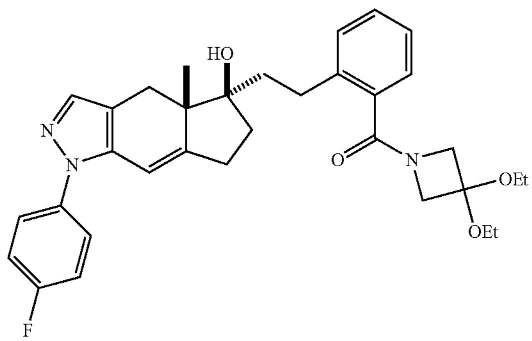 | (4αS,5R)-5-(2-{2-[(3,3-diethoxyazetidin-1-yl)carbonyl]phenyl}ethyl)-1-(4-fluorophenyl)-4α-methyl-1,4,4α,5,6,7-hexahydrocyclopenta[f]indazol-5-ol | 578.2843 |
| 25 | 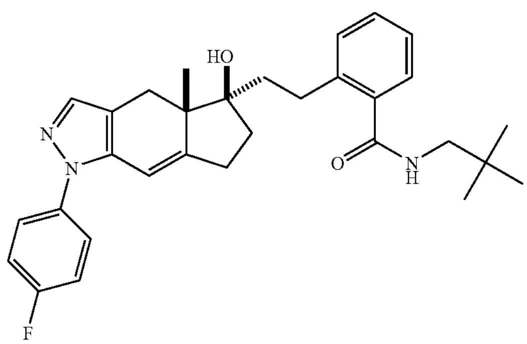 | N-(2,2-dimethylpropyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 502.2852 |
| 26 | 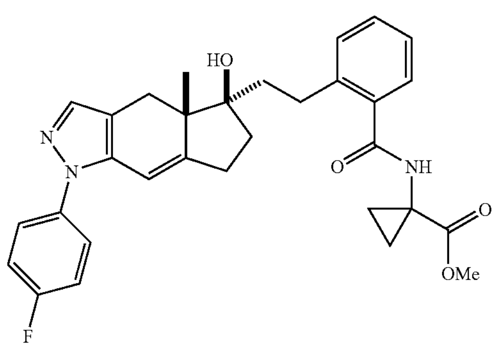 | methyl 1-[(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)amino]cyclopropanecarboxylate | 530.2450 |

-continued

| Ex. | STRUCTURE | NAME | M + 1 |
|---|---|---|---|
| 27 | 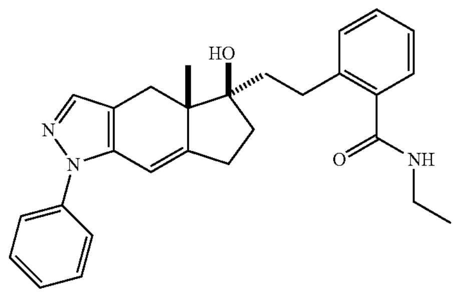 | N-ethyl-2-{2-[(4αS,5R)-5-hydroxy-4α-methyl-1-phenyl-1,4,4α,5,6,7-hexahydrocyclopenta[f]indazol-5-yl]ethyl}benzamide | 442.2501 |
| 28 | 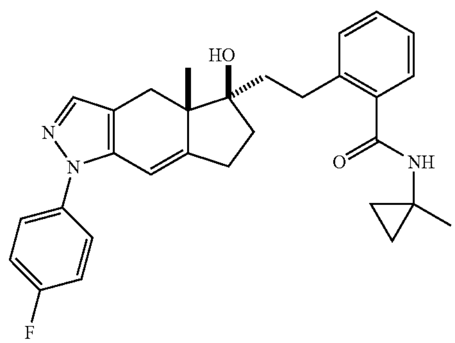 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(1-methylcyclopropyl)benzamide | 486.2548 |
| 29 | 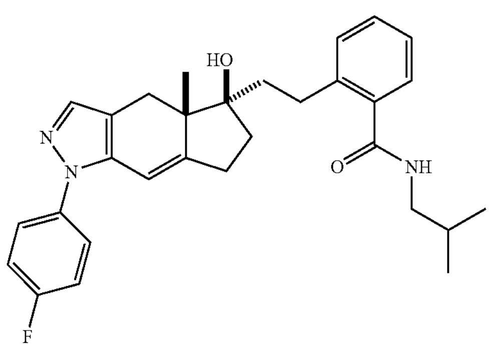 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-isobutylbenzamide | 488.2720 |
| 30 | 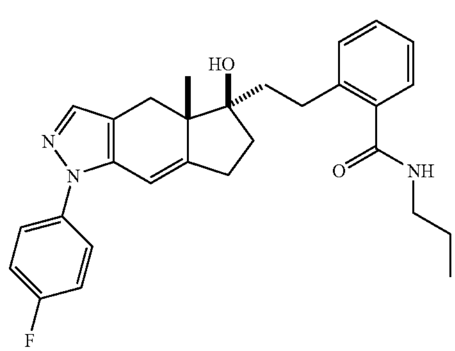 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-propylbenzamide | 474.2564 |

-continued

| Ex. | STRUCTURE | NAME | M + 1 |
|---|---|---|---|
| 31 | 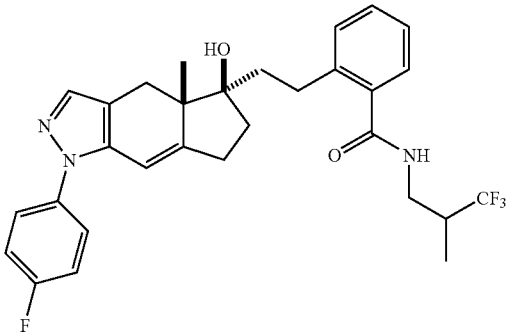 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(3,3,3-trifluoro-2-methylpropyl)benzamide | 542.2443 |
| 32 | 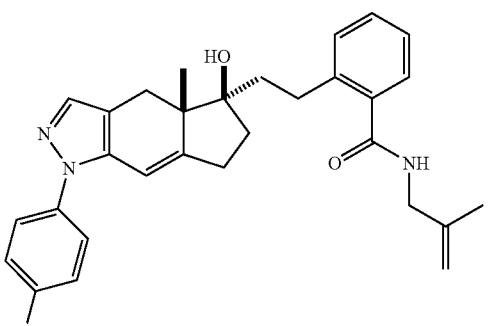 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-methylprop-2-en-1-yl)benzamide | 486.2562 |
| 33 | 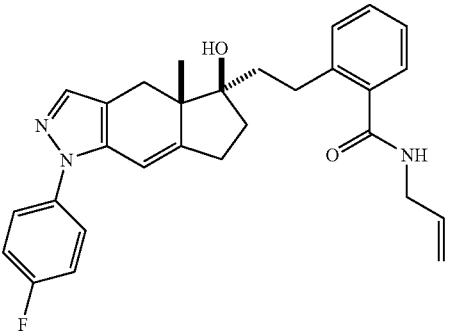 | N-allyl-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 472.2404 |
| 34 | 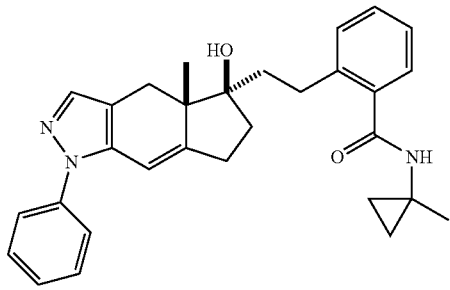 | 2-{2-[(4αS,5R)-5-hydroxy-4α-methyl-1-phenyl-1,4,4α,5,6,7-hexahydrocyclopenta[f]indazol-5-yl]ethyl}-N-(1-methylcyclopropyl)benzamide | 468.2630 |

| Ex. | STRUCTURE | NAME | M + 1 |
|---|---|---|---|
| 35 | 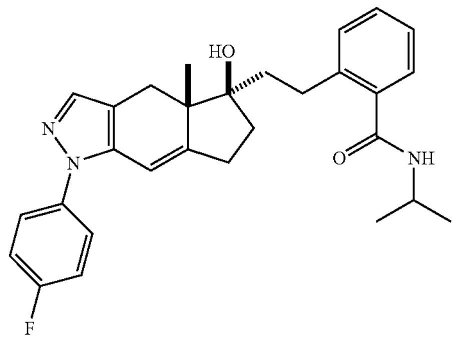 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-isopropylbenzamide | 474.2565 |
| 36 | 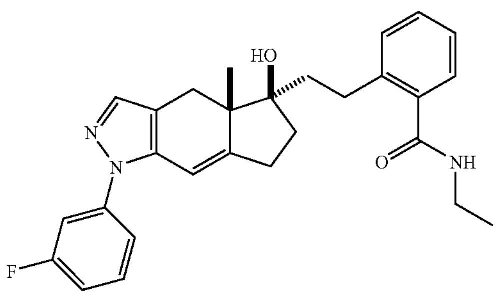 | N-ethyl-2-{2-[(4αS,5R)-1-(3-fluorophenyl)-5-hydroxy-4α-methyl-1,4,4α,5,6,7-hexahydrocyclopenta[f]indazol-5-yl]ethyl}benzamide | 460.2398 |
| 37 | 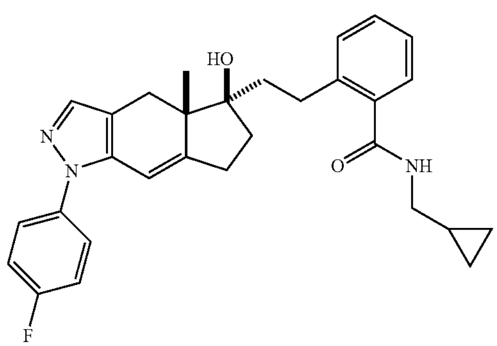 | N-(cyclopropylmethyl)-2-{2-[(4αS,5R)-1-(4-fluorophenyl)-5-hydroxy-4α-methyl-1,4,4α,5,6,7-hexahydrocyclopenta[r]indazol-5-yl]ethyl}benzamide | 486.2588 |
| 38 | 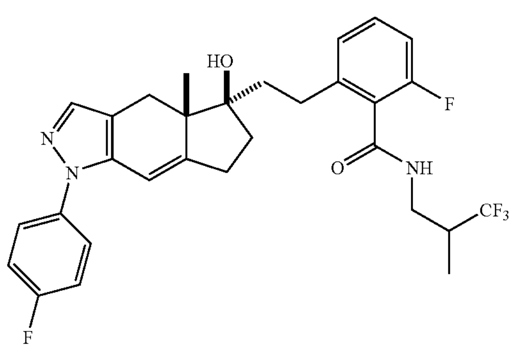 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(3,3,3-trifluoro-2-methylpropyl)benzamide | 560.2323 |

-continued

| Ex. | STRUCTURE | NAME | M + 1 |
|---|---|---|---|
| 39 | 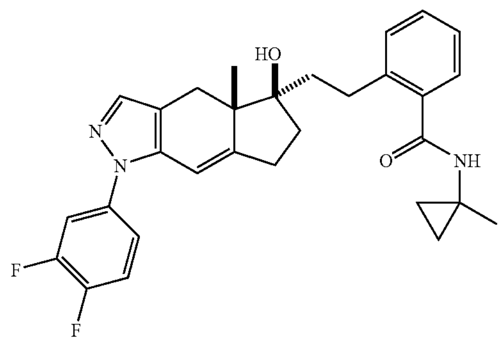 | 2-{2-[(4αS,5R)-1-(3,4-difluorophenyl)-5-hydroxy-4α-methyl-1,4,4α,5,6,7-hexahydrocyclopenta[f]indazol-5-yl]ethyl}-N-(1-methylcyclopropyl)benzamide | 504.2460 |
| 40 | 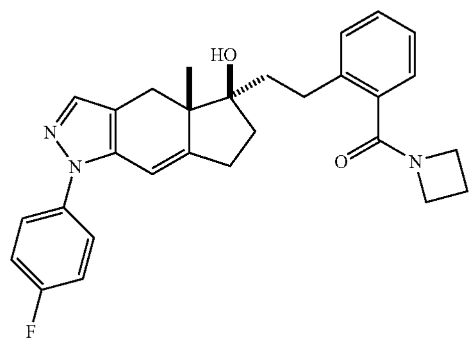 | (4αS,5R)-5-{2-[2-(azetidin-1-ylcarbonyl)phenyl]ethyl}-1-(4-fluorophenyl)-4α-methyl-1,4,4α,5,6,7-hexahydrocyclopenta[f]indazol-5-ol | 472.2387 |
| 41 | 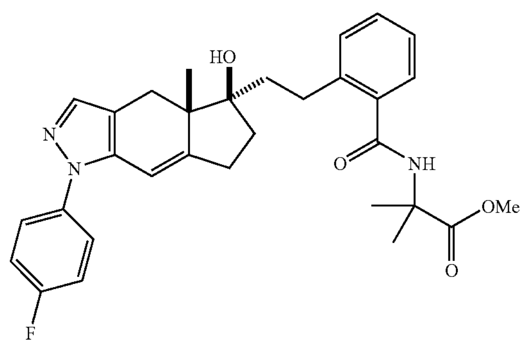 | methyl N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-2-methylalaninate | 550.2513 |
| 42 | 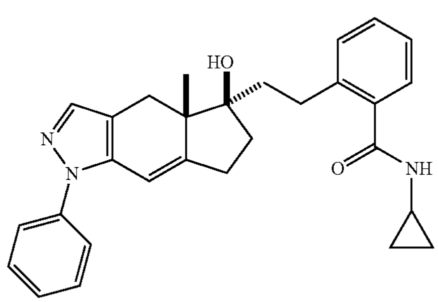 | N-cyclopropyl-2-{2-[(4αS,5R)-5-hydroxy-4α-methyl-1-phenyl-1,4,4α,5,6,7-hexahydrocyclopenta[f]indazol-5-yl]ethyl}benzamide | 454.2504 |
| 43 | 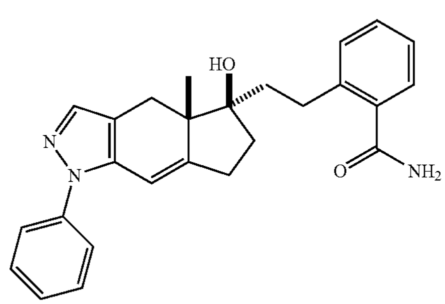 | 2-{2-[(4αS,5R)-5-hydroxy-4α-methyl-1-phenyl-1,4,4α,5,6,7-hexahydrocyclopenta[f]indazol-5-yl]ethyl}benzamide | 414.2188 |

| Ex. | STRUCTURE | NAME | M + 1 |
|---|---|---|---|
| 44 | 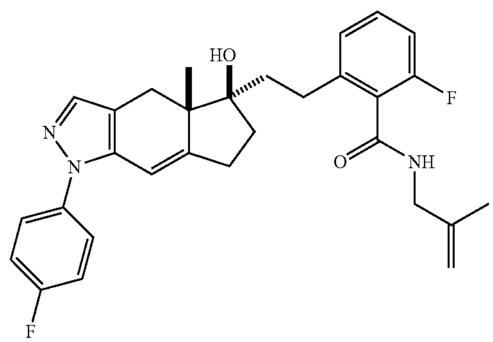 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-methylprop-2-en-1-yl)benzamide | 504.2456 |
| 45 | 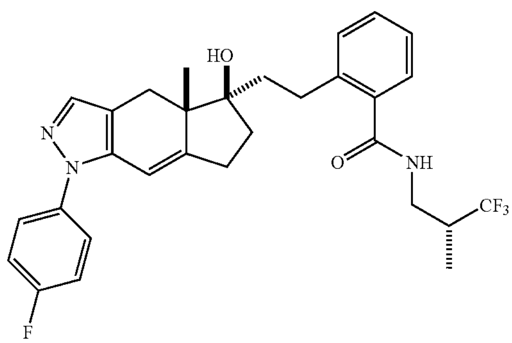 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-[(2R)-3,3,3-trifluoro-2-methylpropyl]benzamide | 542.2414 |
| 46 | 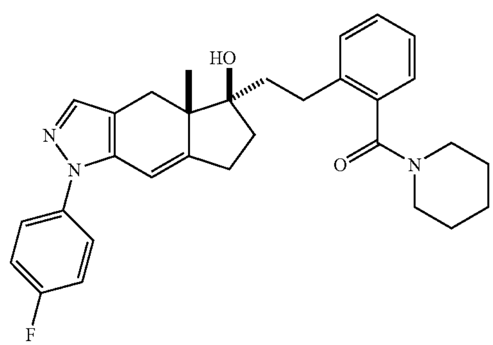 | (4αS,5R)-1-(4-fluorophenyl)-4α-methyl-5-{2-[2-(piperidin-1-ylcarbonyl)phenyl]ethyl}-1,4,4α,5,6,7-hexahydrocyclopenta[f]indazol-5-ol | 500.2696 |
| 47 | 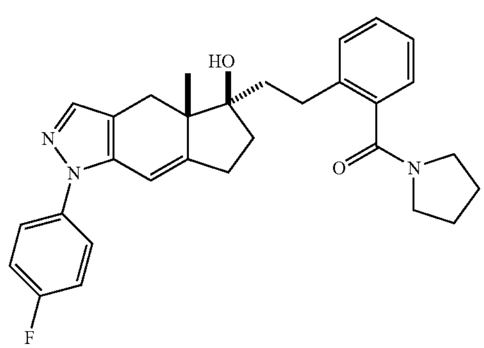 | (4αS,5R)-1-(4-fluorophenyl)-4α-methyl-5-{2-[2-(pyrrolidin-1-ylcarbonyl)phenyl]ethyl}-1,4,4α,5,6,7-hexahydrocyclopenta[f]indazol-5-ol | 486.2538 |

-continued

| Ex. | STRUCTURE | NAME | M + 1 |
|---|---|---|---|
| 48 | 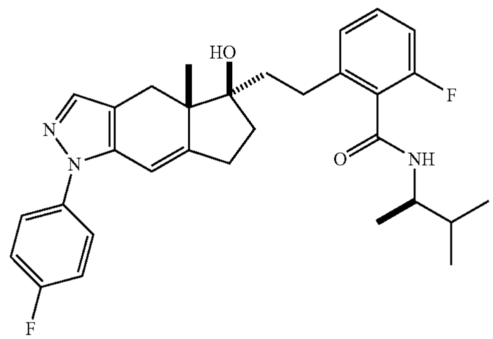 | N-[(1R)-1,2-dimethylpropyl]-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 520.2765 |
| 49 | 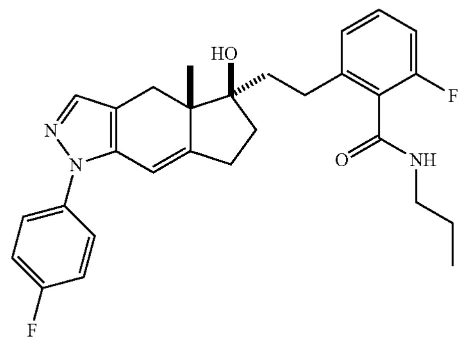 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-propylbenzamide | 492.2456 |
| 50 | 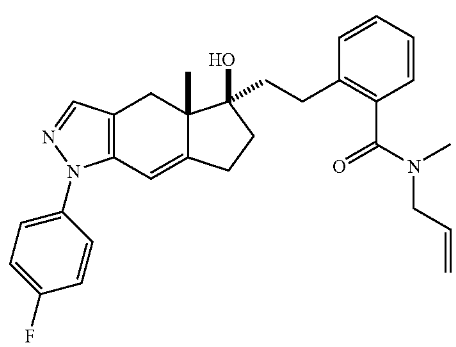 | N-allyl-2-{2-[(4αS,5R)-1-(4-fluorophenyl)-5-hydroxy-4α-methyl-1,4,4α,5,6,7-hexahydrocyclopenta[f]indazol-5-yl]ethyl}-N-methylbenzamide | 486.2555 |
| 51 | 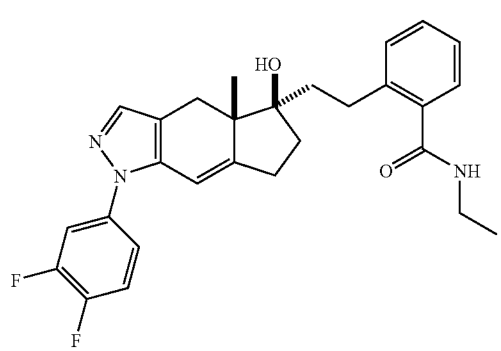 | 2-{2-[(4αS,5R)-1-(3,4-difluorophenyl)-5-hydroxy-4α-methyl-1,4,4α,5,6,7-hexahydrocyclopenta[f]indazol-5-yl]ethyl}-N-ethylbenzamide | 478.2302 |

-continued

| Ex. | STRUCTURE | NAME | M + 1 |
|---|---|---|---|
| 52 | 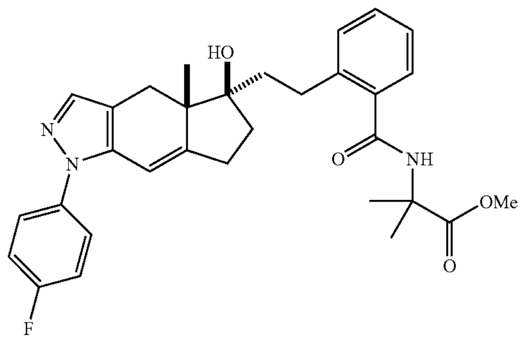 | methyl N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-2-methylalaninate | 532.2594 |
| 53 | 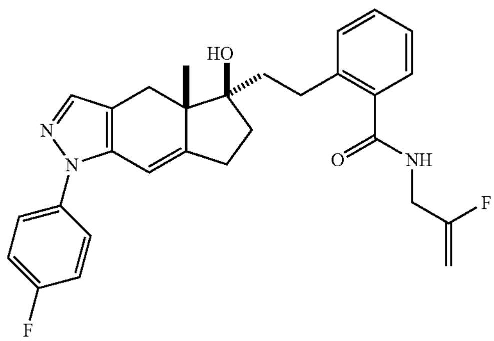 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-fluoroprop-2-en-1-yl)benzamide | 490.2311 |
| 54 | 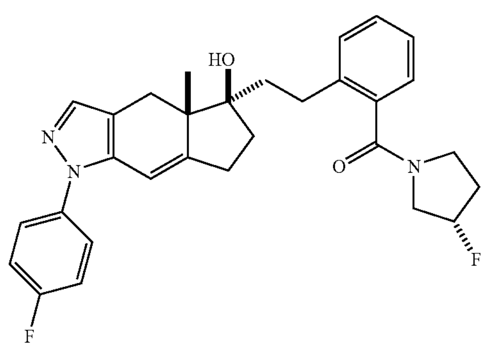 | (4αS,5R)-1-(4-fluorophenyl)-5-[2-(2-{[(3S)-3-fluoropyrrolidin-1-yl]carbonyl}phenyl)ethyl]-4α-methyl-1,4,4α,5,6,7-hexahydrocyclopenta[f]indazol-5-ol | 504.2433 |
| 55 | 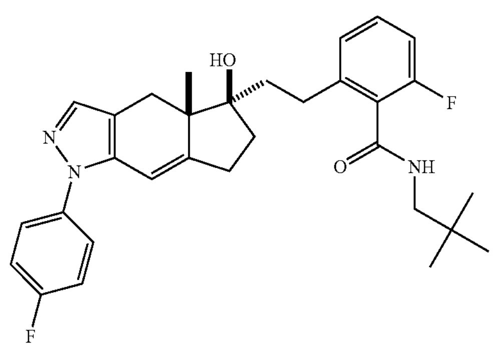 | N-(2,2-dimethylpropyl)-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 520.2768 |

-continued

| Ex. | STRUCTURE | NAME | M + 1 |
|---|---|---|---|
| 56 | 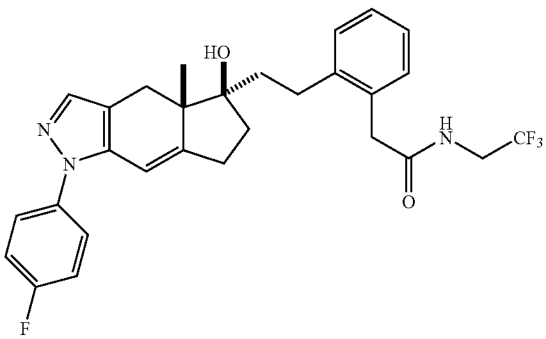 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-(2,2,2-trifluoroethyl)acetamide | 528.2264 |
| 57 | 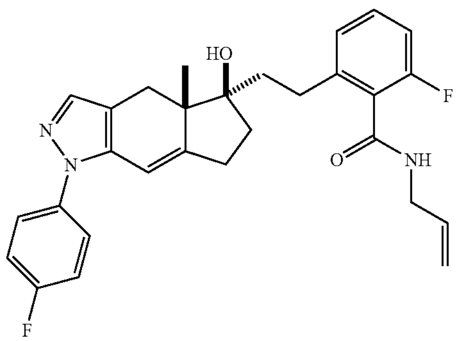 | N-allyl-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 490.2302 |
| 58 | 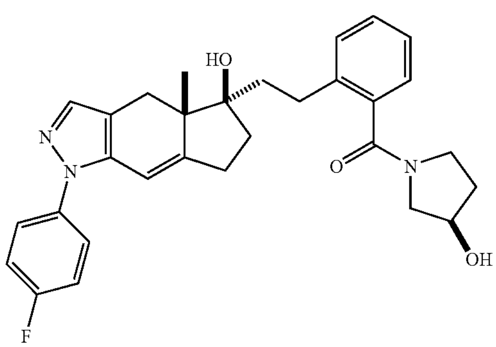 | (4αS,5R)-1-(4-fluorophenyl)-5-[2-(2-{[(3R)-3-hydroxypyrrolidin-1-yl]carbonyl}phenyl)ethyl]-4α-methyl-1,4,4α,5,6,7-hexahydrocyclopenta[f]indazol-5-ol | 502.2498 |
| 59 | 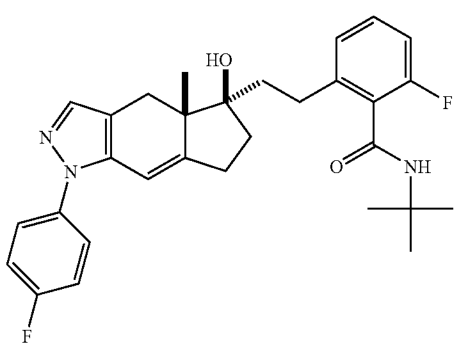 | N-(tert-butyl)-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 506.2610 |

-continued

| Ex. | STRUCTURE | NAME | M + 1 |
|---|---|---|---|
| 60 | 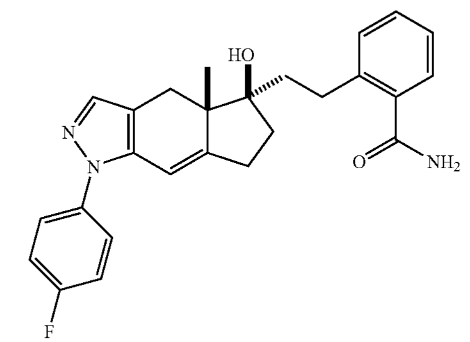 | 2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 432.2084 |
| 61 | 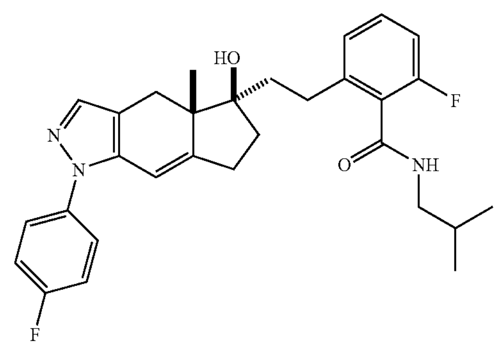 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-isobutylbenzamide | 506.2615 |
| 62 | 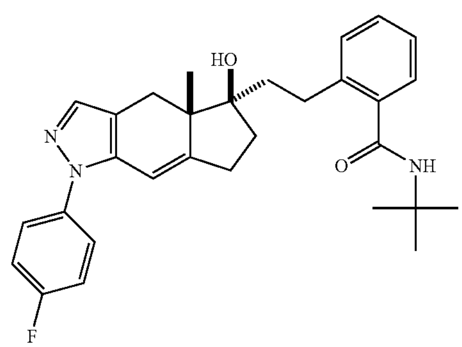 | N-(tert-butyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 488.2701 |
| 63 | 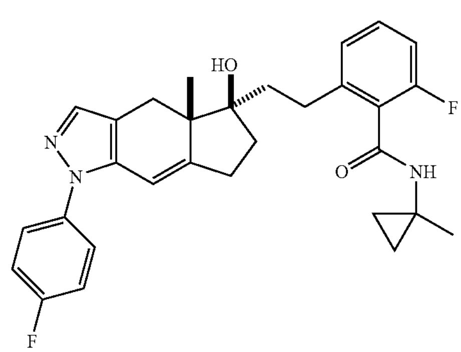 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(1-methylcyclopropyl)benzamide | 504.2460 |

-continued

| Ex. | STRUCTURE | NAME | M + 1 |
|---|---|---|---|
| 64 | 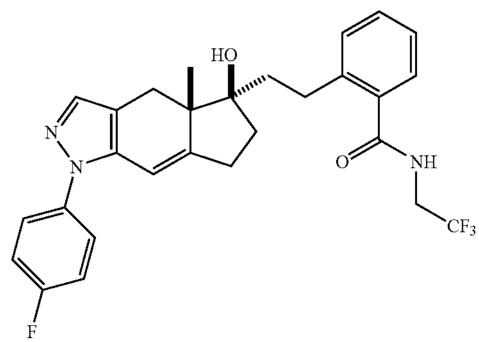 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2,2,2-trifluoroethyl)benzamide | 514.2153 |
| 65 | 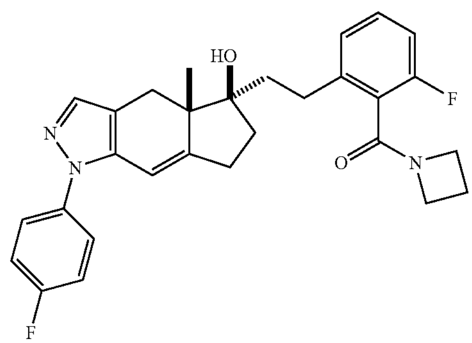 | (4αS,5R)-5-{2-[2-(azetidin-1-ylcarbonyl)-3-fluorophenyl]ethyl}-1-(4-fluorophenyl)-4α-methyl-1,4,4α,5,6,7-hexahydrocyclopenta[f]indazol-5-ol | 490.2296 |
| 66 | 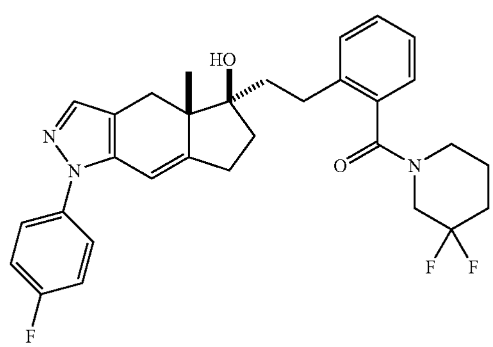 | (4αS,5R)-5-(2-{2-{[(3,3-difluoropiperidin-1-yl)carbonyl]phenyl}ethyl)-1-(4-fluorophenyl)-4α-methyl-1,4,4α,5,6,7-hexahydrocyclopenta[f]indazol-5-ol | 536.2510 |
| 67 | 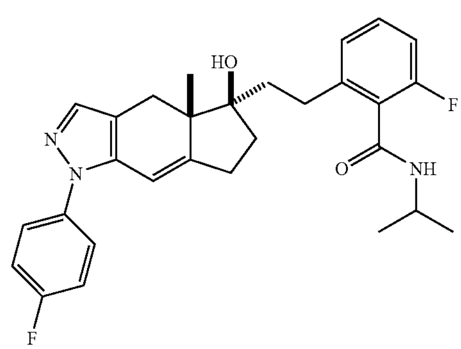 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-isopropylbenzamide | 492.2454 |

-continued

| Ex. | STRUCTURE | NAME | M + 1 |
|---|---|---|---|
| 68 | 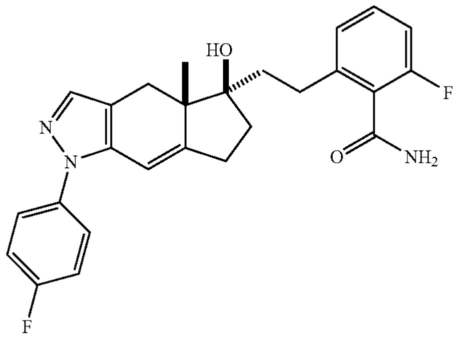 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 450.1994 |
| 69 | 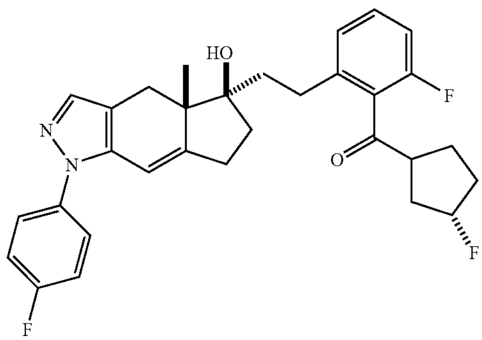 | (4αS,5R)-5-[2-(3-fluoro-2-{[(3S)-3-fluoropyrrolidin-1-yl]carbonyl}phenyl)ethyl]-1-(4-fluorophenyl)-4α-methyl-1,4,4α,5,6,7-hexahydrocyclopenta[f]indazol-5-ol | 522.2359 |
| 70 | 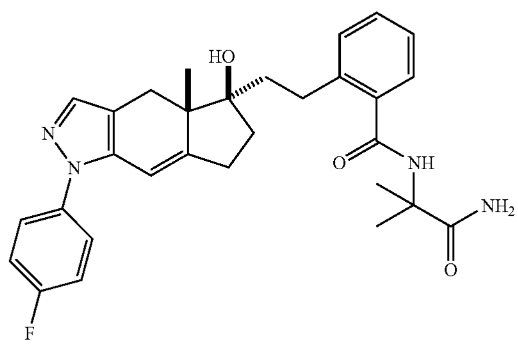 | N-(2-amino-1,1-dimethyl-2-oxoethyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 517.2614 |
| 71 | 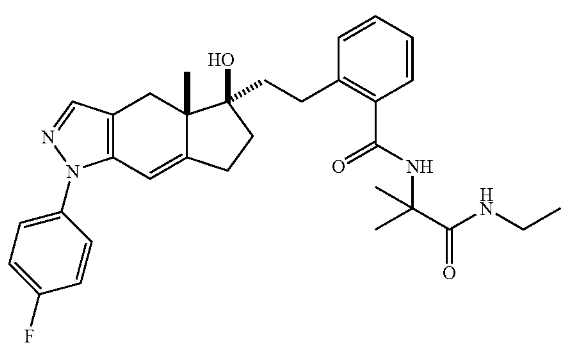 | N-[2-(ethylamino)-1,1-dimethyl-2-oxoethyl]-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 545.2915 |

| Ex. | STRUCTURE | NAME | M + 1 |
|---|---|---|---|
| 72 | 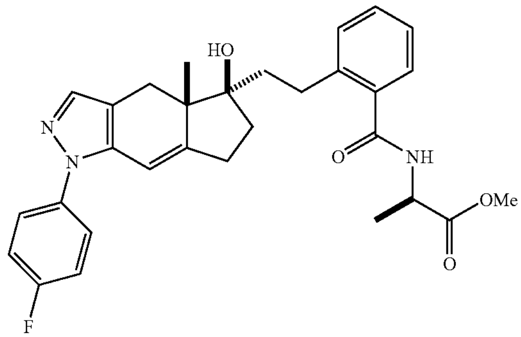 | methyl N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-D-alaninate | 518.2447 |
| 73 | 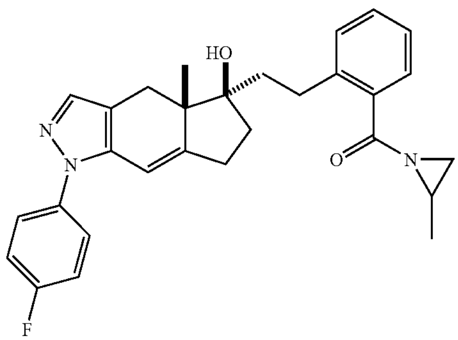 | (4αS,5R)-1-(4-fluorophenyl)-4α-methyl-5-(2-{2-[(2-methylaziridin-1-yl)carbonyl]phenyl}ethyl)-1,4,4α,5,6,7-hexahydrocyclopenta[f]indazol-5-ol | 472.2385 |
| 74 | 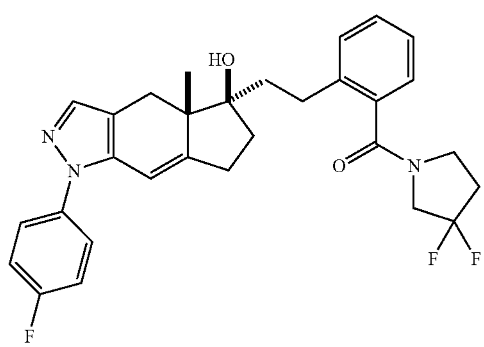 | (4αS,5R)-5-(2-{2-[(3,3-difluoropyrrolidin-1-yl)carbonyl]phenyl}ethyl)-1-(4-fluorophenyl)-4α-methyl-1,4,4α,5,6,7-hexahydrocyclopenta[f]indazol-5-ol | 522.2356 |
| 75 | 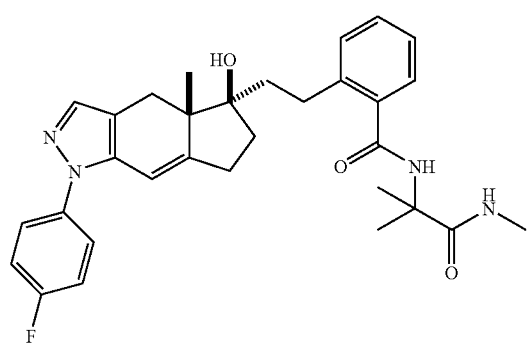 | N-[1,1-dimethyl-2-(methylamino)-2-oxoethyl]-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 531.2753 |

-continued

| Ex. | STRUCTURE | NAME | M + 1 |
|---|---|---|---|
| 76 | 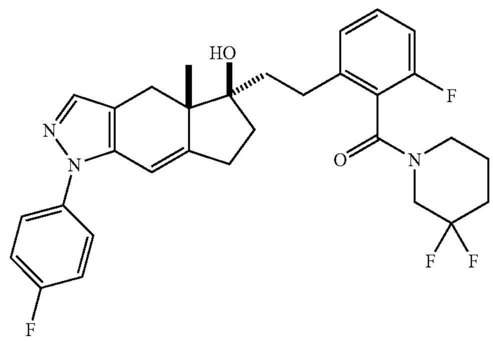 | (4αS,5R)-5-(2-{2-[(3,3-difluoropiperidin-1-yl)carbonyl]-3-fluorophenyl}ethyl)-1-(4-fluorophenyl)-4α-methyl-1,4,4α,5,6,7-hexahydrocyclopenta[f]indazol-5-ol | 554.2414 |
| 77 | 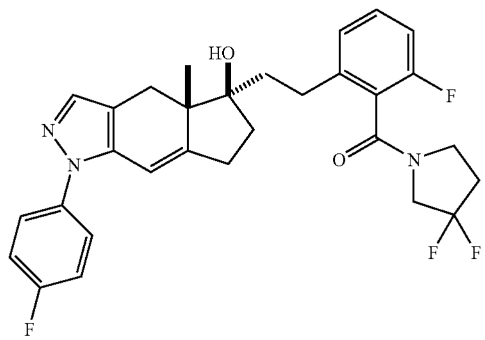 | (4αS,5R)-5-(2-{2-[(3,3-difluoropyrrolidin-1-yl)carbonyl]-3-fluorophenyl}ethyl)-1-(4-fluorophenyl)-4α-methyl-1,4,4α,5,6,7-hexahydrocyclopenta[f]indazol-5-ol | 540.2265 |
| 78 | 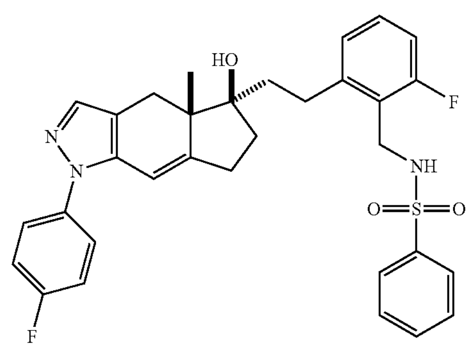 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide | 576.2144 |
| 79 | 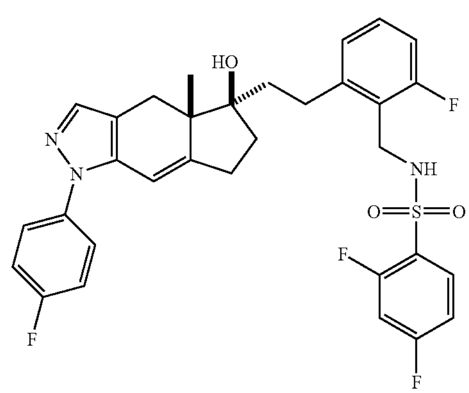 | 2,4-difluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide | 612.1950 |

| Ex. | STRUCTURE | NAME | M + 1 |
|---|---|---|---|
| 80 | 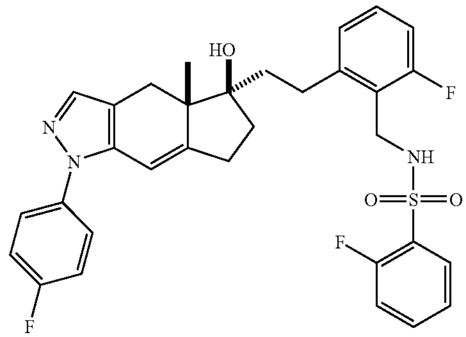 | 2-fluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide | 594.2044 |
| 81 | 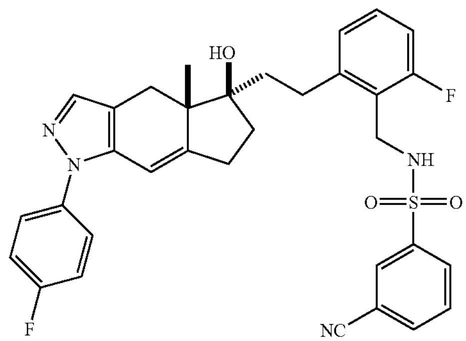 | 3-cyano-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide | 601.2080 |
| 82 | 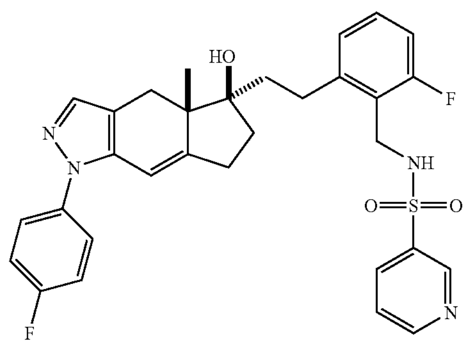 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)pyridine-3-sulfonamide | 577.2091 |
| 83 | 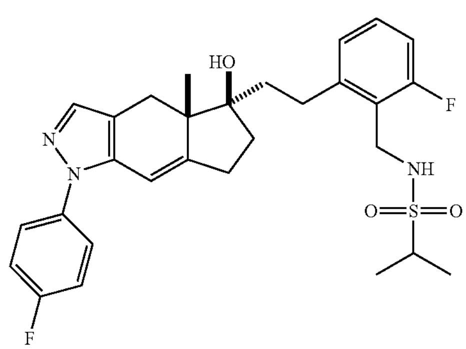 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)propane-2-sulfonamide | 542.2313 |

-continued

| Ex. | STRUCTURE | NAME | M + 1 |
|---|---|---|---|
| 84 | 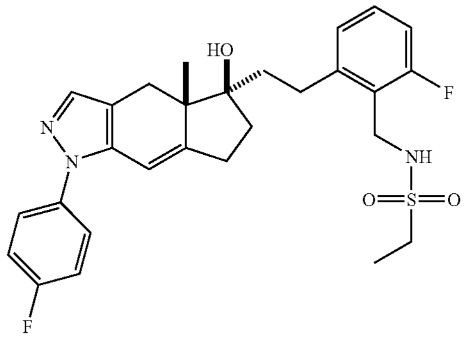 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide | 528.2124 |
| 85 | 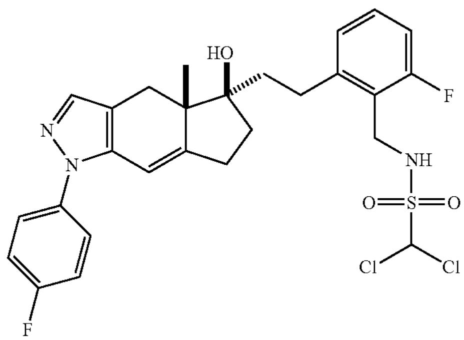 | 1,1-dichloro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide | 582.1204 |
| 86 | 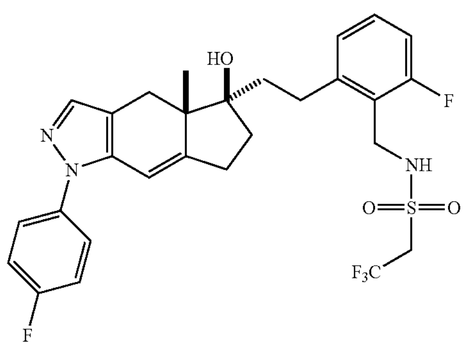 | 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide | 582.1741 |
| 87 | 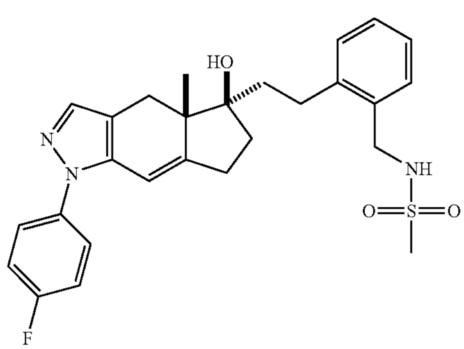 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide | 496.2062 |

-continued

| Ex. | STRUCTURE | NAME | M + 1 |
|---|---|---|---|
| 88 | 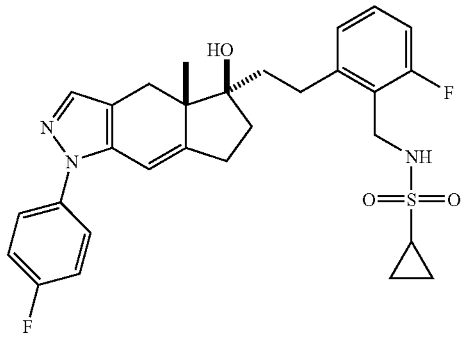 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)cyclopropanesulfonamide | 540.2124 |
| 89 | 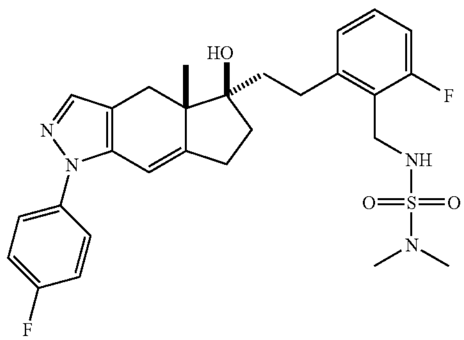 | N'-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)-N,N-dimethylsulfamide | 543.2265 |
| 90 | 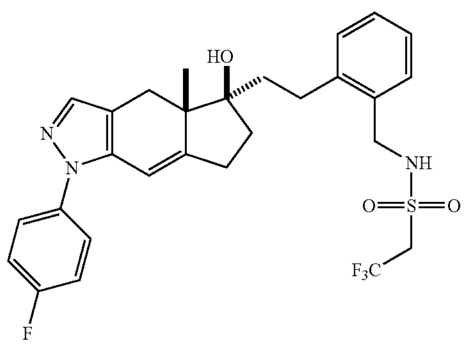 | 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide | 564.1943 |
| 91 | 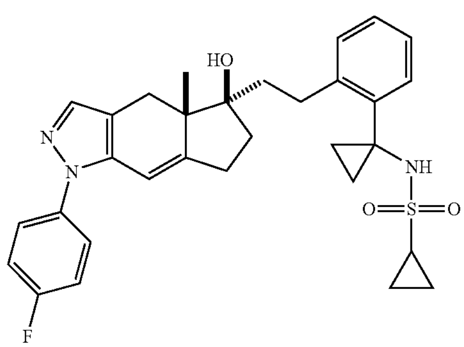 | N-[1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropyl]cyclopropanesulfonamide | 548.2371 |

| Ex. | STRUCTURE | NAME | M + 1 |
|---|---|---|---|
| 92 | 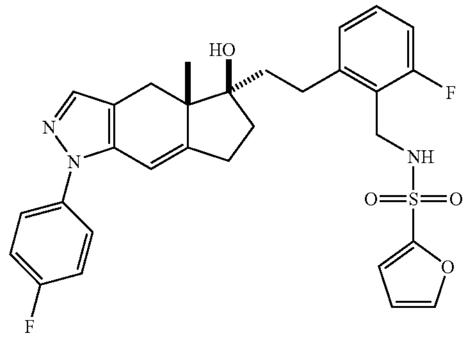 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)furan-2-sulfonamide | 566.1930 |
| 93 | 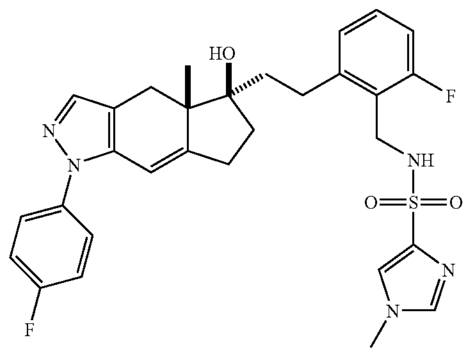 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)-1-methyl-1H-imidazole-4-sulfonamide | 580.2221 |
| 94 | 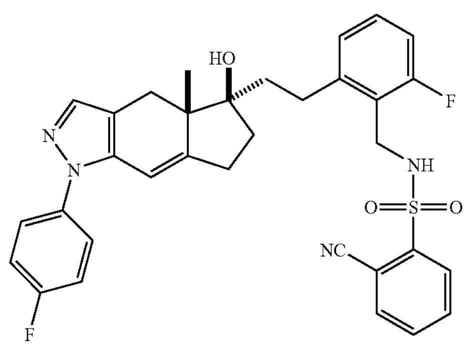 | 2-cyano-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide | 601.2089 |
| 95 | 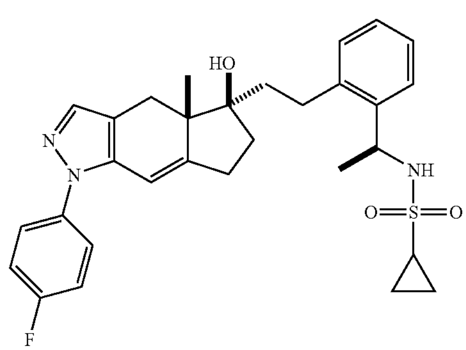 | N-[(1S)-1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]cyclopropanesulfonamide | 536.2387 |

-continued

| Ex. | STRUCTURE | NAME | M + 1 |
|---|---|---|---|
| 96 | 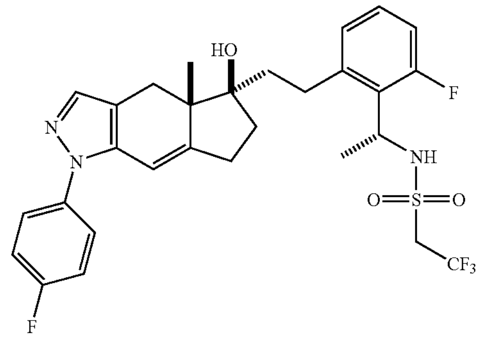 | 2,2,2-trifluoro-N-[(1R)-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide | 596.1988 |
| 97 | 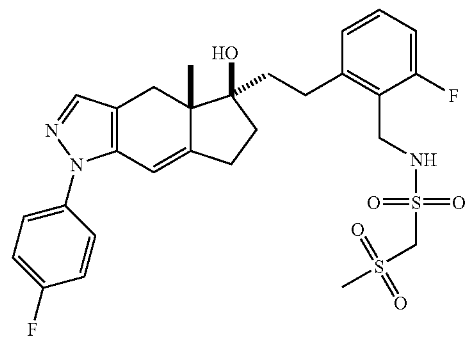 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)-1-(methylsulfonyl)methanesulfonamide | 592.1768 |
| 98 | 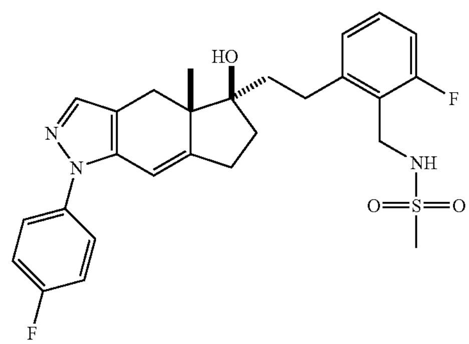 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide | 514.1967 |
| 99 | 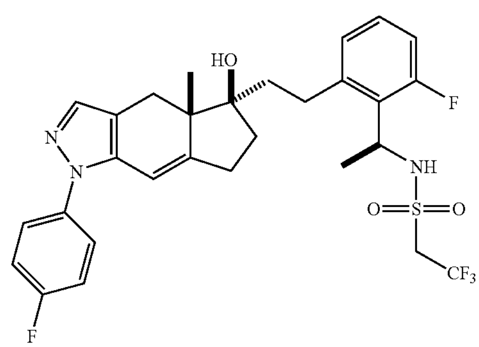 | 2,2,2-trifluoro-N-[(1S)-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide | 596.1987 |

-continued

| Ex. | STRUCTURE | NAME | M + 1 |
|---|---|---|---|
| 100 | 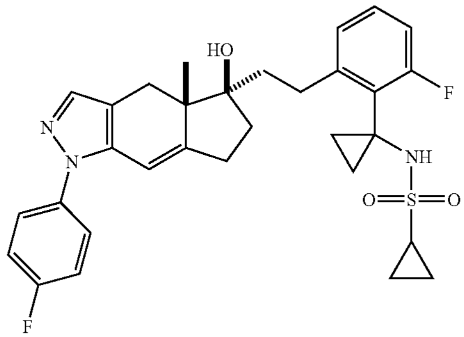 | N-[1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropyl]cyclopropanesulfonamide | 566.2272 |
| 101 | 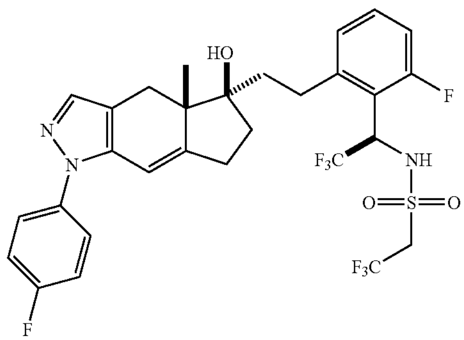 | 2,2,2-trifluoro-N-[(1R)-2,2,2-trifluoro-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide | 650.1703 |
| 102 | 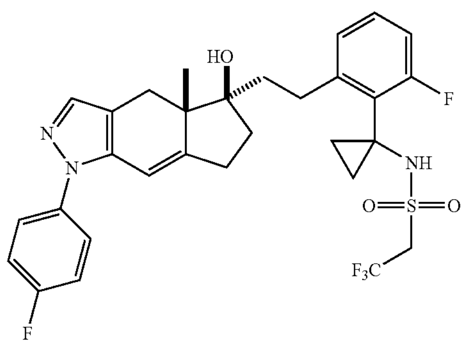 | 2,2,2-trifluoro-N-[1-(2-fluoro-6-{2-[(4αS,5R)-1-(4-fluorophenyl)-5-hydroxy-4α-methyl-1,4,4α,5,6,7-hexahydrocyclopenta[f]indazol-5-102yl]ethyl}phenyl)cyclopropyl]ethanesulfonamide | 608.1988 |
| 103 | 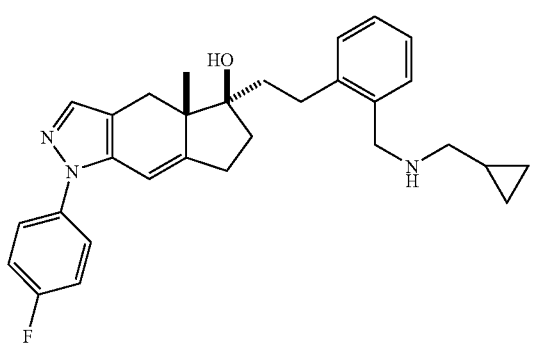 | (4αS,5R)-5-[2-(2-{[(cyclopropylmethyl)amino]methyl}phenyl)ethyl]-1-(4-fluorophenyl)-4α-methyl-1,4,4α,5,6,7-hexahydrocyclopenta[f]indazol-5-ol | 472.2760 |

-continued

| Ex. | STRUCTURE | NAME | M + 1 |
|---|---|---|---|
| 104 | 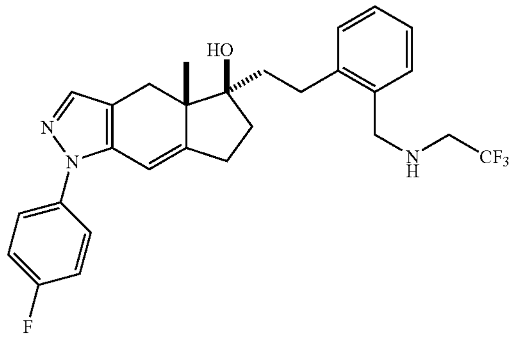 | (4αS,5R)-1-(4-fluorophenyl)-4α-methyl-5-[2-[2-{[(2,2,2-trifluoroethyl)amino]methyl}phenyl)ethyl]-1,4,4α,5,6,7-hexahydrocyclopenta[f]indazol-5-ol | 500.2319 |
| 105 | 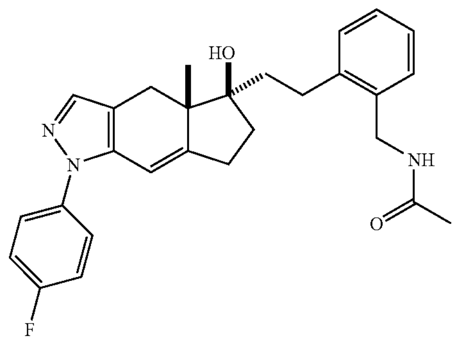 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)acetamide | 460.2402 |
| 106 | 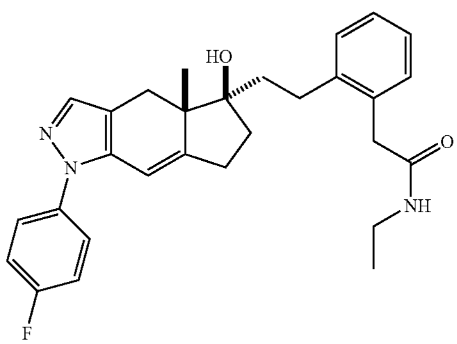 | N-ethyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 474.2554 |
| 107 | 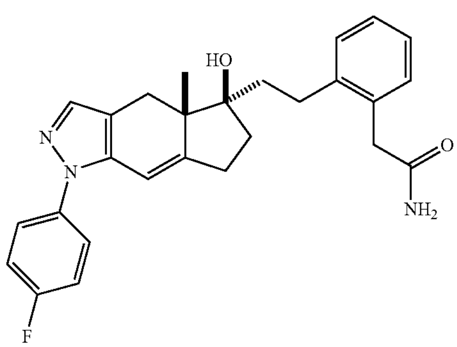 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 446.2236 |

-continued

| Ex. | STRUCTURE | NAME | M + 1 |
|---|---|---|---|
| 108 | 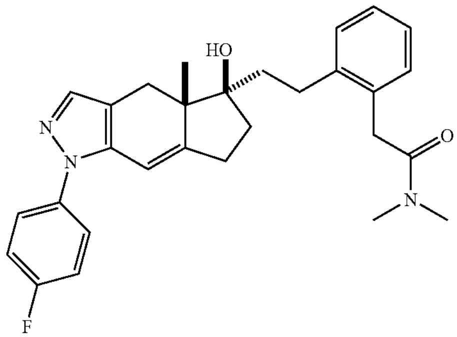 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylacetamide | 474.2553 |
| 109 | 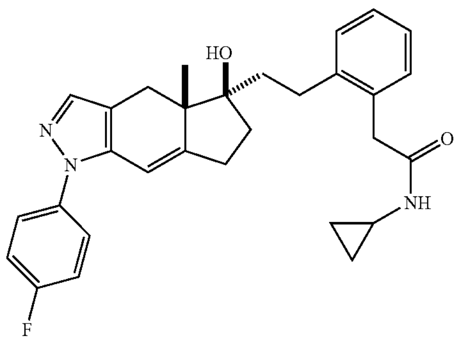 | N-cyclopropyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 486.2549 |
| 110 | 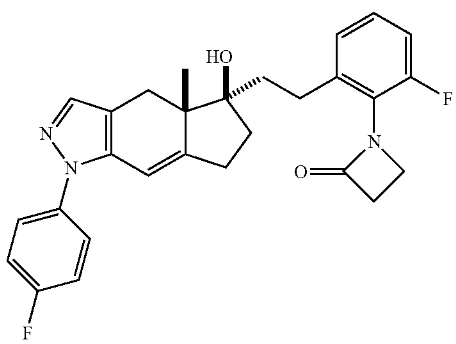 | 1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)azetidin-2-one | 476.2129 |
| 111 | 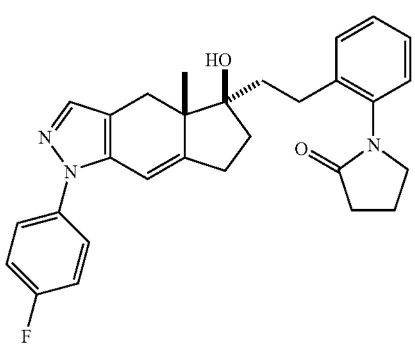 | 1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)pyrrolidin-2-one | 472.2394 |

-continued

| Ex. | STRUCTURE | NAME | M + 1 |
|---|---|---|---|
| 112 | 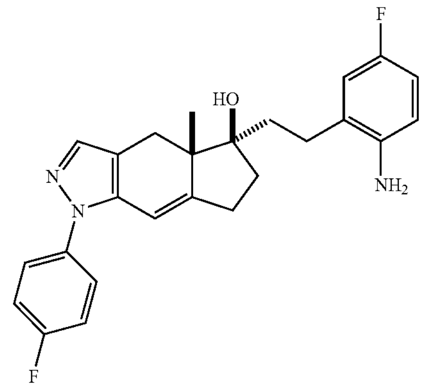 | (4αS,5R)-5-[2-(2-amino-5-fluorophenyl)ethyl]-1-(4-fluorophenyl)-4α-methyl-1,4,4α,5,6,7-hexahydrocyclopenta[f]indazol-5-ol | 422.2036 |
| 113 | 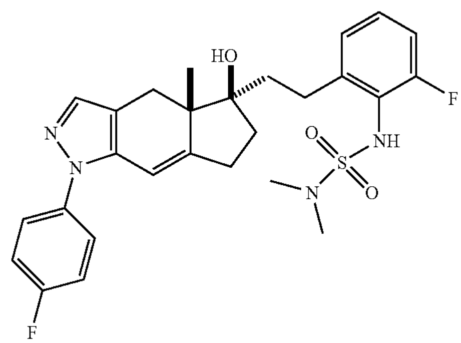 | N'-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylsulfamide | 529.2068 |
| 114 | 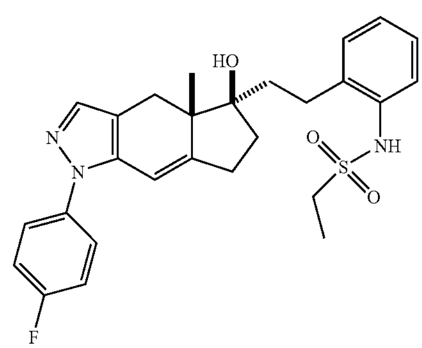 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide | 496.2055 |
| 115 | 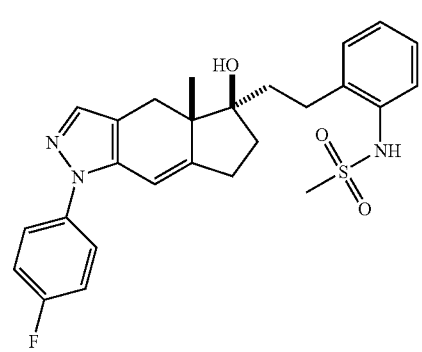 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)methanesulfonamide | 482.1899 |

-continued

| Ex. | STRUCTURE | NAME | M + 1 |
|---|---|---|---|
| 116 | 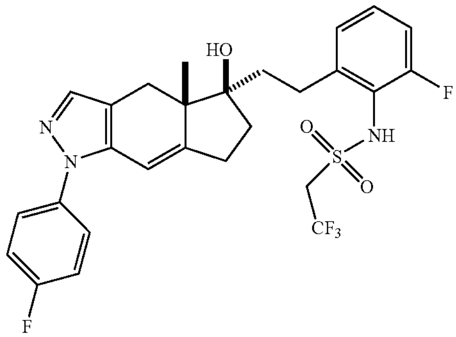 | 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide | 568.1673 |
| 117 | 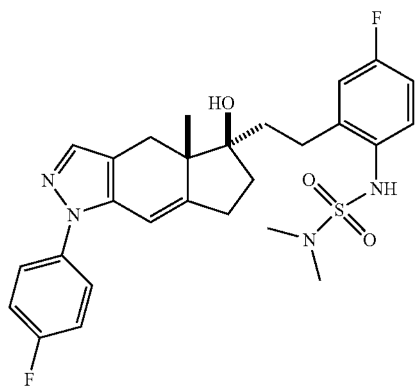 | N'-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylsulfamide | 529.2064 |
| 118 | 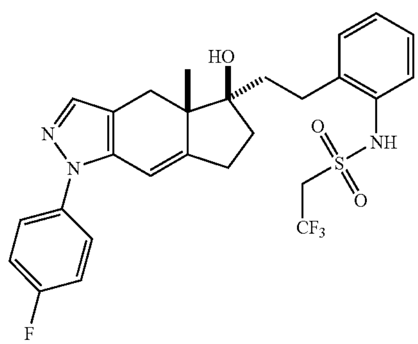 | 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide | 550.1770 |
| 119 | 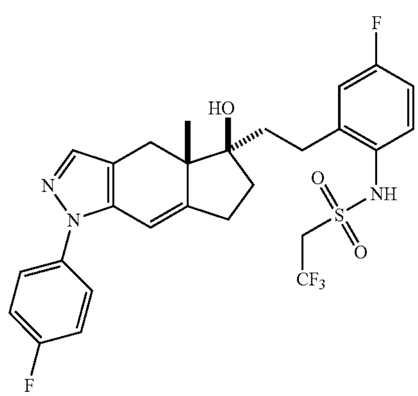 | 2,2,2-trifluoro-N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide | 568.1662 |

| Ex. | STRUCTURE | NAME | M + 1 |
|---|---|---|---|
| 120 | 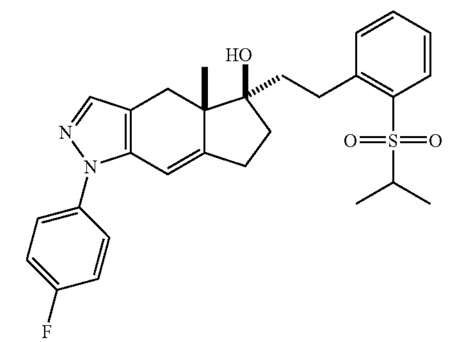 | (4αS,5R)-1-(4-fluorophenyl)-5-{2-[2-(isopropylsulfonyl)phenyl]ethyl}-4α-methyl-1,4,4α,5,6,7-hexahydrocyclopenta[f]indazol-5-ol | 495.2106 |
| 121 | 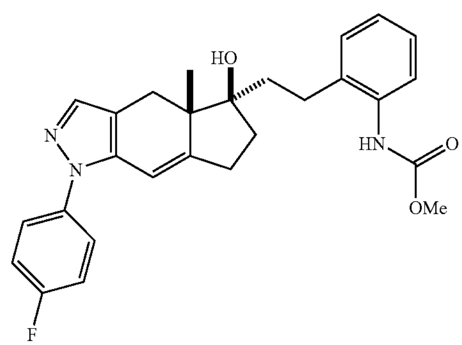 | methyl (2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 462.2178 |
| 122 | 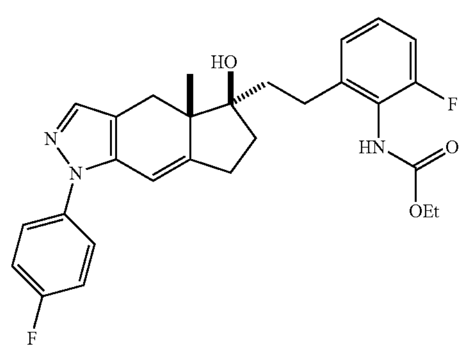 | ethyl (2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 494.2240 |
| 123 | 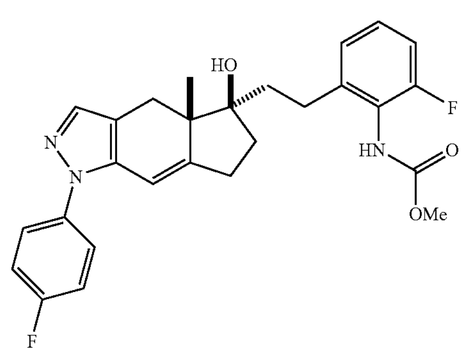 | methyl (2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 480.2086 |

-continued

| Ex. | STRUCTURE | NAME | M + 1 |
|---|---|---|---|
| 124 | 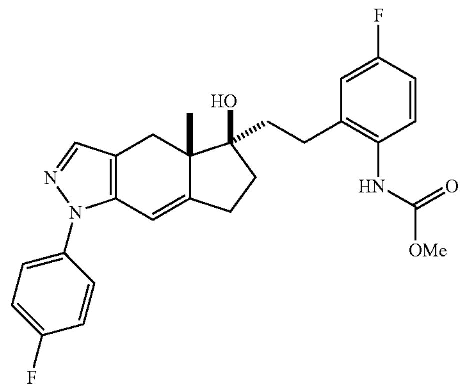 | methyl (4-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 480.2083 |
| 125 | 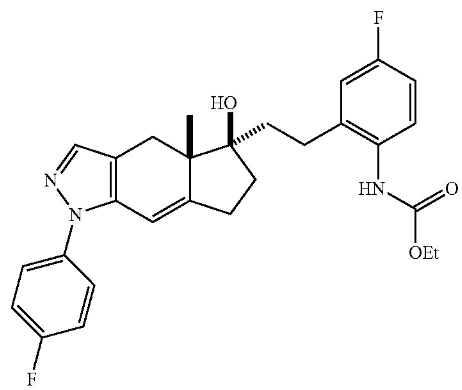 | ethyl (4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate | 502.1904 |
| 126 | 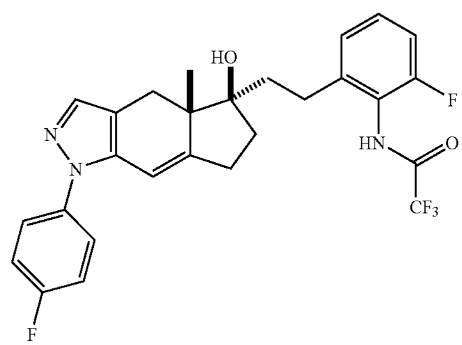 | 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 518.1848 |
| 127 | 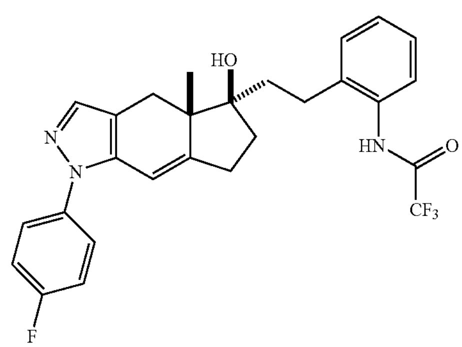 | 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 500.1939 |

-continued

| Ex. | STRUCTURE | NAME | M + 1 |
|---|---|---|---|
| 128 | 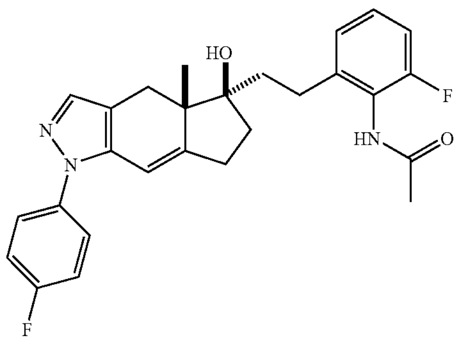 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 464.2135 |
| 129 | 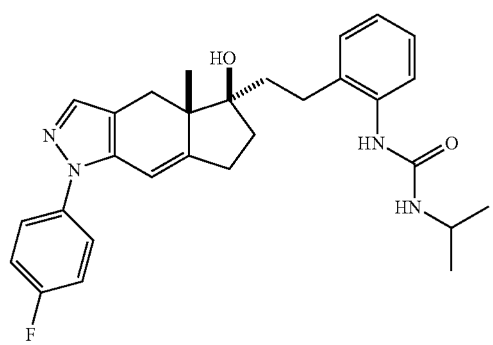 | N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N'-isopropylurea | 489.2652 |
| 130 | 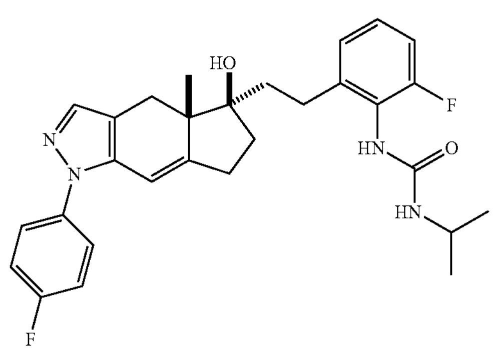 | N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N'-isopropylurea | 507.2558 |
| 131 | 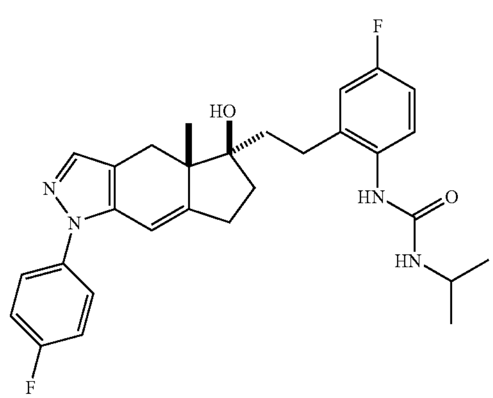 | N-ethyl-N'-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea | 493.2428 |

-continued

| Ex. | STRUCTURE | NAME | M + 1 |
|---|---|---|---|
| 132 | 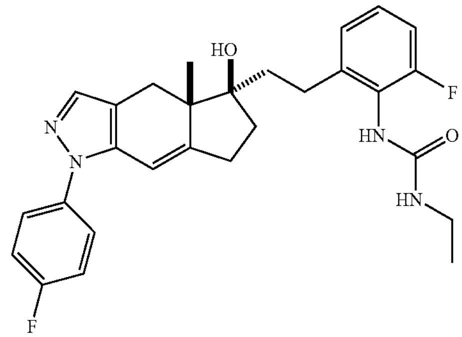 | N-ethyl-N'-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea | 493.2401 |
| 133 | 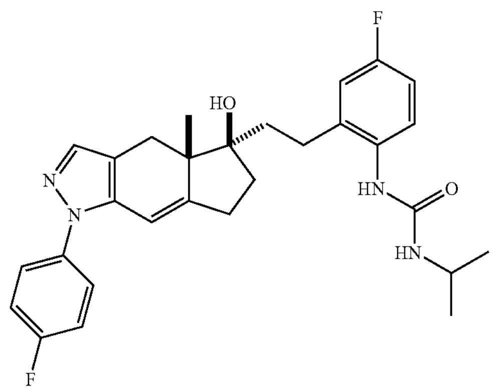 | N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N'-isopropylurea | 507.2580 |
| 134 | 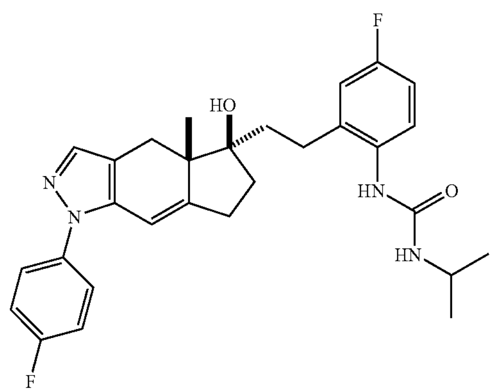 | N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N'-isopropylurea | 446.2239 |
| 135 | 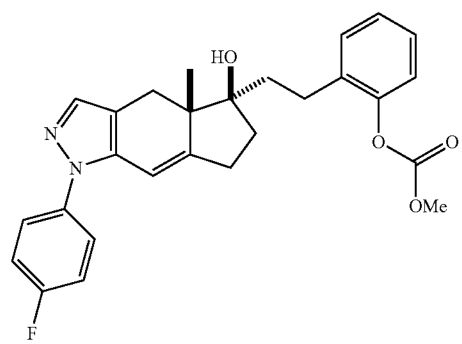 | 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl methyl carbonate | 463.2019 |

| Ex. | STRUCTURE | NAME | M + 1 |
|---|---|---|---|
| 136 | 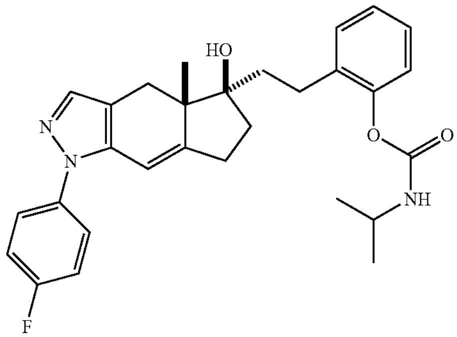 | 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl isopropylcarbamate | 490.2492 |
| 137 | 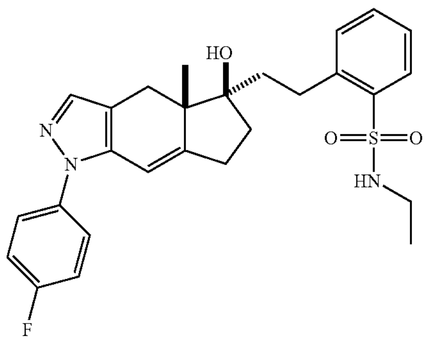 | N-ethyl-2-{2-[(4αS,5R)-1-(4-fluorophenyl)-5-hydroxy-4α-methyl-1,4,4α,5,6,7-hexahydrocyclopenta[f]indazol-5-yl]ethyl}benzenesulfonamide | 496.2086 |
| 138 | 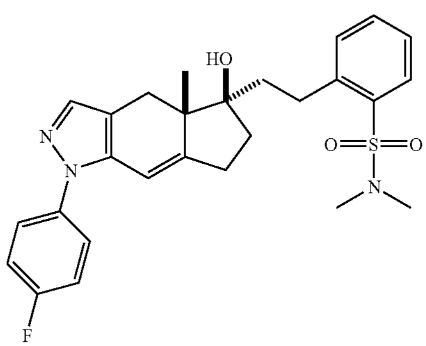 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N,N-dimethylbenzenesulfonamide | 496.2062 |
| 139 | 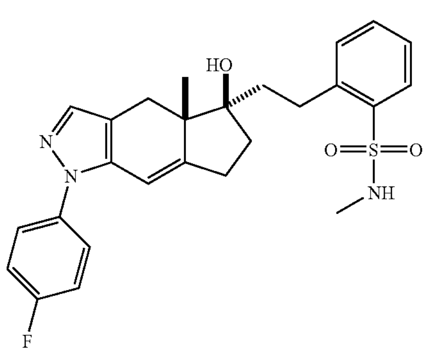 | 2-{2-[(4αS,5R)-1-(4-fluorophenyl)-5-hydroxy-4α-methyl-1,4,4α,5,6,7-hexahydrocyclopenta[f]indazol-5-yl]ethyl}-N-methylbenzenesulfonamide | 482.1904 |

| Ex. | STRUCTURE | NAME | M + 1 |
| --- | --- | --- | --- |
| 140 | 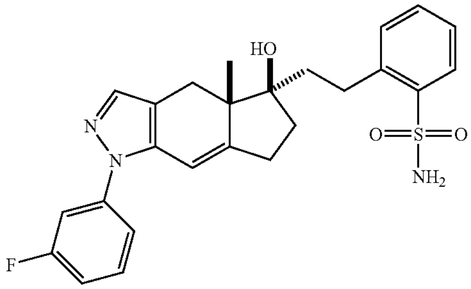 | 2-{2-[(4αS,5R)-1-(3-fluorophenyl)-5-hydroxy-4α-methyl-1,4,4α,5,6,7-hexahydrocyclopenta[f]indazol-5-yl]ethyl}benzenesulfonamide | 468.1752 |
| 141 | 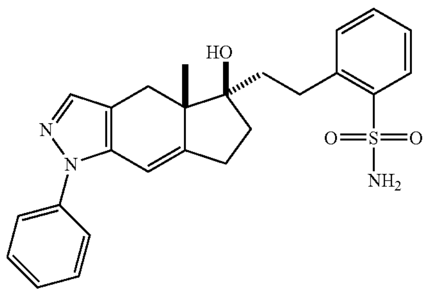 | 2-{2-[(4αS,5R)-5-hydroxy-4α-methyl-1-phenyl-1,4,4α,5,6,7-hexahydrocyclopenta[f]indazol-5-yl]ethyl}benzenesulfonamide | 450.1844 |
| 142 | 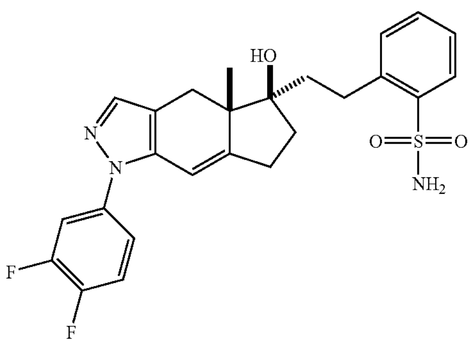 | 2-{2-[(4αS,5R)-1-(3,4-difluorophenyl)-5-hydroxy-4α-methyl-1,4,4α,5,6,7-hexahydrocyclopenta[f]indazol-5-yl]ethyl}benzenesulfonamide | 486.1653 |
| 143 | 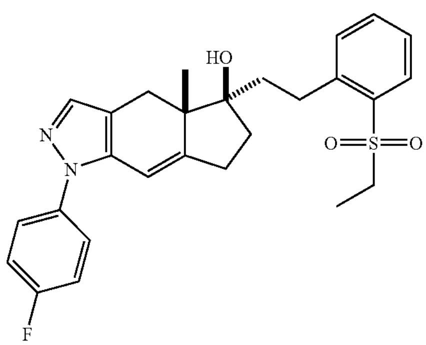 | (4αS,5R)-5-{2-[2-(ethylsulfonyl)phenyl]ethyl}-1-(4-fluorophenyl)-4α-methyl-1,4,4α,5,6,7-hexahydrocyclopenta[f]indazol-5-ol | 481.1964 |

| Ex. | STRUCTURE | NAME | M + 1 |
|---|---|---|---|
| 144 | 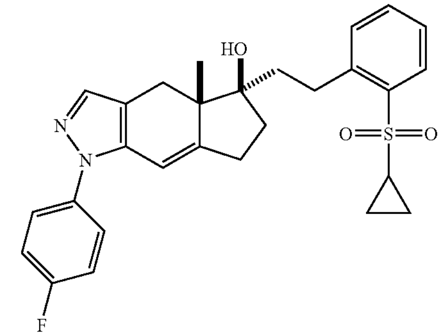 | (4αS,5R)-5-{2-[2-(cyclopropylsulfonyl)phenyl]ethyl}-1-(4-fluorophenyl)-4α-methyl-1,4,4α,5,6,7-hexahydrocyclopenta[f]indazol-5-ol | 444.1717 |
| 145 | 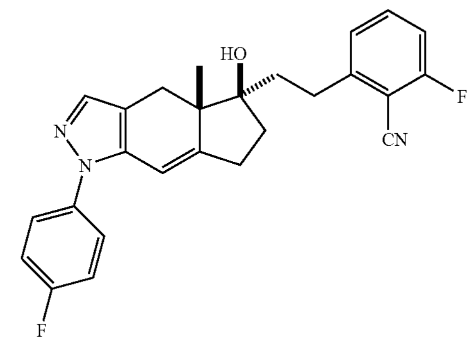 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile | 432.1885 |
| 146 | 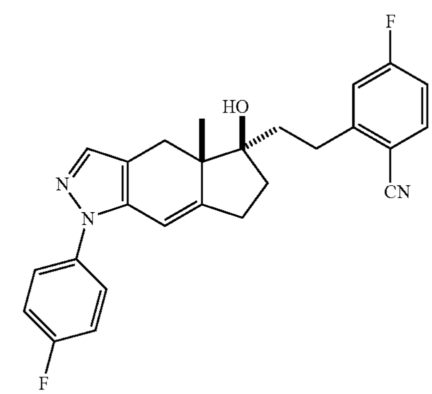 | 4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile | 432.1898 |
| 147 | 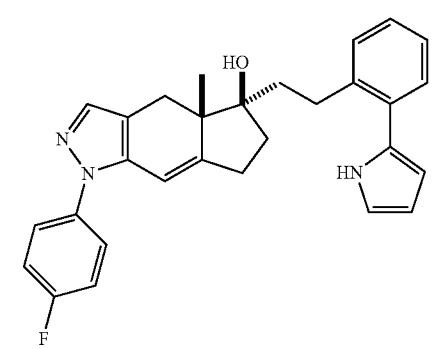 | (4αS,5R)-1-(4-fluorophenyl)-4α-methyl-5-{2-[2-(1H-pyrrol-2-yl)phenyl]ethyl}-1,4,4α,5,6,7-hexahydrocyclopenta[f]indazol-5-ol | 454.2277 |

| Ex. | STRUCTURE | NAME | M + 1 |
|---|---|---|---|
| 148 | 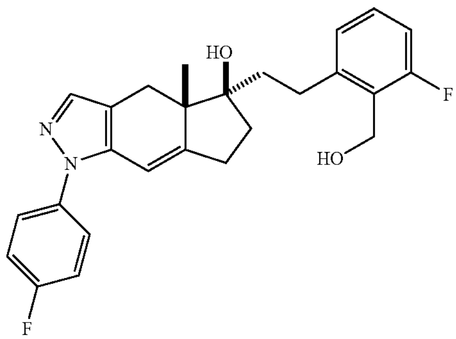 | (4αS,5R)-5-{2-[3-fluoro-2-(hydroxymethyl)phenyl]ethyl}-1-(4-fluorophenyl)-4α-methyl-1,4,4α,5,6,7-hexahydrocyclopenta[f]indazol-5-ol | 437.2026 |
| 149 | 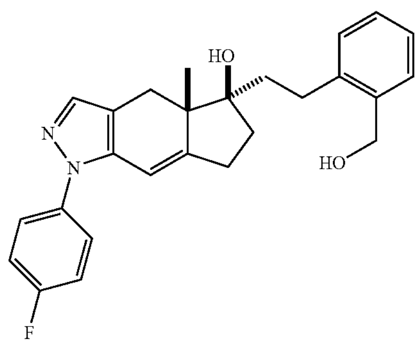 | (4αS,5R)-1-(4-fluorophenyl)-5-{2-[2-(hydroxymethyl)phenyl]ethyl}-4α-methyl-1,4,4α,5,6,7-hexahydrocyclopenta[f]indazol-5-ol | 419.2155 |
| 150 | 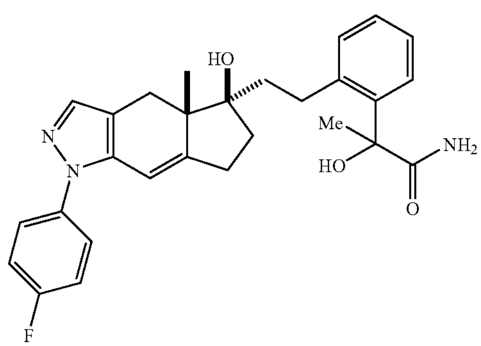 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxypropanamide | 476.2361 |
| 151 | 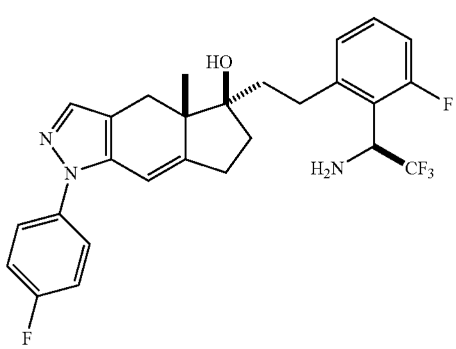 | (4αS,5R)-5-(2-{2-[(1S)-1-amino-2,2,2-trifluoroethyl]-3-fluorophenyl}ethyl)-1-(4-fluorophenyl)-4α-methyl-1,4,4α,5,6,7-hexahydrocyclopenta[f]indazol-5-ol | 504.2060 |

-continued

| Ex. | STRUCTURE | NAME | M + 1 |
|---|---|---|---|
| 152 | 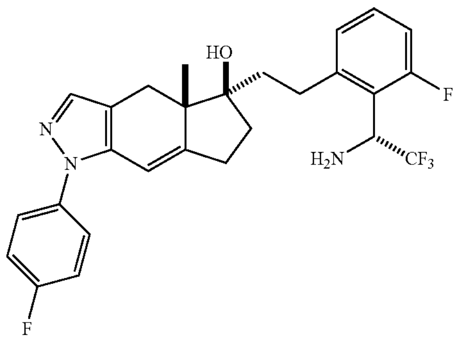 | (4αS,5R)-5-(2-{2-[(1R)-1-amino-2,2,2-trifluoroethyl]-3-fluorophenyl}ethyl)-1-(4-fluorophenyl)-4α-methyl-1,4,4α,5,6,7-hexahydrocyclopenta[f]indazol-5-ol | 504.2059 |
| 153 | 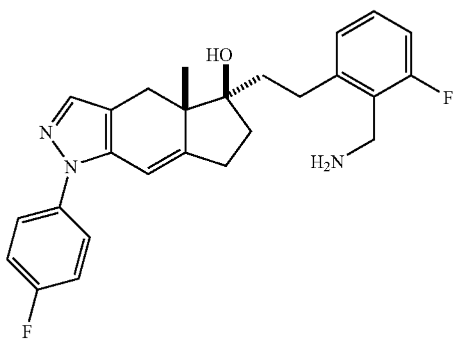 | (4αS,5R)-5-{2-[2-(aminomethyl)-3-fluorophenyl]ethyl}-1-(4-fluorophenyl)-4α-methyl-1,4,4α,5,6,7-hexahydrocyclopenta[f]indazol-5-ol | 436.2213 |
| 154 | 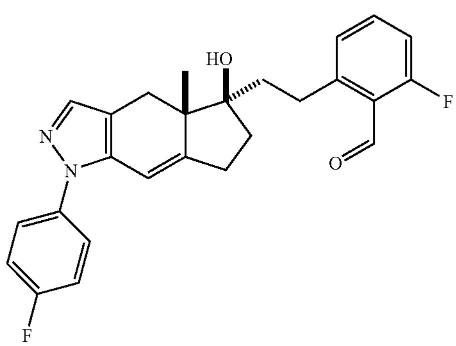 | 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzaldehyde | 435.1871 |
| 155 | 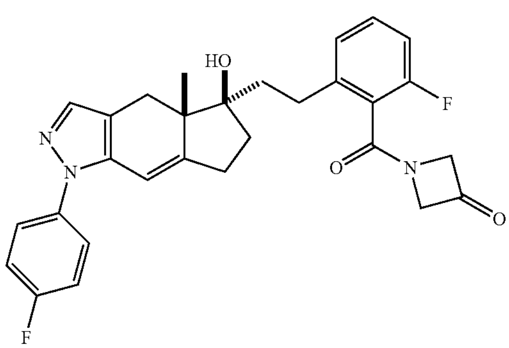 | 1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)azetidin-3-one | 504.2063 |

-continued

| Ex. | STRUCTURE | NAME | M + 1 |
|---|---|---|---|
| 156 | 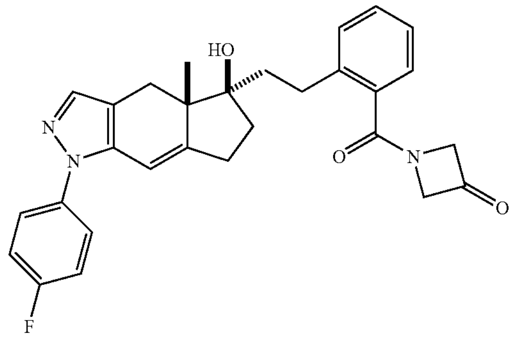 | 1-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)azetidin-3-one | 486.2162 |
| 157 | 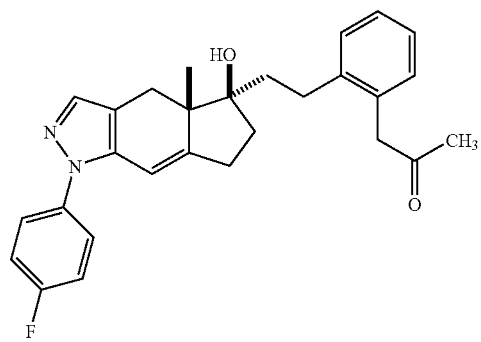 | 1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetone | 445.2285 |
| 158 | 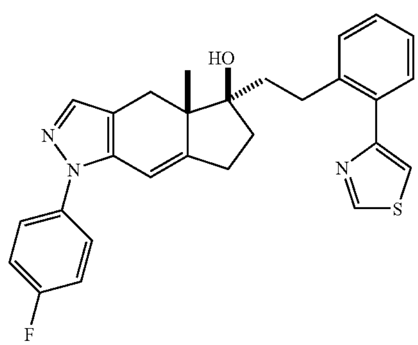 | (4αS,5R)-1-(4-fluorophenyl)-4α-methyl-5-{2-[2-[1,3-thiazol-4-yl)phenyl]ethyl}-1,4,4α,5,6,7-hexahydrocyclopenta[f]indazol-5-ol | 477.1848 |
| 159 | 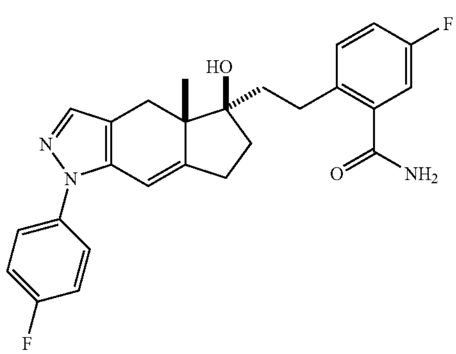 | 5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 450.1998 |

-continued

| Ex. | STRUCTURE | NAME | M + 1 |
|---|---|---|---|
| 160 | 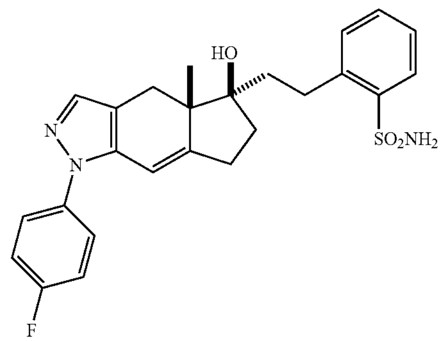 | 2-{(E)-2-[(4αS,5R)-1-(4-fluorophenyl)-5-hydroxy-4α-methyl-1,4,4α,5,6,7-hexahydrocyclopenta[f]indazol-5-yl]vinyl}benzenesulfonamide | 466.1593 |
| 161 | 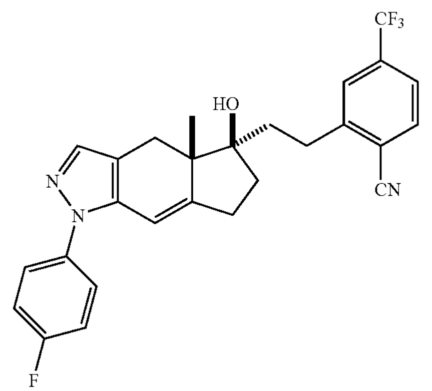 | 2-{2-[(4αS,5R)-1-(4-fluorophenyl)-5-hydroxy-4α-methyl-1,4,4α,5,6,7-hexahydrocyclopenta[f]indazol-5-yl]ethyl}-4-(trifluoromethyl)benzonitrile | 482.1841 |
| 162 | 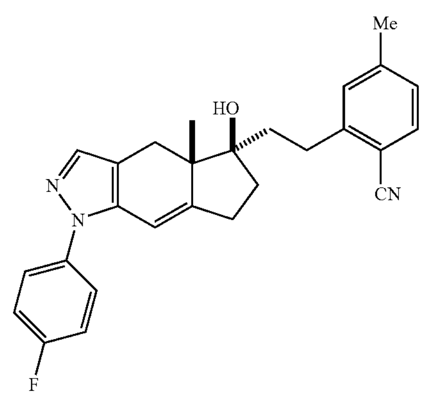 | 2-{2-[(4αS,5R)-1-(4-fluorophenyl)-5-hydroxy-4α-methyl-1,4,4α,5,6,7-hexahydrocyclopenta[f]indazol-5-yl]ethyl}-4-methylbenzonitrile | 428.2123 |
| 163 | 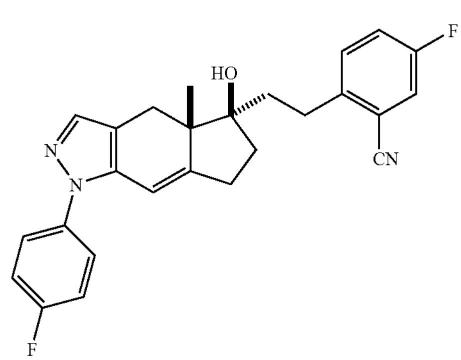 | 5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile | 432.1886 |

-continued

| Ex. | STRUCTURE | NAME | M + 1 |
|---|---|---|---|
| 164 | 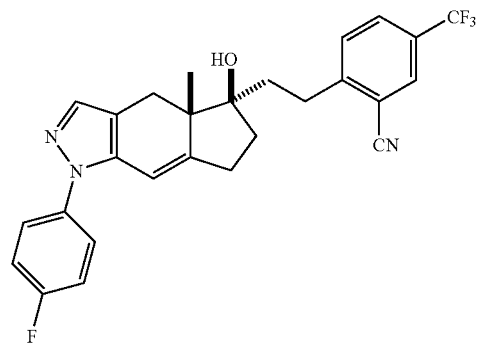 | 2-{2-[(4αS,5R)-1-(4-fluorophenyl)-5-hydroxy-4α-methyl-1,4,4α,5,6,7-hexahydrocyclopenta[f]indazol-5-yl]ethyl}-5-(trifluoromethyl)benzonitrile | 482.1845 |
| 165 | 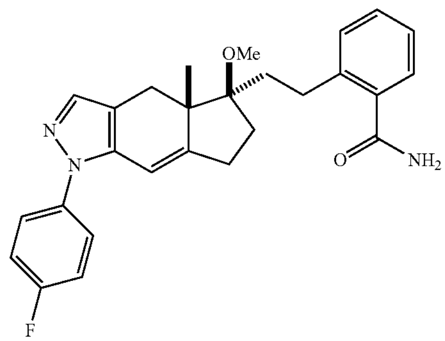 | 2-{2-[(4αS,5R)-1-(4-fluorophenyl)-5-methoxy-4α-methyl-1,4,4α,5,6,7-hexahydrocyclopenta[f]indazol-5-yl]ethyl}benzamide | 446.2252 |
| 166 | 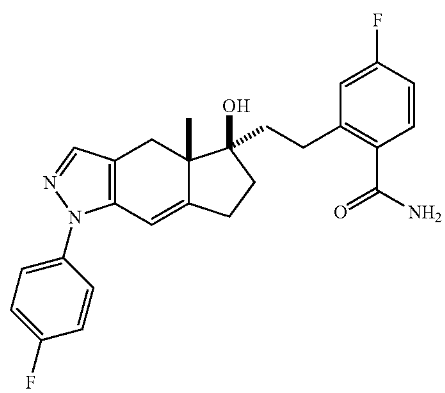 | 4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 450.1984 |
| 167 | 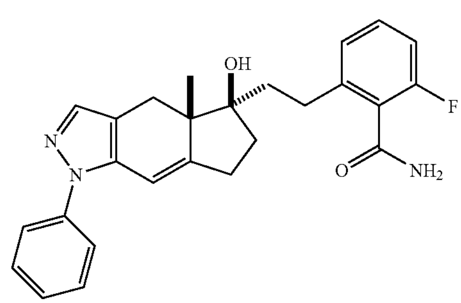 | 2-fluoro-6-{2-[(4αS,5R)-5-hydroxy-4α-methyl-1-phenyl-1,4,4α,5,6,7-hexahydrocyclopenta[f]indazol-5-yl]ethyl}benzamide | 432.2075 |

-continued

| Ex. | STRUCTURE | NAME | M + 1 |
|---|---|---|---|
| 168 | 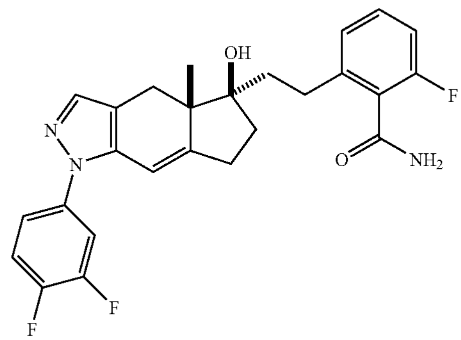 | 2-{2-[(4α,5R)-1-(3,4-difluorophenyl)-5-hydroxy-4α-methyl-1,4,4α,5,6,7-hexahydrocyclopenta[f]indazol-5-yl]ethyl}-6-fluorobenzamide | 468.1889 |
| 169 | 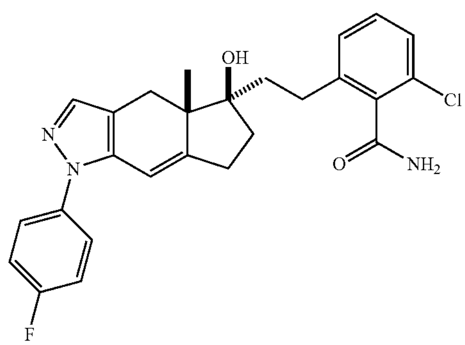 | 2-chloro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 466.1692 |
| 170 | 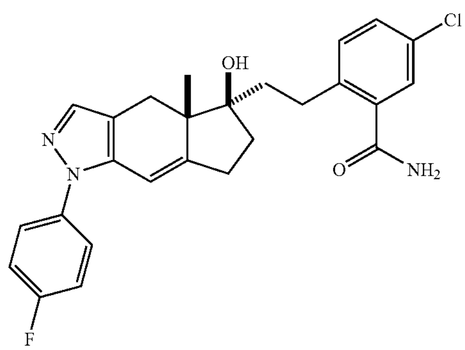 | 5-chloro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 466.1693 |
| 171 | 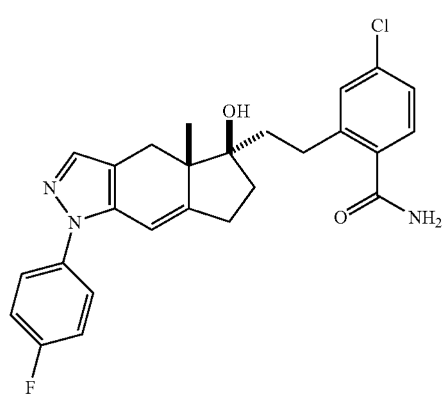 | 4-chloro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 466.1690 |

-continued

| Ex. | STRUCTURE | NAME | M + 1 |
|---|---|---|---|
| 172 | 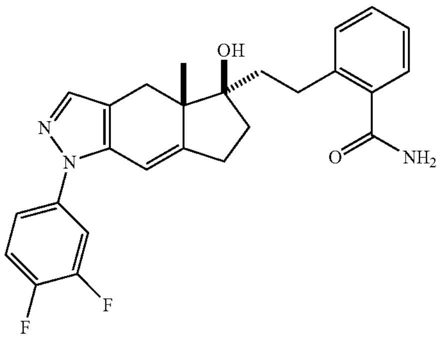 | 2-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide | 450.1992 |
| 173 | 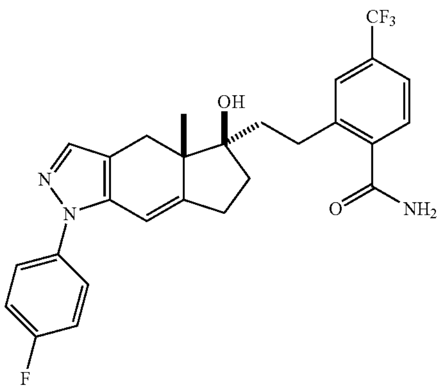 | 2-{2-[(4α6,5R)-1-(4-fluorophenyl)-5-hydroxy-4α-methyl-1,4,4α,5,6,7-hexahydrocyclopenta[f]indazol-5-yl]ethyl}-4-(trifluoromethyl)benzamide | 500.1961 |
| 174 | 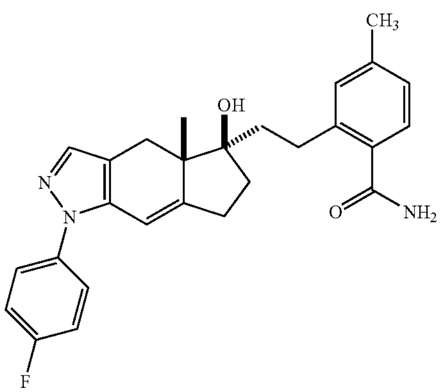 | 2-{2-[(4αS,5R)-1-(4-fluorophenyl)-5-hydroxy-4α-methyl-1,4,4α,5,6,7-hexahydrocyclopenta[f]indazol-5-yl]ethyl}-4-methylbenzamide | 446.2242 |
| 175 | 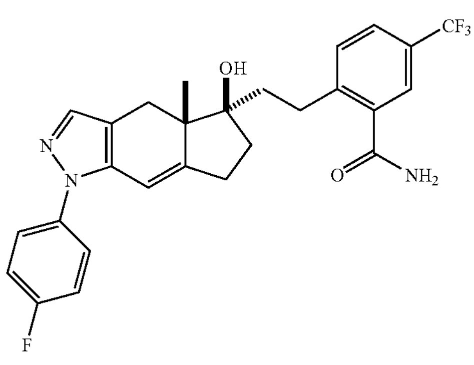 | 2-{2-[(4αS,5R)-1-(4-fluorophenyl)-5-hydroxy-4α-methyl-1,4,4α,5,6,7-hexahydrocyclopenta[f]indazol-5-yl]ethyl}-5-(trifluoromethyl)benzamide | 500.1959 |

-continued

| Ex. | STRUCTURE | NAME | M + 1 |
|---|---|---|---|
| 176 | 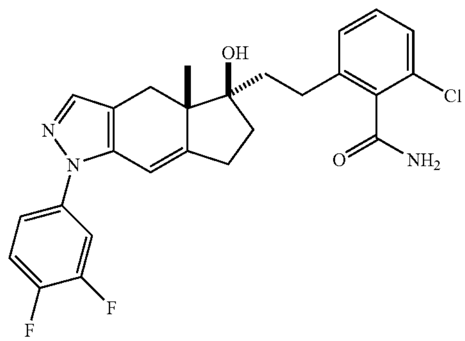 | 2-chloro-6-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide | 484.1605 |
| 177 | 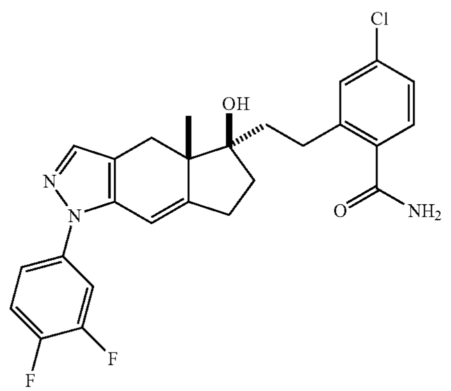 | 4-chloro-2-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide | 484.1582 |
| 178 | 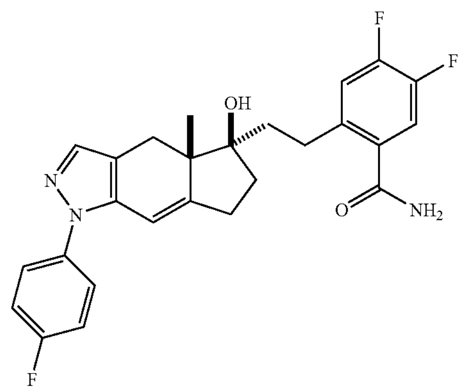 | 4,5-difluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 468.1890 |
| 179 | 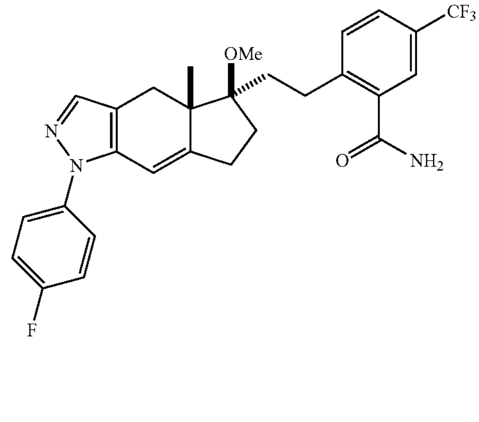 | 2-{2-[(4αS,5R)-1-(4-fluorophenyl)-5-methoxy-4α-methyl-1,4,4α,5,6,7-hexahydrocyclopenta[f]indazol-5-yl]ethyl}-5-(trifluoromethyl)benzamide | 500.1959 |

-continued

| Ex. | STRUCTURE | NAME | M + 1 |
|---|---|---|---|
| 180 | 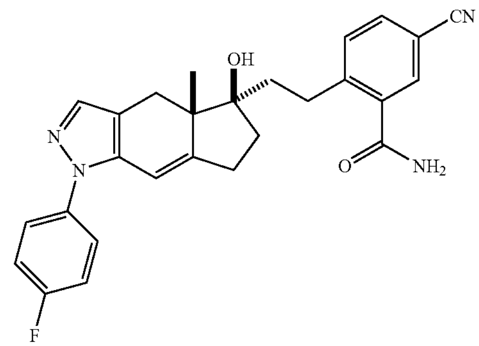 | 5-cyano-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 457.2048 |
| 181 | 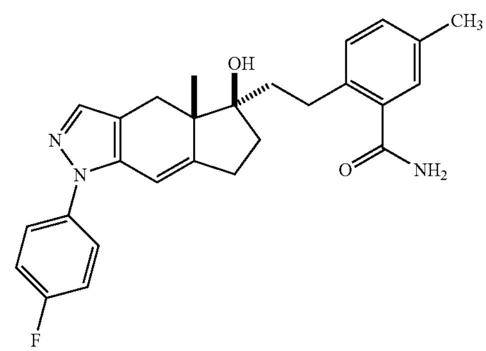 | 2-{2-[(4αS,5R)-1-(4-fluorophenyl)-5-hydroxy-4α-methyl-1,4,4α,5,6,7-hexahydrocyclopenta[f]indazol-5-yl]ethyl}-5-methylbenzamide | 446.2262 |
| 182 | 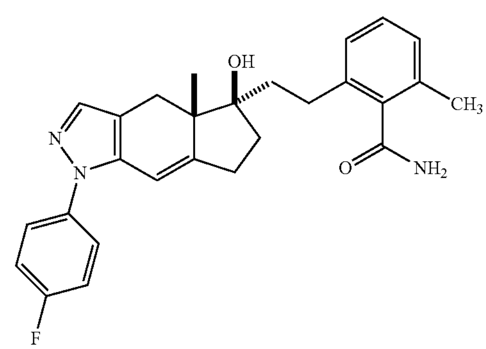 | 2-{2-[(4αS,5R)-1-(4-fluorophenyl)-5-hydroxy-4α-methyl-1,4,4α,5,6,7-hexahydrocyclopenta[f]indazol-5-yl]ethyl}-6-methylbenzamide | 446.2263 |
| 183 | 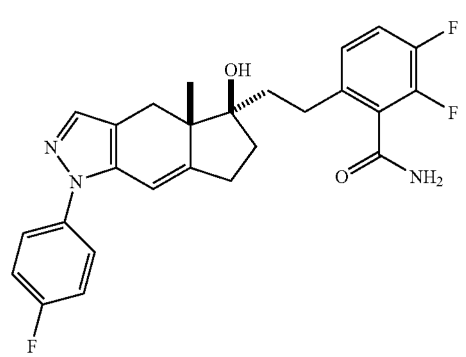 | 2,3-difluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide | 468.1912 |

| Ex. | STRUCTURE | NAME | M + 1 |
|---|---|---|---|
| 184 | 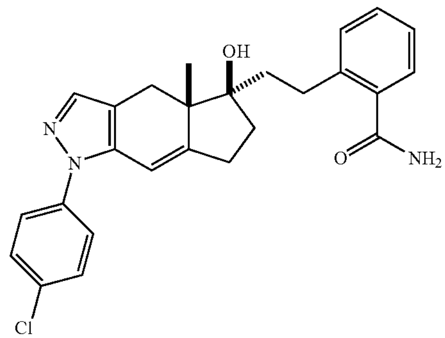 | 2-{2-[(4αS,5R)-1-(4-chlorophenyl)-5-hydroxy-4α-methyl-1,4,4α,5,6,7-hexahydrocyclopenta[f]indazol-5-yl]ethyl}benzamide | 448.1805 |
| 185 | 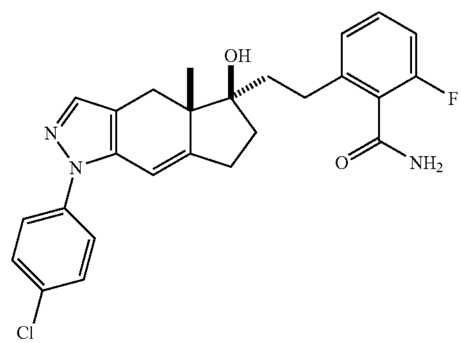 | 2-{2-[(4αS,5R)-1-(4-chlorophenyl)-5-hydroxy-4α-methyl-1,4,4α,5,6,7-hexahydrocyclopenta[f]indazol-5-yl]ethyl}-6-fluorobenzamide | 466.1721 |
| 186 | 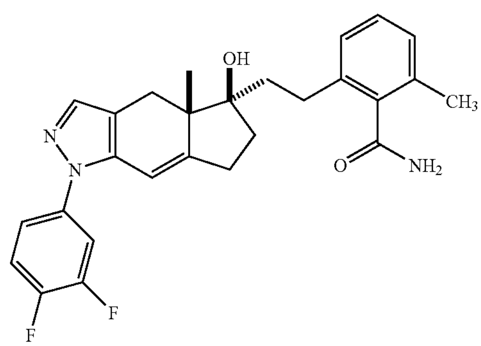 | 2-{2-[(4αS,5R)-1-(3,4-difluorophenyl)-5-hydroxy-4α-methyl-1,4,4α,5,6,7-hexahydrocyclopenta[f]indazol-5-yl]ethyl}-6-methylbenzamide | 464.2172 |
| 187 | 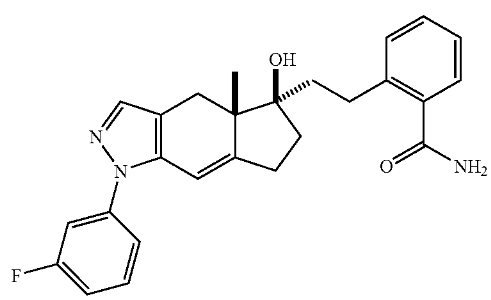 | 2-{2-[(4αS,5R)-1-(3-fluorophenyl)-5-hydroxy-4α-methyl-1,4,4α,5,6,7-hexahydrocyclopenta[f]indazol-5-yl]ethyl}benzamide | 432.2082 |

-continued

| Ex. | STRUCTURE | NAME | M + 1 |
|---|---|---|---|
| 188 | 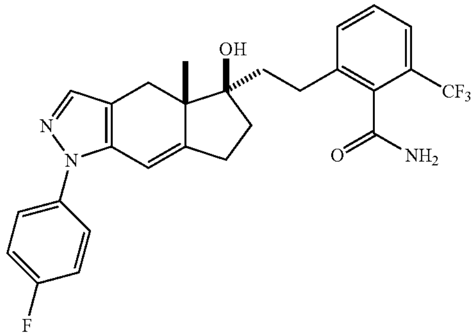 | 2-{2-[(4αS,5R)-1-(4-fluorophenyl)-5-hydroxy-4α-methyl-1,4,4α,5,6,7-hexahydrocyclopenta[f]indazol-5-yl]ethyl}-6-(trifluoromethyl)benzamide | 500.1956 |
| 189 | 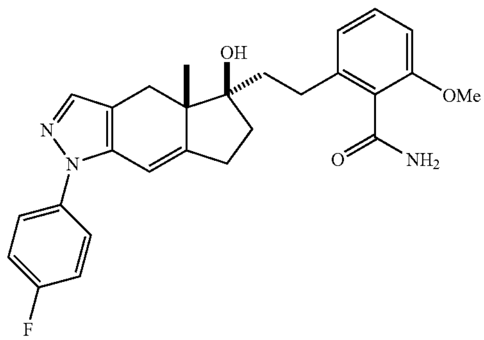 | 2-{2-[(4αS,5R)-1-(4-fluorophenyl)-5-hydroxy-4α-methyl-1,4,4α,5,6,7-hexahydrocyclopenta[f]indazol-5-yl]ethyl}-6-methoxybenzamide | 462.2182 |
| 190 | 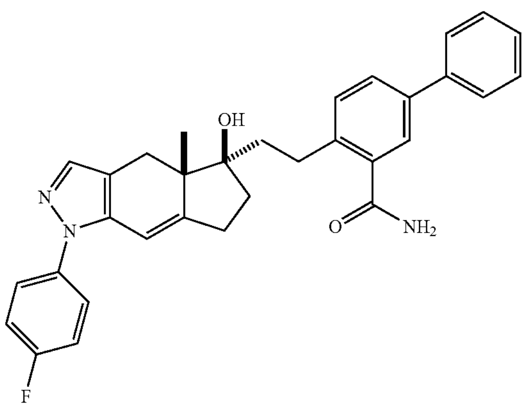 | 4-{2-[(4αS,5R)-1-(4-fluorophenyl)-5-hydroxy-4α-methyl-1,4,4α,5,6,7-hexahydrocyclopenta[f]indazol-5-yl]ethyl}biphenyl-3-carboxamide | 508.2395 |
| 191 | 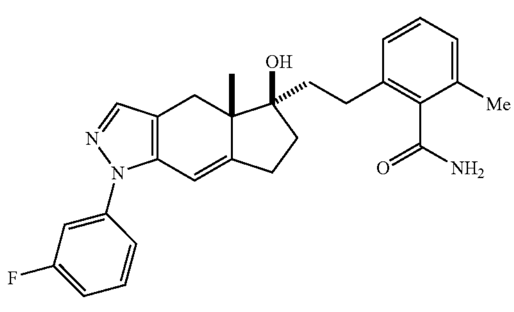 | 2-{2-[(4αS,5R)-1-(3-fluorophenyl)-5-hydroxy-4α-methyl-1,4,4α,5,6,7-hexahydrocyclopenta[f]indazol-5-yl]ethyl}-6-methylbenzamide | 446.2223 |

| Ex. | STRUCTURE | NAME | M + 1 |
|---|---|---|---|
| 192 | 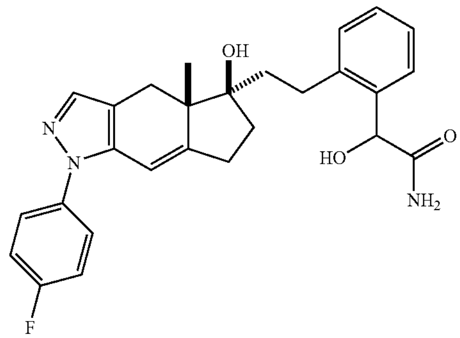 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxyacetamide | 462.2179 |
| 193 | 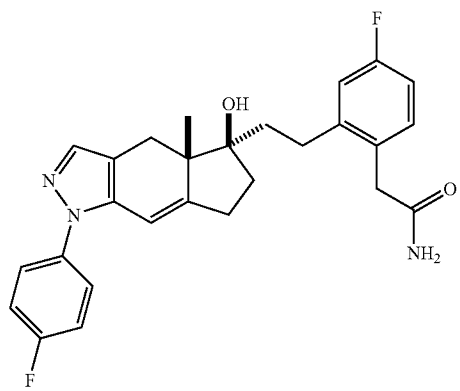 | 2-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 464.2148 |
| 194 | 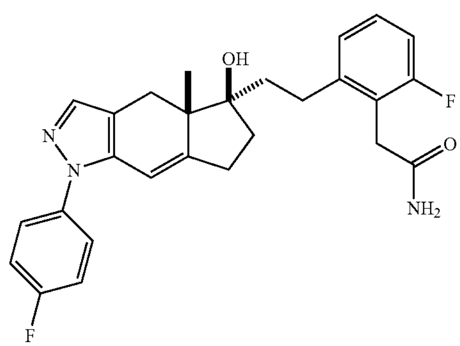 | 2-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 464.2150 |
| 195 | 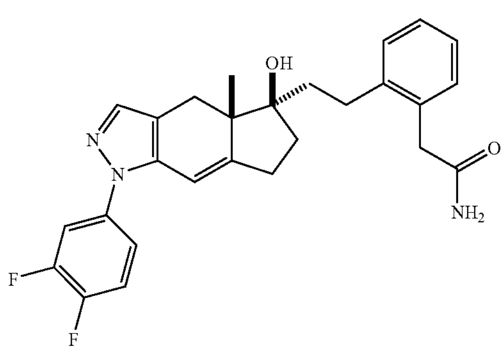 | 2-(2-{2-[(4αS,5R)-1-(3,4-difluorophenyl)-5-hydroxy-4α-methyl-1,4,4α,5,6,7-hexahydrocyclopenta[f]indazol-5-yl]ethyl}phenyl)acetamide | 464.2119 |

-continued

| Ex. | STRUCTURE | NAME | M + 1 |
|---|---|---|---|
| 196 | 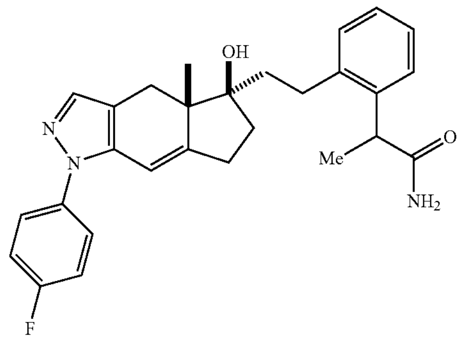 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)propanamide | 460.2373 |
| 197 | 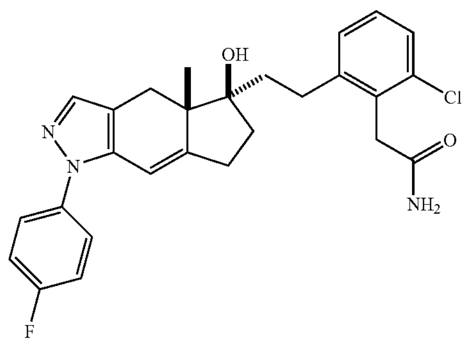 | 2-(2-chloro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 480.1823 |
| 198 | 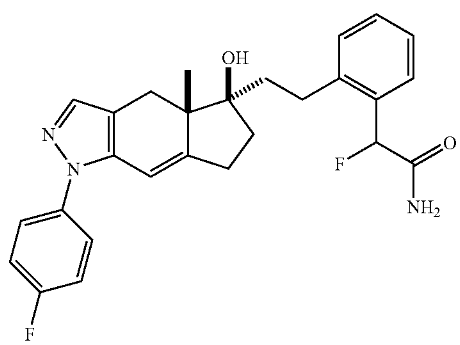 | 2-fluoro-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide | 464.2122 |
| 199 | 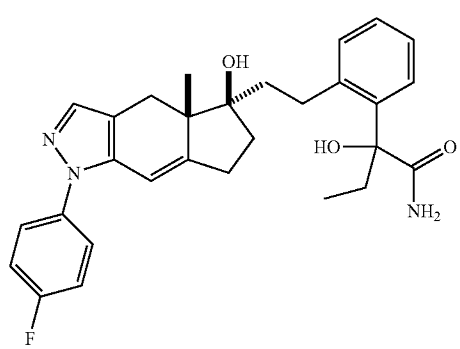 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxybutanamide | 490.2472 |

| Ex. | STRUCTURE | NAME | M + 1 |
|---|---|---|---|
| 200 | 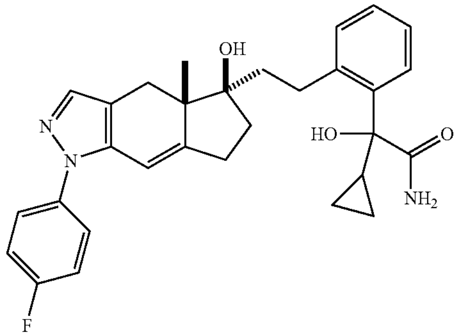 | 2-cyclopropyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxyacetamide | 502.2478 |
| 201 | 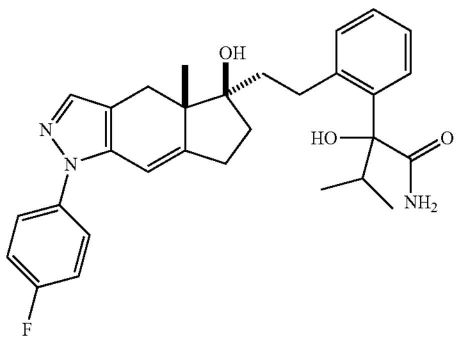 | 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxy-3-methylbutanamide | 504.2631 |

Biological Evaluation

The compounds exemplified in the present application exhibited activity in one or more of the following assays.

Ligand Binding Assay

Materials:

Binding Buffer: TEGM (10 mM Tris-HCl, 1 mM EDTA, 10% glycerol, 1 mM beta-mercaptoethanol, 10 mM Sodium Molybdate, pH 7.2)

50% HAP Slurry: Calbiochem Hydroxylapatite, Fast Flow, in 10 mM Tris, pH 8.0 and 1 mM EDTA.

Wash Buffer: 40 mM Tris, pH7.5, 100 mM KCl, 1 mM EDTA and 1 mM EGTA.

95% EtOH

Dexmethasone-methyl-$^3$H, (DEX*); (Amersham cat# TRK645)

Dexamethasone (DEX) (Sigma, cat# D1756):

Hydroxylapatite Fast Flow; Calbiochem Cat#391947

Molybdate=Molybdic Acid (Sigma, M1651)

HeLa cell culture media:

| RPMI 1640 (Gibco 11835-055) w/23.8 mM NaHCO$_3$, 2 mM L-glutamine | |
|---|---|
| in 500 mL of complete media | Final conc. |
| 10 mL (1M Hepes) | 20 mM |
| 5 mL (200 mM L-glu) | 4 mM |
| 0.5 mL (10 mg/mL human insulin) in 0.01 N HCl Calbiochem#407694-S) | 10 μg/mL |
| 50 mL FBS (Sigma F2442) | 10% |
| 1 mL (10 mg/mL Gentamicin Gibco#15710-072) | 20 μg/mL |

Cell Passaging

Cells (Hall R. E., et al., *European Journal of Cancer*, 30A: 484-490 (1994)) HeLa (ATCC) cultured in RPMI 1640 (Gibco 11835-055) containing 20 mM Hepes, 4 mM L-glu, 10 ug/ml of human insulin (Sigma, I-0259), 10% FBS and 20 ug/ml of Gentamicin (Gibco #15710-072) are rinsed twice in PBS. Phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added. The cells are counted at this point, then diluted to the appropriate concentration and split into flasks or dishes for further culturing (Usually 1:3 to 1:6 dilution).

Preparation of Hela Cell Lysate

When the cells are 70 to 85% confluent, they are detached as described above, and collected by centrifuging at 1000 g for 10 minutes at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of 10$^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 μL of supernatant, the test compound can be prepared in 50 μL of the TEGM buffer.

Procedure for Multiple Compound Screening

1×TEGM buffer is prepared, and the isotope-containing assay mixture is prepared in the following order: EtOH (2% final concentration in reaction), 3H-DEX (Amersham Biosciences) and 1×TEGM. [e.g. For 100 samples, 200 µL (100× 2) of EtOH+4.25 µL of 1:10 $^3$H-Dex stock+2300 µL (100×23) 1×TEGM]. The compound is serially diluted, e.g., if starting final conc. is 1 µM, and the compound is in 25 µL of solution, for duplicate samples, 75 µL of 4×1 µM solution is made and 3 µL of 100 µM is added to 72 µL of buffer, and 1:5 serial dilution.

25 µL of $^3$H-DEX (6 nM) trace and 25 µL compound solution are first mixed together, followed by addition of 50 µL receptor solution. The reaction is gently mixed, spun briefly at about 200 rpm and incubated at 4° C. overnight. 100 µL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 µL of MICROSCINT (Packard) scintillant for 30 minutes before being counted on the TopCount microscintillation counter (Packard). $IC_{50}$s are calculated using DEX as a reference.

Examples 1 to 201 were tested in the ligand binding assay and demonstrated IC50s less than 1000 nM.

Trans-Activation Modulation of Glucocorticoid Receptor (GRAMMER)

This assay assesses the ability of test compounds to control transcription from the MMTV-LUC reporter gene in lung adenocarcinoma A549 cells or HeLa cells, a human breast cancer cell line that naturally expresses the human GR. The assay measures induction of a modified MMTV LTR/promoter linked to the LUC reporter gene.

The routine transient assay consists of plating 7,000-25,000 cells/well of a white, clear-bottom 96-well plate. Alternatively, 384-well plates can be used at a cell concentration of 10,000/well. The media that the cells are plated in is "exponential growth medium" which consists of phenol red-free RPMI1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media. It is then gently mixed with the FuGene6/DNA mix and plated onto the 96 or 384-well plate, all the wells receive 100 uL or 40 uL, respectively, of medium+lipid/DNA complex then incubated 37° C. overnight. The transfection cocktail consists of serum-free OptiMEM, FuGene6 reagent and DNA. The manufacturer's (Roche Biochemical) protocol for cocktail setup is as follows: The lipid to DNA ratio is approximately 2.5:1 and the incubation time is 20 min at room temperature. Sixteen to 24 hours after transfection, the cells are treated with dexamethasone to a final concentration of 10 nM as well as the compound of interest, such that final DMSO (vehicle) concentration is equal to or less than 1%. Each plate also contains samples that are treated with 10 nM dexamethasone alone, which is used as the 100% activity control. The cells are exposed to the compounds for 24 hours. After 24 hours, the cells are lysed by a Promega cell culture lysis buffer for approximately 30 min and then the luciferase activity in the extracts is assayed in the 96-well format luminometer. In 384-well format, Steady-Glo (Promega) or Steady-Lite (PerkinElmer) can be used by adding an equal volume of reagent to the media present in each well. Activity induced by 10 nM dexamethasone alone is set at 100% activity. Antagonist activity is calculated by determining the decrease in dexamethasone-induced activity in response to compound treatment relative to samples that were treated with dexamethasone alone. Results are expressed as % inhibition of 10 nM dexamethasone activity or as fold of 10 nM dexamethasone activity. This transactivation assay can be performed in an agonist and antagonist mode to identify these different activities.

Activity of test compounds is calculated as the $E_{max}$ relative to the activity obtained with 300 nM dexamethasone. Activity of test compounds is calculated as the $E_{max}$ relative to the activity obtained with 300 nM DEX. The exemplified tissue selective glucocorticoid receptor modulators of the present invention display agonist activity in this assay of greater than 5% and less than 100%, and maximal transactivation activity less then maximal transrepression activity.

The action of compounds is also tested in an antagonist mode (Anti-GRAMMER) in which the cells are treated with medium containing an agonist such as 10 nM DEX and the ability of agents to inhibit the activation by an agonist is measured.

Transrepression Assay (GITAR)

This assay assesses the ability of test compounds to control transcription from the TNFα-β-lactamase reporter gene in U937 cells, a human myelomonocytic leukemia cell line that naturally expresses the human GR. The assay measures compound dependent-repression of the TNFa promoter linked to a reporter gene.

The human U937 cells that had been stably transfected with the TNF-α promoter driving β-lactamase are used for this assay. U937 cells contain an endogenous glucocorticoid receptor (GR). Cells are maintained in RPMI 1640 Growth medium (Gibco Cat#11875-093) containing 25 mM HEPES, 10% FBS, 2 mM L-Glutamine, 1 mM Sodium pyruvate, 25 µg/ml Gentamicin (Gibco Cat#15710-064), 1:1000 2-Mercaptoethanol (Gibco Cat#21985-023) and 0.8 mg/ml G418 (Gibco Cat#10131-027). The density of the cells in the flask needs to be about 1×106-3×106/ml at the time of harvest. Usually, the cells are split to 1.2~1.4×105/ml (1:10) 3 days prior to the assay. 50,000 cells/well are plated in 96 well black-walled plates the day of assay. Test compounds are added 10 µL/well, and cells are incubated at 37° C. for 30~45 min. For assaying compounds, first dilute 1:10 in DMSO to make 1 mM, then further dilute 1:100 in medium to make 10× stock prior to adding to the cells. Add 50 ng/ml PMA (Sigma, cat# P8139) 10 µL/well to a final concentration 5 ng/ml, and 1 µg/ml LPS (Sigma, cat# L4130) 10 µL/well to a final concentration 100 ng/ml. Incubate cells at 370 C overnight for ~18 hr. PMA is stored frozen as 100 µg/ml stock in DMSO. Dilute 1:10 in DMSO for a working stock of 10 µg/ml and store at −20 C. For assaying, dilute the 10 µg/ml working stock 1:200 in medium to make a 10× solution (50 ng/ml). Store frozen LPS at 1 mg/ml in PBS, dilute 1:1000 in medium to make 10× (1 µg/ml) for the assay. Add 6× loading buffer (CCF2-AM) 20 µL/well, and incubate at room temperature for 70~90 min. Read plates on CytoFluor II Plate Reader according to manufacture suggested protocols. The activity repressed by 100 nM dexamethasone alone is set as 100% activity.

Examples 1 to 201 were tested in the transrepression assay and demonstrated maximal activity greater than 5% and less than 100% and maximal transactivation activity less then maximal transrepression activity.

Microarray Analysis

This assay assesses the ability of test compounds to modulate the transcription of endogenously expressed genes in a variety of cell types including but not limited to A549, HeLa or U937 cells. All cell culture reagents were purchased from Invitrogen Life Tech, Carlsbad Calif. A549 cells were grown in phenol red-free DMEM/F12 medium supplemented with 10% FBS. Cells were grown at 37° C. with 5% CO2. Using the RNeasy Kit (Qiagen Corp, Valencia Calif.), total RNA was extracted and purified from A549 cells treated with different GC compounds for 24 hours, at a fully active dose. These cells express large amount of the GR and are very responsive to GC treatment. All samples were compared against cells treated with vehicle. Expression levels of 23000 genes were measured using oligonucleotide microarrays purchased from Agilent Technologies, Inc. Each comparison was done on a pair of microarrays with reversed fluorophores. Raw image intensity data were processed according to the method described in U.S. Pat. No. 6,351,712. The method was used to remove dye bias and to derive a Rosetta probability (p) and fold change value for each gene and each sample pair. Furthermore, for each gene an ANOVA model was constructed across all treatments to derive error estimates. P values for evaluating expression differences were computed using a Bayesian adjusted t-test that was developed by Lönnstedt and Speed (2002) and extended by Smyth (2003). A gene was declared differentially expressed in any particular comparison if it satisfied two criteria:

1. The Rosetta p value had to be less than 0.1 and the Rosetta fold change value had to be greater than 1.4 in at least one of the treatments.

2. The ANOVA p value had to be less than 0.01 and the fold change greater than 2 in the comparison under consideration.

In Vivo Inflammation Assay

Intact adult (6 month old) female Sprague-Dawley rats are used in the oxazolone (OX) contact dermatitis model. Rats were sensitized on the ventral abdomen with OX on Day 0. On Days 7 and 9, a randomly-selected ear was challenged (same ear each time) with OX; the other was treated with vehicle. Daily treatment begun on Day 7 and continued for 7d with test compounds at different doses and 1.3 mpk 6-methylprednisolone or 0.1 mpk DEX as positive controls. The thickness of both ears are measured on Days 11 and 14. Necropsy occurred on Day 14. The rat is first weighed, then anesthetized in a $CO_2$ chamber until near death. Approximately 5 ml whole blood is obtained by cardiac puncture. The rat is then examined for certain signs of death and completeness. Tissues are dissected in a highly stylized fashion. The following endpoints were evaluated: a) inhibiting ear inflammation induced by oxazolone, b) raising serum insulin, c) reducing serum ACTH, d) reducing spleen weight, e) reducing skin thickness, f) reducing body weight, g) increasing expression of bone-related genes with potential relationship to negative glucocorticoid effects on bone; e) changes in molecular markers that correlate with skin inflammation, skin thinning, muscle atrophy and glucose metabolism in liver. All blood samples were collected between 1330-1530 hours, ~4-5 hrs after the last compound treatment.

Primary data for this assay are left and right ear thickness. Inter-ear thickness difference (etd) is used for the estimating the level of inflammation and effectiveness of the compounds is determined by their ability to reduce the increase the thickness of the inflamed ear. Back of the rat skin thickness, spleen weight, serum insulin as well as the effects of gcs on the expression of molecular markers in skin inflammation, skin atrophy, muscle atrophy and glucose metabolism in liver are measured. Data are analyzed by anova plus fisher plsd post-hoc test to identify intergroup differences.

Results

As stated above, Examples 1 to 201 demonstrated IC50s less than 1000 nM in the ligand binding assay, maximal activity greater than 5% and less than 100% in the transrepression assay and maximal transactivation activity less then maximal transrepression activity. A subset of compounds has been discovered having a superior activity profile as shown in Table 1 below. The compounds shown in Table 1 have potencies in the GRAMMER and GITAR assays (as measured by inflection points, IP) of less than 300 nM concomitant with maximum activity in the GRAMMER assay of less than 60% and maximum activity in the GITAR assay of between 40 and 80%. The examples not shown in Table 1 had activity profiles outside this criterion.

Compounds in the range of activities described above offer potential improvements over fuller agonists (higher Emaxes) as they may have less side effects as demonstrated in preclinical models. Among the compounds with the described range of activities, different selectivity profiles may be observed in different animal models, which model the side effects of diabetes and glucose intolerance, skin and muscle atrophy, intraocular pressure, bone degradation, and hypertension. Compounds shown in Table 1 have demonstrated, or have the potential for such selectivity.

TABLE 1

| Example | GR BIND Ki (nM) | Transactivation A549 Cells GRAMMER | | Transrepression U937 Cells GITAR | | GITAR > GRAMM |
|---|---|---|---|---|---|---|
| | | IP (nM) | Emax (%) | IP (nM) | Emax (%) | % SEP |
| 2 | 2.08 | 39 | 51 | 88 | 65 | 14 |
| 5 | 0.44 | 138 | 40 | 179 | 64 | 24 |
| 11 | 2.37 | 290 | 39 | 208 | 57 | 17 |
| 14 | 6.38 | 175 | 55 | 193 | 79 | 23 |
| 15 | 1.17 | 236 | 43 | 242 | 79 | 36 |
| 19 | 1.13 | 127 | 46 | 187 | 79 | 33 |
| 23 | 5.09 | 268 | 36 | 263 | 73 | 37 |
| 26 | 1.37 | 39 | 24 | 123 | 39 | 15 |
| 28 | 3.55 | 48 | 28 | 65 | 72 | 43 |
| 29 | 1.14 | 95 | 24 | 190 | 61 | 37 |
| 30 | 1.52 | 81 | 29 | 127 | 50 | 21 |
| 31 | 0.90 | 93 | 9 | 183 | 48 | 39 |
| 32 | 0.49 | 134 | 13 | 277 | 49 | 36 |
| 33 | 1.13 | 62 | 37 | 123 | 62 | 25 |
| 34 | 5.29 | 128 | 13 | 208 | 54 | 41 |
| 35 | 3.55 | 60 | 48 | 170 | 62 | 14 |
| 37 | 0.44 | 65 | 57 | 81 | 58 | 1 |
| 38 | 0.43 | 91 | 15 | 152 | 58 | 44 |
| 40 | 6.14 | 231 | 46 | 246 | 64 | 17 |
| 41 | 0.83 | 46 | 18 | 115 | 62 | 44 |
| 42 | 2.79 | 74 | 51 | 122 | 64 | 13 |
| 43 | 5.16 | 111 | 59 | 98 | 68 | 9 |
| 44 | 0.60 | 95 | 24 | 119 | 67 | 43 |
| 45 | 1.02 | 183 | 18 | 220 | 70 | 52 |
| 46 | 3.02 | 176 | 54 | 248 | 70 | 17 |
| 47 | 11.53 | 196 | 59 | 205 | 71 | 12 |
| 48 | 1.20 | 94 | 13 | 198 | 72 | 59 |
| 49 | 0.81 | 26 | 25 | 30 | 72 | 47 |
| 51 | 7.05 | 164 | 30 | 193 | 73 | 42 |
| 52 | 0.80 | 21 | 45 | 154 | 74 | 29 |
| 55 | 0.92 | 173 | 23 | 187 | 76 | 53 |
| 57 | 0.61 | 24 | 37 | 30 | 77 | 40 |
| 59 | 1.83 | 108 | 40 | 95 | 77 | 37 |
| 61 | 0.58 | 86 | 35 | 83 | 79 | 44 |
| 62 | 9.58 | 212 | 23 | 246 | 79 | 56 |
| 83 | 0.56 | 70 | 21 | 94 | 54 | 33 |
| 84 | 0.62 | 50 | 23 | 96 | 60 | 37 |
| 85 | 0.31 | 94 | 19 | 182 | 63 | 44 |
| 86 | 0.51 | 211 | 13 | 246 | 66 | 53 |
| 88 | 0.57 | 53 | 32 | 90 | 69 | 37 |
| 89 | 0.40 | 43 | 20 | 64 | 70 | 50 |
| 91 | 0.26 | 121 | 46 | 231 | 72 | 26 |
| 107 | 2.32 | 261 | 37 | 217 | 66 | 29 |
| 113 | 2.66 | 205 | 32 | 207 | 71 | 39 |
| 114 | 2.77 | 221 | 43 | 199 | 78 | 34 |

TABLE 1-continued

| Example | GR BIND Ki (nM) | Transactivation A549 Cells GRAMMER IP (nM) | Emax (%) | Transrepression U937 Cells GITAR IP (nM) | Emax (%) | GITAR > GRAMM % SEP |
|---|---|---|---|---|---|---|
| 138 | 0.84 | 137 | 55 | 212 | 72 | 17 |
| 143 | 1.44 | 118 | 41 | 194 | 70 | 29 |
| 144 | 1.32 | 268 | 40 | 212 | 70 | 30 |
| 148 | 0.67 | 43 | 57 | 46 | 75 | 18 |
| 150 | 11.00 | 264 | 38 | 210 | 67 | 29 |
| 151 | 1.74 | 170 | 43 | 207 | 76 | 33 |
| 152 | 2.60 | 223 | 44 | 247 | 77 | 34 |
| 156 | 2.90 | 278 | 47 | 189 | 69 | 22 |
| 157 | 1.50 | 240 | 45 | 194 | 63 | 18 |
| 159 | 2.96 | 197 | 37 | 125 | 73 | 36 |
| 160 | 0.94 | 118 | 30 | 274 | 72 | 42 |
| 163 | 0.17 | 103 | 48 | 299 | 70 | 23 |
| 168 | 2.16 | 53 | 58 | 52 | 77 | 19 |
| 170 | 2.12 | 234 | 24 | 223 | 66 | 42 |
| 172 | 6.59 | 162 | 41 | 139 | 78 | 36 |
| 174 | 4.76 | 147 | 36 | 183 | 77 | 41 |
| 185 | 1.93 | 144 | 39 | 59 | 80 | 41 |
| 189 | 1.55 | 28 | 49 | 23 | 80 | 31 |
| 191 | 2.51 | 55 | 49 | 33 | 78 | 29 |
| 194 | 1.48 | 99 | 38 | 87 | 78 | 41 |
| 196 | 1.80 | 253 | 20 | 287 | 40 | 20 |
| 197 | 1.41 | 249 | 46 | 138 | 67 | 21 |
| 198 | 2.44 | 187 | 29 | 197 | 52 | 23 |
| 199 | 4.55 | 83 | 36 | 77 | 68 | 32 |
| 201 | 5.62 | 47 | 40 | 40 | 78 | 38 |

Another embodiment of the invention is a compound selected from Table 1 or a pharmaceutically acceptable salt thereof.

Furthermore, the compounds previously described in the patent literature that are the most closely structurally related to the compounds described in Table 1 do not possess the superior activity profile as described above. Data for these compounds is shown in Table 2. As can be seen from a direct comparison of the data, the compounds described in Table 1 possess an unexpectedly superior activity profile as compared to the compounds of Table 2.

TABLE 2

| Structure | GR BIND Ki (nM) | Transactiviation A549 Cells GRAMMER IP (nM) | Emax (%) | Transactiviation U937 Cells GITAR IP (nM) | Emax (%) | GITAR > GRAMM % SEP | |
|---|---|---|---|---|---|---|---|
| 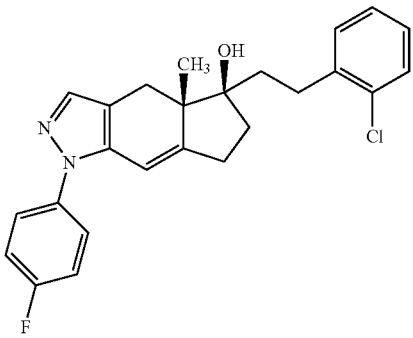 Chiral | 20.72 | 162 | 98 | 212 | 91 | −7 | Example 40 WO 2004/075840 A2 |
| 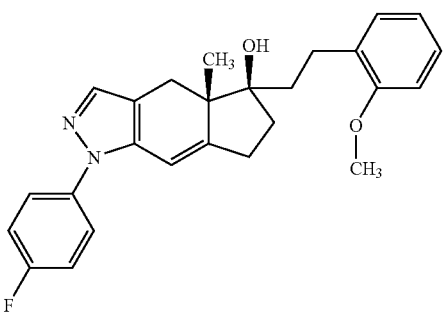 | 0.28 | 397 | 28 | 642 | 42 | 14 | Example 58 WO 2004/075840 A2 |

TABLE 2-continued
| Structure | GR BIND Ki (nM) | Transactiviation A549 Cells GRAMMER | | Transactiviation U937 Cells GITAR | | GITAR > GRAMM % SEP | |
|---|---|---|---|---|---|---|---|
| | | IP (nM) | Emax (%) | IP (nM) | Emax (%) | | |
| 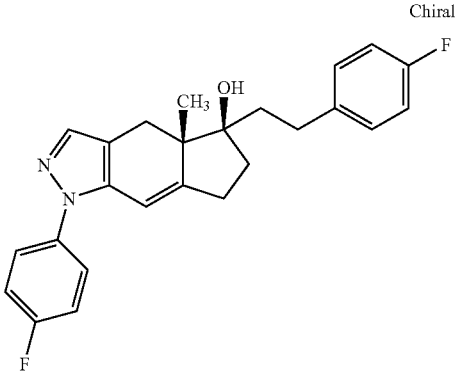 Chiral | 1.00 | 571 | 26 | 596 | 71 | 44 | Example 46 WO 2004/075840 A2 |
| 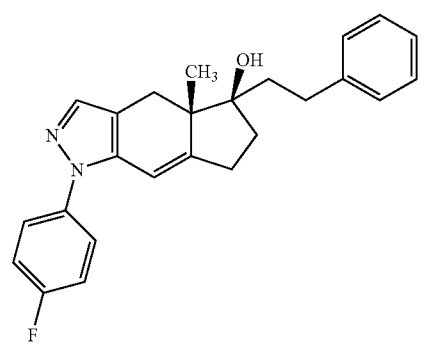 Chiral | 5.24 | 230 | 73 | 204 | 78 | 5 | Example 2 WO 2004/075840 A2 |
| 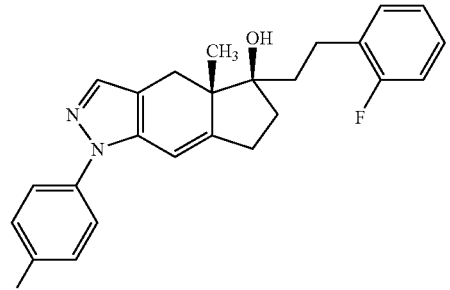 | 2.95 | 215 | 144 | 175 | 83 | −62 | Example 70 WO 2004/075840 A2 |
| 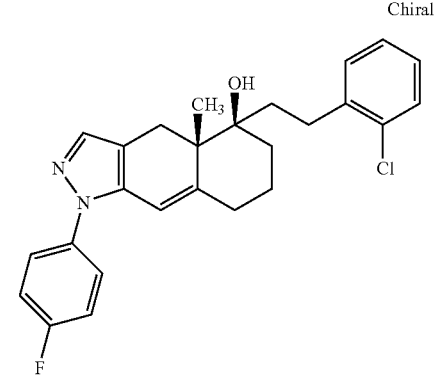 Chiral | 0.32 | 123 | 92 | 270 | 88 | −3 | Example 41 WO 2004/075840 A2 |

TABLE 2-continued

| Structure | GR BIND Ki (nM) | Transactiviation A549 Cells GRAMMER | | Transactiviation U937 Cells GITAR | | GITAR > GRAMM % SEP | |
|---|---|---|---|---|---|---|---|
| | | IP (nM) | Emax (%) | IP (nM) | Emax (%) | | |
| Chiral [structure] | 1.27 | 109 | 85 | 327 | 71 | −14 | Example 22 WO 03/086294 A2 |
| Chiral [structure] | 2.04 | 377 | 85 | 327 | 71 | −14 | Example 32 WO 03/086294 A2 |

Another embodiment of the invention encompasses a compound of Formula J

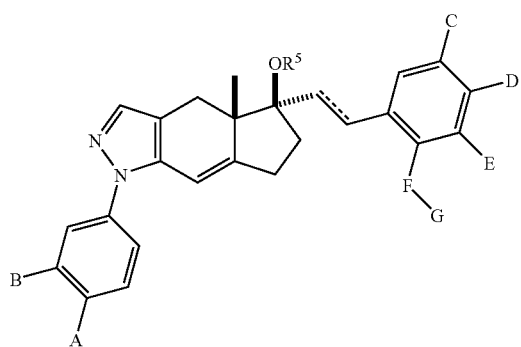

J or a pharmaceutically acceptable salt thereof, wherein
------ is an optional double bond;
A and B are independently selected from the group consisting of: H, F and Cl;
C, D and E are independently selected from the group consisting of: H, F, Cl, —CN, —CH$_3$, —OCH$_3$, phenyl and —CF$_3$;
F is selected from the group consisting of: a bond, —C(R$^1$)(R$^2$)— and —C(R$^1$)(R$^2$)—C(R$^3$)(R$^4$)—;
G is selected from the group consisting of: —CN, —OH, —O—C(O)—N(R)(R), —O—C(O)—O—R, —C(O)—R, —C(O)—O—R, —NRR, aryl, substituted aryl, heteroaryl, substituted heteroaryl, —C(R$^a$)(R$^b$)—N(R)(R), —C(O)—N(R)(R), —C(O)—N(R)—C(R$^a$)(R$^b$)—R, —C(O)—N(R)—C(R$^a$)(R$^b$)—C(O)—OR, —C(O)—N(R)—C(R$^a$)(R$^b$)—C(O)—NRR, —N(R)—C(O)—R, —N(R)—C(O)—OR, —N(R)—C(O)—N(R)(R), —N(R)—S(O)$_n$—X, —S(O)$_n$—N(R)(R), —N(R)—S(O)$_n$—N(R)(R) and —S(O)$_n$—X, wherein n is 0, 1 or 2;
each R is independently selected from the group consisting of: H, C$_{1-8}$alkyl, haloC$_{1-8}$alkyl, C$_{2-8}$alkenyl, haloC$_{2-8}$alkenyl, C$_{1-8}$alkoxy and C$_{3-6}$cycloalkyl-C$_{1-4}$alkyl-, and
two R groups attached to the same nitrogen atom can be joined together with the nitrogen atom to which they are attached to form a 3- to 7-membered monocyclic ring, said ring optionally substituted with oxo and said ring further optionally substituted with 1 to 3 substituents independently selected from the group consisting of: halo, hydroxyl, C$_{1-4}$alkyl and C$_{1-4}$alkoxy;
X is selected from the group consisting of: H, C$_{1-8}$alkyl, haloC$_{1-8}$alkyl, C$_{2-8}$alkenyl, haloC$_{2-8}$alkenyl, C$_{1-8}$alkoxy, C$_{3-6}$cycloalkyl, C$_{3-6}$cycloalkyl-C$_{1-4}$alkyl-, —CH$_2$—S(O)$_k$—CH$_3$, wherein k is 0, 1 or 2, aryl, substituted aryl, heteroaryl and substituted heteroaryl;

$R^1$, $R^2$, $R^3$ and $R^4$ are independently selected from the group consisting of: H, halo, $C_{1-4}$alkyl, hydroxy, $C_{3-6}$cycloalkyl and $C_{1-4}$haloalkyl, and $R^1$ and $R^2$ may be joined together with the carbon atom to which they are attached to form a 3- to 6-membered mono-cyclic ring;

$R^a$ and $R^b$ are independently selected from the group consisting of: H, $C_{1-4}$alkyl, $C_{1-4}$haloalkyl and hydroxy or $R^a$ and $R^b$ may be joined together with the carbon atom to which they are attached to form a 3- to 6-membered mono-cyclic ring;

substituted aryl and substituted heteroaryl mean aryl and heteroaryl respectively, each substituted with one to three substituents independently selected from the group consisting of: halo, $C_{1-4}$alkyl, $C_{1-4}$haloalkyl and —CN; and $R^5$ is H or —$CH_3$.

Within this embodiment, the invention encompasses a compound of Formula J wherein:
the optional double bond is not present;
F is selected from the group consisting of: a bond and —C($R^1$)($R^2$)—;
G is —C(O)—N(R)(R); and
$R^5$ is H.

The invention also encompasses a pharmaceutical composition comprising a compound of Formula J in combination with a pharmaceutically acceptable carrier.

The invention also encompasses a method for treating a glucocorticoid receptor mediated disease or condition in a mammalian patient in need of such treatment comprising administering the patient a compound of Formula J in an amount that is effective for treating the glucocorticoid receptor mediated disease or condition.

The invention also encompasses a compound selected from Examples 165 to 201 described above or a pharmaceutically acceptable salt of any of these compounds.

What is claimed is:
1. A compound of Formula I

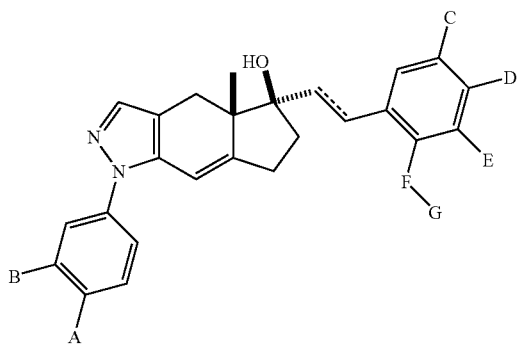

I or a pharmaceutically acceptable salt thereof, wherein
------ is an optional double bond;
A and B are independently selected from the group consisting of: H and F;
C, D and E are independently selected from the group consisting of: H, F, —$CH_3$ and —$CF_3$;
F is selected from the group consisting of: a bond, —C($R^1$)($R^2$)— and —C($R^1$)($R^2$)—C($R^3$)($R^4$)—;
G is selected from the group consisting of: —O—C(O)—N(R)(R), —O—C(O)—O—R, —C(O)—R, —C(O)—O—R, —C(O)—N(R)(R), —C(O)—N(R)—C($R^a$)($R^b$)—R, —C(O)—N(R)—C($R^a$)($R^b$)—C(O)—OR, —C(O)—N(R)—C($R^a$)($R^b$)—C(O)—NRR, —N(R)—C(O)—R, —N(R)—C(O)—OR, —N(R)—C(O)—N(R)(R), —N(R)—S(O)$_n$—X, —S(O)$_n$—N(R)(R), and —N(R)—S(O)$_n$—N(R)(R), wherein n is 0, 1 or 2;

each R is independently selected from the group consisting of: H, halo$C_{1-8}$alkyl, $C_{2-8}$alkenyl, halo$C_{2-8}$alkenyl, $C_{1-8}$alkoxy and $C_{3-6}$cycloalkyl-$C_{1-4}$alkyl-, and two R groups attached to the same nitrogen atom can be joined together with the nitrogen atom to which they are attached to form a 3- to 7-membered monocyclic ring, said ring optionally substituted with oxo and said ring further optionally substituted with 1 to 3 substituents independently selected from the group consisting of: halo, hydroxyl, $C_{1-4}$alkyl and $C_{1-4}$alkoxy;

X is selected from the group consisting of: H, $C_{1-8}$alkyl, halo$C_{1-8}$alkyl, $C_{2-8}$alkenyl, halo$C_{2-8}$alkenyl, $C_{1-8}$alkoxy, $C_{3-6}$cycloalkyl, $C_{3-6}$cycloalkyl-$C_{1-4}$alkyl-, —$CH_2$—S(O)$_k$—$CH_3$, wherein k is 0, 1 or 2, aryl, substituted aryl, heteroaryl and substituted heteroaryl;

$R^1$, $R^2$, $R^3$ and $R^4$ are independently selected from the group consisting of: H, $C_{1-4}$alkyl, $C_{1-4}$haloalkyl and hydroxy, and $R^1$ and $R^2$ may be joined together with the carbon atom to which they are attached to form a 3- to 6-membered mono-cyclic ring;

$R^a$ and $R^b$ are independently selected from the group consisting of: H, $C_{1-4}$alkyl, $C_{1-4}$haloalkyl and hydroxy or $R^a$ and $R^b$ may be joined together with the carbon atom to which they are attached to form a 3- to 6-membered mono-cyclic ring; and substituted aryl and substituted heteroaryl mean aryl and heteroaryl respectively, each substituted with one to three substituents independently selected from the group consisting of: halo, $C_{1-4}$alkyl, $C_{1-4}$haloalkyl and —CN.

2. The compound according to claim 1 wherein F is a bond and the optional double bond is not present.

3. The compound according to claim 2 wherein G is selected from the group consisting of: —C(O)—N(R)(R), —C(O)—N(R)—C($R^a$)($R^b$)—R, —C(O)—N(R)—C($R^a$)($R^b$)—C(O)—OR and —C(O)—N(R)—C($R^a$)($R^b$)—C(O)—NRR.

4. The compound according to claim 2 wherein G is —S(O)$_n$—N(R)(R).

5. The compound according to claim 1 wherein F is —C($R^1$)($R^2$)— and the optional double bond is not present.

6. The compound according to claim 5 wherein $R^1$ and $R^2$ are H.

7. The compound according to claim 6 wherein G is —N(R)—S(O)$_n$—X.

8. The compound according to claim 6 wherein G is —C(O)—N(R)(R).

9. The compound according to claim 1 wherein A is F.

10. A compound according to claim 1 selected from the following group:
(1) (4αS,5R)-5-(2-{2-[(3,3-diethoxyazetidin-1-yl)carbonyl]phenyl}ethyl)-1-(4-fluorophenyl)-4α-methyl-1,4,4α,5,6,7-hexahydrocyclopenta[f]indazol-5-ol;
(2) N-(2,2-dimethylpropyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(3) methyl 1-[(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)amino]cyclopropanecarboxylate;
(4) N-ethyl-2-{2-[(4αS,5R)-5-hydroxy-4α-methyl-1-phenyl-1,4,4α,5,6,7-hexahydrocyclopenta[f]indazol-5-yl]ethyl}benzamide;

(5) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(1-methylcyclopropyl)benzamide;

(6) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-isobutylbenzamide;

(7) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-propylbenzamide;

(8) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(3,3,3-trifluoro-2-methylpropyl)benzamide;

(9) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-methylprop-2-en-1-yl)benzamide;

(10) N-allyl-2-{2-[(4αS,5R)-1-(4-fluorophenyl)-5-hydroxy-4α-methyl-1,4,4α,5,6,7-hexahydrocyclopentaindazol-5-yl]ethyl}benzamide;

(11) 2-{2-[(4αS,5R)-5-hydroxy-4α-methyl-1-phenyl-1,4,4α,5,6,7-hexahydrocyclopenta[f]indazol-5-yl]ethyl}-N-(1-methylcyclopropyl)benzamide;

(12) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-isopropylbenzamide;

(13) N-ethyl-2-{2-[(4αS,5R)-1-(3-fluorophenyl)-5-hydroxy-4α-methyl-1,4,4α,5,6,7-hexahydrocyclopenta[f]indazol-5-yl]ethyl}benzamide;

(14) N-(cyclopropylmethyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(15) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(3,3,3-trifluoro-2-methylpropyl)benzamide;

(16) 2-{2-[(4αS,5R)-1-(3,4-difluorophenyl)-5-hydroxy-4α-methyl-1,4,4α,5,6,7-hexahydrocyclopenta[f]indazol-5-yl]ethyl}-N-(1-methylcyclopropyl)benzamide;

(17) (4αS,5R)-5-{2-[2-(azetidin-1-ylcarbonyl)phenyl]ethyl}-1-(4-fluorophenyl)-4α-methyl-1,4,4α,5,6,7-hexahydrocyclopenta[f]indazol-5-ol;

(18) methyl N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-2-methylalaninate;

(19) N-cyclopropyl-2-{2-[(4αS,5R)-5-hydroxy-4α-methyl-1-phenyl-1,4,4α,5,6,7-hexahydrocyclopenta[f]indazol-5-yl]ethyl}benzamide;

(20) N-ethyl-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(21) 2-{2-[(4αS,5R)-5-hydroxy-4α-methyl-1-phenyl-1,4,4α,5,6,7-hexahydrocyclopenta[f]indazol-5-yl]ethyl}benzamide;

(22) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-methylprop-2-en-1-yl)benzamide;

(23) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-[(2R)-3,3,3-trifluoro-2-methylpropyl]benzamide;

(24) (4αS,5R)-1-(4-fluorophenyl)-4α-methyl-5-{2-[2-(piperidin-1-ylcarbonyl)phenyl]ethyl}-1,4,4α,5,6,7-hexahydrocyclopenta[f]indazol-5-ol;

(25) (4αS,5R)-1-(4-fluorophenyl)-4α-methyl-5-{2-[2-(pyrrolidin-1-ylcarbonyl)phenyl]ethyl}-1,4,4α,5,6,7-hexahydrocyclopenta[f]indazol-5-ol;

(26) N-[(1R)-1,2-dimethylpropyl]-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(27) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-propylbenzamide;

(28) N-allyl-2-{2-[(4αS,5R)-1-(4-fluorophenyl)-5-hydroxy-4α-methyl-1,4,4α,5,6,7-hexahydrocyclopenta[f]indazol-5-yl]ethyl}-N-methylbenzamide;

(29) 2-{2-[(4αS,5R)-1-(3,4-difluorophenyl)-5-hydroxy-4α-methyl-1,4,4α,5,6,7-hexahydrocyclopenta[f]indazol-5-yl]ethyl}-N-ethylbenzamide;

(30) methyl N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-2-methylalaninate;

(31) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2-fluoroprop-2-en-1-yl)benzamide;

(32) (4αS,5R)-1-(4-fluorophenyl)-5-[2-(2-{[(3S)-3-fluoropyrrolidin-1-yl]carbonyl}phenyl)ethyl]-4α-methyl-1,4,4α,5,6,7-hexahydrocyclopenta[f]indazol-5-ol;

(33) N-(2,2-dimethylpropyl)-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(34) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-(2,2,2-trifluoroethyl)acetamide;

(35) N-allyl-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(36) (4αS,5R)-1-(4-fluorophenyl)-5-[2-(2-{[(3R)-3-hydroxypyrrolidin-1-yl]carbonyl}phenyl)ethyl]-4α-methyl-1,4,4α,5,6,7-hexahydrocyclopenta[f]indazol-5-ol;

(37) N-(tert-butyl)-2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(38) 2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(39) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-isobutylbenzamide;

(40) N-(tert-butyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(41) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-(1-methylcyclopropyl)benzamide;

(42) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-(2,2,2-trifluoroethyl)benzamide;

(43) (4αS,5R)-5-{2-[2-(azetidin-1-ylcarbonyl)-3-fluorophenyl]ethyl}-1-(4-fluorophenyl)-4α-methyl-1,4,4α,5,6,7-hexahydrocyclopenta[f]indazol-5-ol;

(44) (4αS,5R)-5-(2-{2-[(3,3-difluoropiperidin-1-yl)carbonyl]phenyl}ethyl)-1-(4-fluorophenyl)-4α-methyl-1,4,4α,5,6,7-hexahydrocyclopenta[f]indazol-5-ol;

(45) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}-N-isopropylbenzamide;

(46) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(47) (4αS,5R)-5-[2-(3-fluoro-2-{[(3S)-3-fluoropyrrolidin-1-yl]carbonyl}phenyl)ethyl]-1-(4-fluorophenyl)-4α-methyl-1,4,4α,5,6,7-hexahydrocyclopenta[f]indazol-5-ol;
(48) N-(2-amino-1,1-dimethyl-2-oxoethyl)-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(49) N-[2-(ethylamino)-1,1-dimethyl-2-oxoethyl]-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(50) methyl N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)-D-alaninate;
(51) (4αS,5R)-1-(4-fluorophenyl)-4α-methyl-5-(2-{2-[(2-methylaziridin-1-yl)carbonyl]phenyl}ethyl)-1,4,4α,5,6,7-hexahydrocyclopenta[f]indazol-5-ol;
(52) (4αS,5R)-5-(2-{2-[(3,3-difluoropyrrolidin-1-yl)carbonyl]phenyl}ethyl)-1-(4-fluorophenyl)-4α-methyl-1,4,4α,5,6,7-hexahydrocyclopenta[f]indazol-5-ol;
(53) N-[1,1-dimethyl-2-(methylamino)-2-oxoethyl]-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(54) (4αS,5R)-5-(2-{2-[(3,3-difluoropiperidin-1-yl)carbonyl]-3-fluorophenyl}ethyl)-1-(4-fluorophenyl)-4α-methyl-1,4,4α,5,6,7-hexahydrocyclopenta[f]indazol-5-ol;
(55) (4αS,5R)-5-(2-{2-[(3,3-difluoropyrrolidin-1-yl)carbonyl]-3-fluorophenyl}ethyl)-1-(4-fluorophenyl)-4α-methyl-1,4,4α,5,6,7-hexahydrocyclopenta[f]indazol-5-ol;
(56) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide;
(57) 2,4-difluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide;
(58) 2-fluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide;
(59) 3-cyano-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide;
(60) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)pyridine-3-sulfonamide;
(61) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)propane-2-sulfonamide;
(62) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide;
(63) 1,1-dichloro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide;
(64) N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)cyclopropanesulfonamide;
(65) 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide;
(66) N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide;
(67) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)cyclopropanesulfonamide;
(68) N'-(2-fluoro-6-{2-[(4αS,5R)-1-(4-fluorophenyl)-5-hydroxy-4α-methyl-1,4,4α,5,6,7-hexahydrocyclopenta indazol-5-yl]ethyl}benzyl)-N,N-dimethylsulfamide;
(69) 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)ethanesulfonamide;
(70) N-[1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropyl]cyclopropane sulfonamide;
(71) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)furan-2-sulfonamide;
(72) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)-1-methyl-1H-imidazole-4-sulfonamide;
(73) 2-cyano-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)benzenesulfonamide;
(74) N-[(1S)-1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]cyclopropanesulfonamide;
(75) 2,2,2-trifluoro-N-[(1R)-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide;
(76) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)-1-(methylsulfonyl)methanesulfonamide;
(77) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzyl)methanesulfonamide;
(78) 2,2,2-trifluoro-N-[(1S)-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide;
(79) N-[1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropyl]cyclopropanesulfonamide;
(80) 2,2,2-trifluoro-N-[(1R)-2,2,2-trifluoro-1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]ethanesulfonamide;
(81) 2,2,2-trifluoro-N-[1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropyl]ethanesulfonamide;
(84) N-(2-{2-[(4αS,5R)-1-(4-fluorophenyl)-5-hydroxy-4α-methyl-1,4,4α,5,6,7-hexahydrocyclopenta[f]indazol-5-yl]ethyl}benzyl)acetamide;

(85) N-ethyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(86) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(87) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-methylacetamide;

(88) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylacetamide;

(89) N-cyclopropyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(94) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylsulfamide;

(95) N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide;

(96) N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)cyclopropanesulfonamide;

(97) N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)methanesulfonamide;

(98) 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide;

(99) N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N,N-dimethylsulfamide;

(100) 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide;

(101) 2,2,2-trifluoro-N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethanesulfonamide;

(103) methyl(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(104) ethyl(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(105) ethyl(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(106) methyl(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(107) methyl(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(108) ethyl(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)carbamate;

(109) N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(110) 2,2,2-trifluoro-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(111) 2,2,2-trifluoro-N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(112) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;

(113) N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-isopropylurea;

(114) N-ethyl-N-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea;

(115) N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-isopropylurea;

(116) N-ethyl-N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea;

(117) N-ethyl-N-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)urea;

(118) N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N'-isopropylurea;

(119) N-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-N-isopropylurea;

(120) 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl methyl carbonate;

(121) 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl ethylcarbamate;

(122) 2-{2-[(4αS,5R)-1-(4-fluorophenyl)-5-hydroxy-4α-methyl-1,4,4α,5,6,7-hexahydrocyclopenta[f]indazol-5-yl]ethyl}phenyl isopropylcarbamate;

(123) N-ethyl-2-{2-[(4αS,5R)-1-(4-fluorophenyl)-5-hydroxy-4α-methyl-1,4,4α,5,6,7-hexahydrocyclopenta[f]indazol-5-yl]ethyl}benzenesulfonamide;

(124) 2-{2-[(4αS,5R)-1-(4-fluorophenyl)-5-hydroxy-4α-methyl-1,4,4α,5,6,7-hexahydrocyclopenta[f]indazol-5-yl]ethyl}-N,N-dimethylbenzenesulfonamide;

(125) 2-{2-[(4αS,5R)-1-(4-fluorophenyl)-5-hydroxy-4α-methyl-1,4,4α,5,6,7-hexahydrocyclopenta[f]indazol-5-yl]ethyl}-N-methylbenzenesulfonamide;

(126) 2-{2-[(4αS,5R)-1-(3-fluorophenyl)-5-hydroxy-4α-methyl-1,4,4α,5,6,7-hexahydrocyclopenta[f]indazol-5-yl]ethyl}benzenesulfonamide;

(127) 2-{2-[(4αS,5R)-5-hydroxy-4α-methyl-1-phenyl-1,4,4α,5,6,7-hexahydrocyclopenta[f]indazol-5-yl]ethyl}benzenesulfonamide;

(128) 2-{2-[(4αS,5R)-1-(4-fluorophenyl)-5-hydroxy-4α-methyl-1,4,4α,5,6,7-hexahydrocyclopenta[f]indazol-5-yl]ethyl}benzenesulfonamide;

(129) 2-{2-[(4αS,5R)-1-(3,4-difluorophenyl)-5-hydroxy-4α-methyl-1,4,4α,5,6,7-hexahydrocyclopenta[f]indazol-5-yl]ethyl}benzenesulfonamide;

(133) 2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile;

(134) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile;

(135) 4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile;

(140) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxypropanamide;

(144) 2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzaldehyde;

(145) 2-{2-[(4αS,5R)-1-(4-Fluorophenyl)-5-hydroxy-4α-methyl-1,4,4α,5,6,7-hexahydrocyclopenta[f]indazol-5-yl]ethyl}benzoic acid;

(146) N-Ethyl-n'-(2-(2-[(4αS,5R)-1-(4-fluorophenyl)-5-hydroxy-4α-methyl-1,4,4α,5,6,7-hexahydrocyclopenta[f]indazol-5-yl]ethyl)benzyl urea;

(147) N-(2-(2-[(4αS,5R)-1-(4-fluorophenyl)-5-hydroxy-4α-methyl-1,4,4α,5,6,7-hexahydrocyclopenta(f)indazol-5-yl]ethyl)benzyl cyclopropanecarboxamide;

(148) Ethyl(2-(2-[(4αS,5R)-1-(4-fluorophenyl)-5-hydroxy-4α-methyl-1,4,4α,5,6,7-hexahydrocyclopenta[f]indazol-5-yl]ethyl)benzyl carbamate;

(149) N-[1-(2-{2-[(4αS,5R)-1-(4-Fluorophenyl)-5-hydroxy-4α-methyl-1,4,4α,5,6,7-hexahydrocyclopenta[f]indazol-5-yl]ethyl}phenyl)cyclopropyl]cyclopropanesulfonamide;

(150) N-[(1R)-1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)ethyl]cyclopropanesulfonamide;

(151) 2-(2-[(4αS,5R)-1-(4-fluorophenyl)-5-hydroxy-4α-methyl-1,4,4α,5,6,7-hexahydrocyclopenta[f]indazol-5-yl]ethyl)benzyl)ethylcarbamate;

(153) Ethyl-2-(2-[(4αS,5R)-1-(4-fluorophenyl)-5-hydroxy-4α-methyl-1,4,4α,5,6,7-hexahydrocyclopenta[f]indazol-5-yl]ethyl)phenylcarbonate;

(154) 2-(2-[(4αS,5R)-1-(4-fluorophenyl)-5-hydroxy-4α-methyl-1,4,4α,5,6,7-hexahydrocyclopenta[f]indazol-5-yl]ethyl)benzaldehyde;

(155) 1-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)azetidin-3-one;

(156) 1-(2-{2-[(4αS,5R)-1-(4-fluorophenyl)-5-hydroxy-4α-methyl-1,4,4α,5,6,7-hexahydrocyclopenta[f]indazol-5-yl]ethyl}benzoyl)azetidin-3-one;

(157) 1-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetone;

(159) 5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(160) 2-{(E)-2-[(4αS,5R)-1-(4-fluorophenyl)-5-hydroxy-4α-methyl-1,4,4α,5,6,7-hexahydrocyclopenta[f]indazol-5-yl]vinyl}benzenesulfonamide;

(161) 2-{2-[(4αS,5R)-1-(4-fluorophenyl)-5-hydroxy-4α-methyl-1,4,4α,5,6,7-hexahydrocyclopenta[f]indazol-5-yl]ethyl}-4-(trifluoromethyl)benzonitrile;

(162) 2-{2-[(4αS,5R)-1-(4-fluorophenyl)-5-hydroxy-4α-methyl-1,4,4α,5,6,7-hexahydrocyclopenta[f]indazol-5-yl]ethyl}-4-methylbenzonitrile;

(163) 5-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzonitrile; and (164) 2-{2-[(4αS,5R)-1-(4-fluorophenyl)-5-hydroxy-4α-methyl-1,4,4α,5,6,7-hexahydrocyclopenta[f]indazol-5-yl]ethyl}-5-(trifluoromethyl)benzonitrile;

or a pharmaceutically acceptable salt of any of the above compounds.

11. A pharmaceutical composition comprising a compound according to claim 1 in combination with a pharmaceutically acceptable carrier.

12. A method for treating a glucocorticoid receptor mediated disease or condition in a mammalian patient in need of such treatment comprising administering the patient a compound according to claim 1 in an amount that is effective for treating the glucocorticoid receptor mediated disease or condition; wherein the glucocorticoid receptor mediated disease or condition is rheumatoid arthritis.

13. A method of selectively modulating the activation, repression, agonism and antagonism effects of the glucocorticoid receptor in a mammal comprising administering to the mammal a compound according to claim 1 in an amount that is effective to modulate the glucocorticoid receptor.

14. A method of partially or fully antagonizing, repressing agonizing or modulating the glucocorticoid receptor in a mammal comprising administering to the mammal an effective amount of compound according to claim 1.

15. A compound according to claim 1 selected from the following group:

(1) 2-{2-[(4αS,5R)-1-(4-fluorophenyl)-5-methoxy-4α-methyl-1,4,4α,5,6,7-hexahydrocyclopenta[f]indazol-5-yl]ethyl}benzamide;

(2) 4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(3) 2-fluoro-6-{2-[(4αS,5R)-5-hydroxy-4α-methyl-1-phenyl-1,4,4α,5,6,7-hexahydrocyclopenta[f]indazol-5-yl]ethyl}benzamide;

(4) 2-{2-[(4αS,5R)-1-(3,4-difluorophenyl)-5-hydroxy-4α-methyl-1,4,4α,5,6,7-hexahydrocyclopenta[f]indazol-5-yl]ethyl}-6-fluorobenzamide;

(5) 2-chloro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(6) 5-chloro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(7) 4-chloro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(8) 2-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide;

(9) 2-{2-[(4αS,5R)-1-(4-fluorophenyl)-5-hydroxy-4α-methyl-1,4,4α,5,6,7-hexahydrocyclopenta[f]indazol-5-yl]ethyl}-4-(trifluoromethyl)benzamide;

(10) 2-{2-[(4αS,5R)-1-(4-fluorophenyl)-5-hydroxy-4α-methyl-1,4,4α,5,6,7-hexahydrocyclopenta[f]indazol-5-yl]ethyl}-4-methylbenzamide;

(11) 2-{2-[(4αS,5R)-1-(4-fluorophenyl)-5-hydroxy-4α-methyl-1,4,4α,5,6,7-hexahydrocyclopenta[f]indazol-5-yl]ethyl}-5-(trifluoromethyl)benzamide;

(12) 2-chloro-6-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide;

(13) 4-chloro-2-{2-[(4αS,5R)-1-(3,4-difluorophenyl)-5-hydroxy-4α-methyl-1,4,4α,5,6,7-hexahydrocyclopenta[f]indazol-5-yl]ethyl}benzamide;

(14) 4,5-difluoro-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(15) 2-{2-[(4αS,5R)-1-(4-fluorophenyl)-5-methoxy-4α-methyl-1,4,4α,5,6,7-hexahydrocyclopenta[f]indazol-5-yl]ethyl}-5-(trifluoromethyl)benzamide;

(16) 5-cyano-2-{2-[(4αS,5R)-1-(4-fluorophenyl)-5-hydroxy-4α-methyl-1,4,4α,5,6,7-hexahydrocyclopenta[f]indazol-5-yl]ethyl}benzamide;

(17) 2-{2-[(4αS,5R)-1-(4-fluorophenyl)-5-hydroxy-4α-methyl-1,4,4α,5,6,7-hexahydrocyclopenta[f]indazol-5-yl]ethyl}-5-methylbenzamide;
(18) 2-{2-[(4αS,5R)-1-(4-fluorophenyl)-5-hydroxy-4α-methyl-1,4,4α,5,6,7-hexahydrocyclopenta[f]indazol-5-yl]ethyl}-6-methylbenzamide;
(19) 2,3-difluoro-6-{2-[(4αS,5R)-1-(4-fluorophenyl)-5-hydroxy-4α-methyl-1,4,4α,5,6,7-hexahydrocyclopenta[f]indazol-5-yl]ethyl}benzamide;
(20) 2-{2-[(4αS,5R)-1-(4-chlorophenyl)-5-hydroxy-4α-methyl-1,4,4α,5,6,7-hexahydrocyclopenta[f]indazol-5-yl]ethyl}benzamide;
(21) 2-{2-[(4αS,5R)-1-(4-chlorophenyl)-5-hydroxy-4α-methyl-1,4,4α,5,6,7-hexahydrocyclopenta[f]indazol-5-yl]ethyl}-6-fluorobenzamide;
(22) 2-{2-[(4αS,5R)-1-(3,4-difluorophenyl)-5-hydroxy-4α-methyl-1,4,4α,5,6,7-hexahydrocyclopenta[f]indazol-5-yl]ethyl}-6-methylbenzamide;
(23) 2-{2-[(4αS,5R)-1-(3-fluorophenyl)-5-hydroxy-4α-methyl-1,4,4α,5,6,7-hexahydrocyclopenta[f]indazol-5-yl]ethyl}benzamide;
(24) 2-{2-[(4αS,5R)-1-(4-fluorophenyl)-5-hydroxy-4α-methyl-1,4,4α,5,6,7-hexahydrocyclopenta[f]indazol-5-yl]ethyl}-6-(trifluoromethyl)benzamide;
(25) 2-{2-[(4αS,5R)-1-(4-fluorophenyl)-5-hydroxy-4α-methyl-1,4,4α,5,6,7-hexahydrocyclopenta indazol-5-yl]ethyl}-6-methoxybenzamide;
(26) 4-{2-[(4αS,5R)-1-(4-fluorophenyl)-5-hydroxy-4α-methyl-1,4,4α,5,6,7-hexahydrocyclopenta[f]indazol-5-yl]ethyl}biphenyl-3-carboxamide;
(27) 2-{2-[(4αS,5R)-1-(3-fluorophenyl)-5-hydroxy-4α-methyl-1,4,4α,5,6,7-hexahydrocyclopenta[f]indazol-5-yl]ethyl}-6-methylbenzamide;
(28) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxyacetamide;
(29) 2-(4-fluoro-2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;
(30) 2-(2-fluoro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;
(31) 2-(2-{2-[(4αS,5R)-1-(3,4-difluorophenyl)-5-hydroxy-4α-methyl-1,4,4α,5,6,7-hexahydrocyclopenta[f]indazol-5-yl]ethyl}phenyl)acetamide;
(32) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)propanamide;
(33) 2-(2-chloro-6-{2-[(4αS,5R)-1-(4-fluorophenyl)-5-hydroxy-4α-methyl-1,4,4α,5,6,7-hexahydrocyclopenta[f]indazol-5-yl]ethyl}phenyl)acetamide;
(34) 2-fluoro-2-(2-{2-[(4αS,5R)-1-(4-fluorophenyl)-5-hydroxy-4α-methyl-1,4,4α,5,6,7-hexahydrocyclopenta indazol-5-yl]ethyl}phenyl)acetamide;
(35) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxybutanamide;
(36) 2-cyclopropyl-2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxyacetamide; and
(37) 2-(2-{2-[(4αS,5R)-1-(4-fluorophenyl)-5-hydroxy-4α-methyl-1,4,4α,5,6,7-hexahydrocyclopenta[f]indazol-5-yl]ethyl}phenyl)-2-hydroxy-3-methylbutanamide;
or a pharmaceutically acceptable salt of any of the above compounds.

16. A pharmaceutical composition comprising a compound according to claim 1 in combination with a pharmaceutically acceptable carrier.

17. A compound selected from the following group:

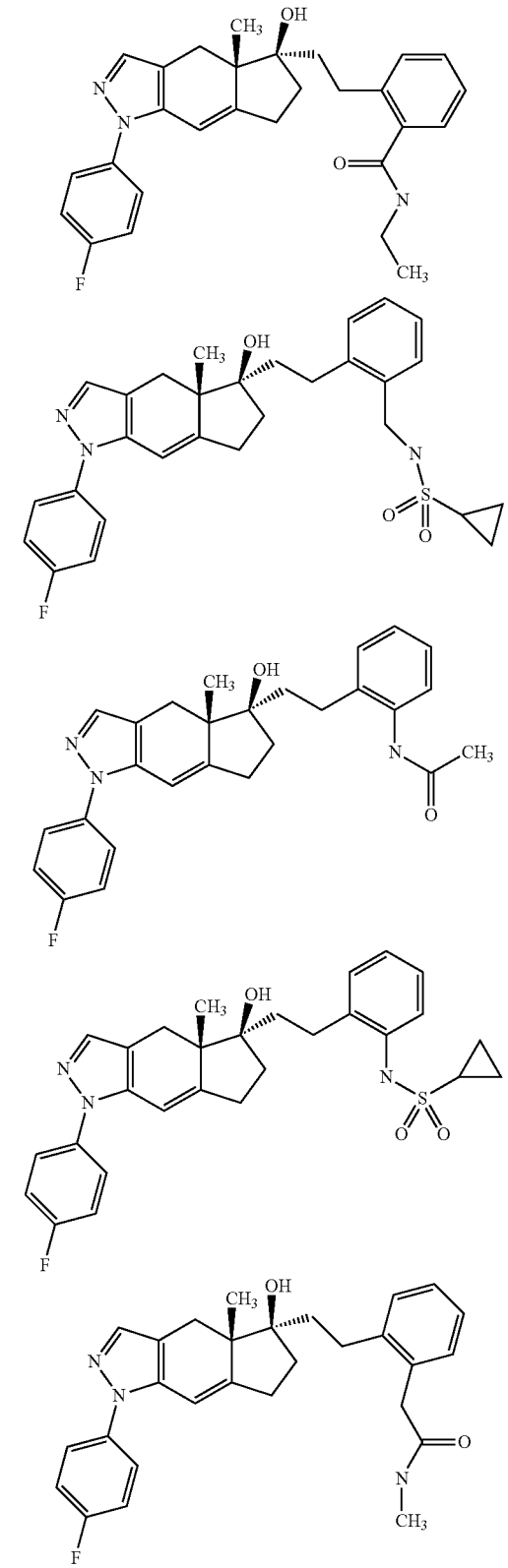

187
-continued
188
-continued
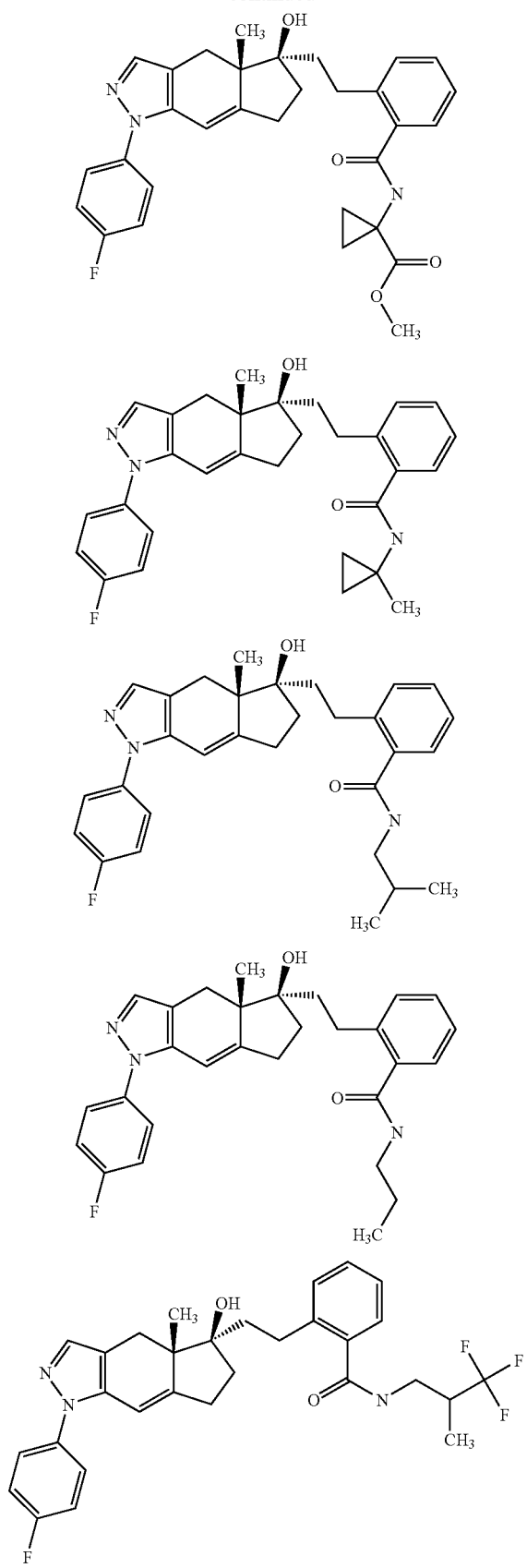
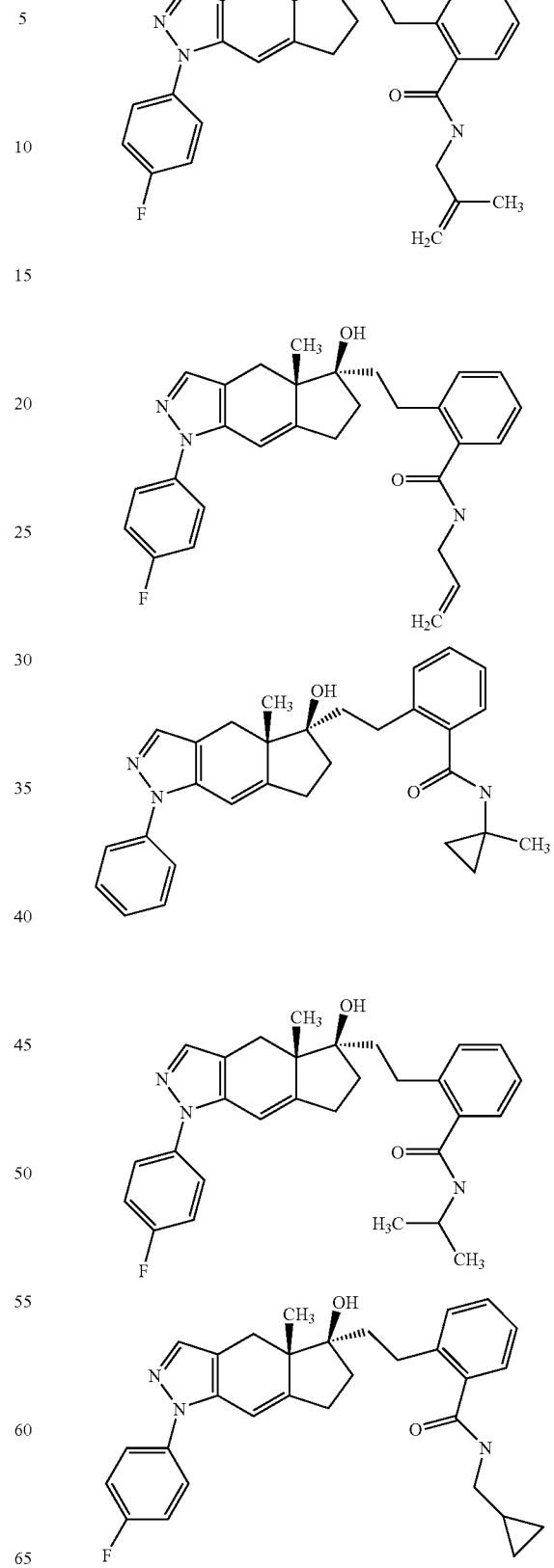

189
-continued
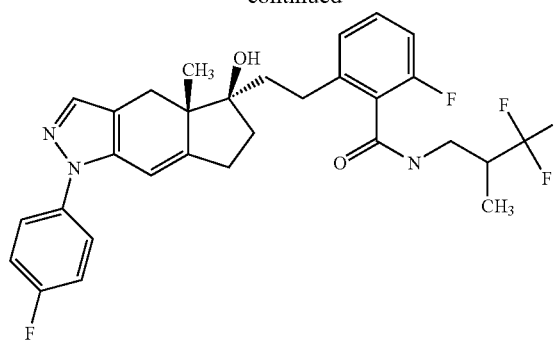
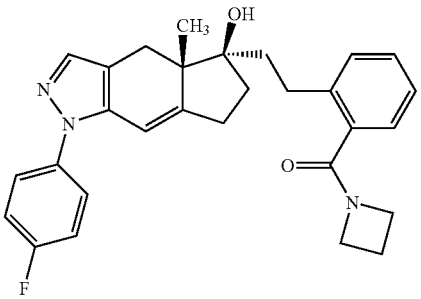
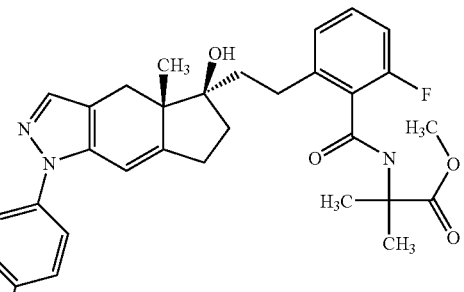
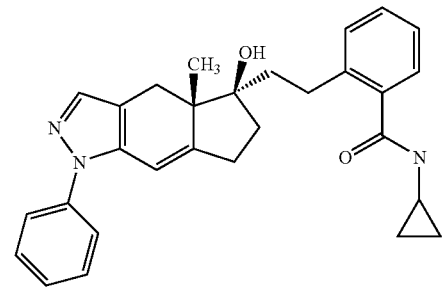
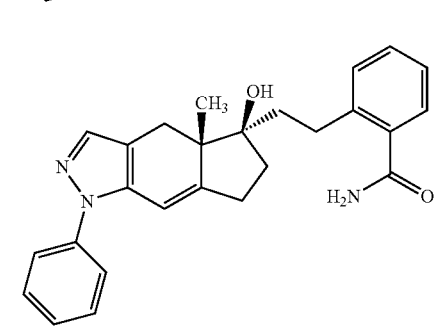
190
-continued
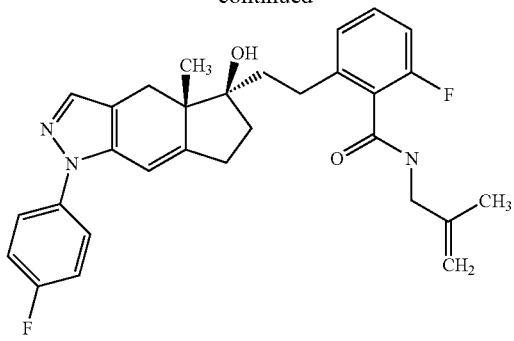
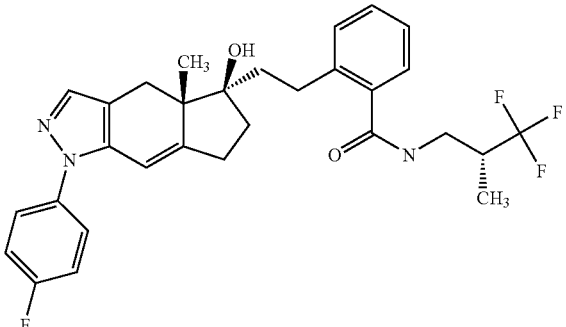
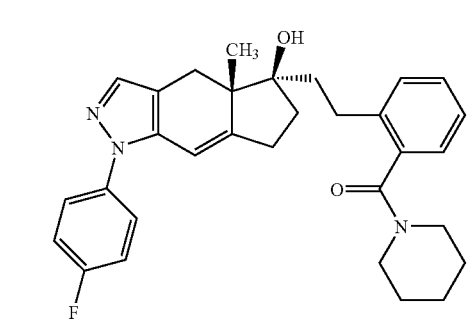
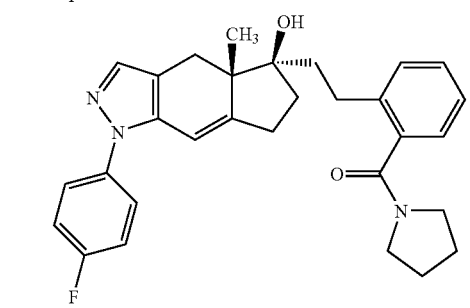
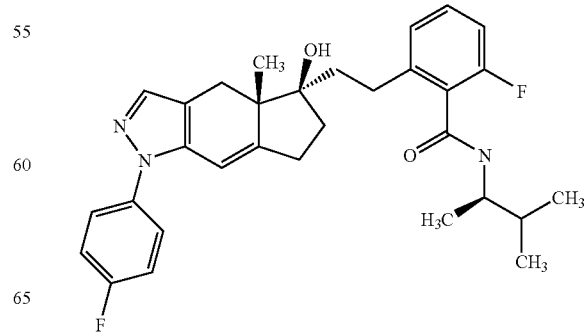

| 191 | 192 |
|---|---|
| 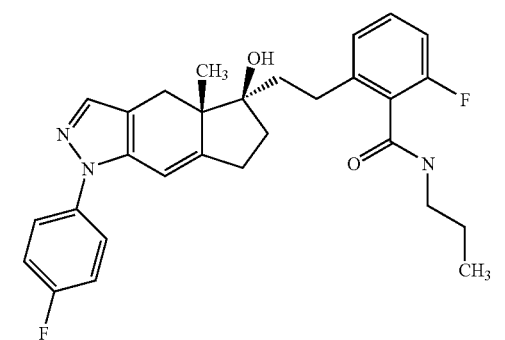 | 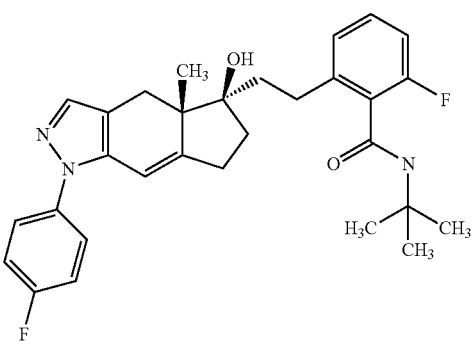 |
| 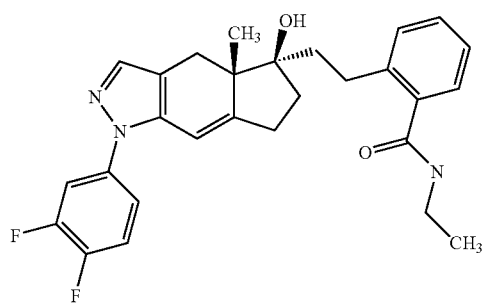 | 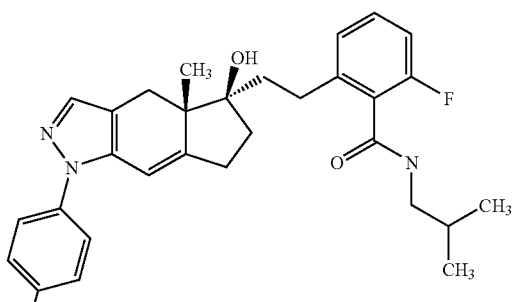 |
| 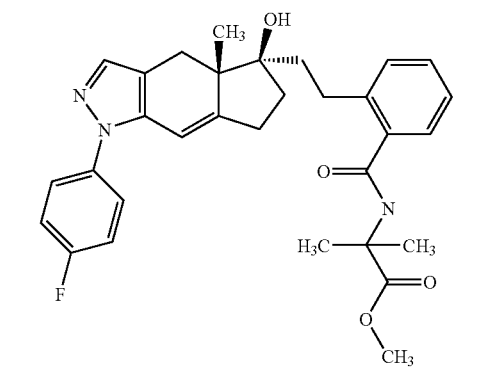 | 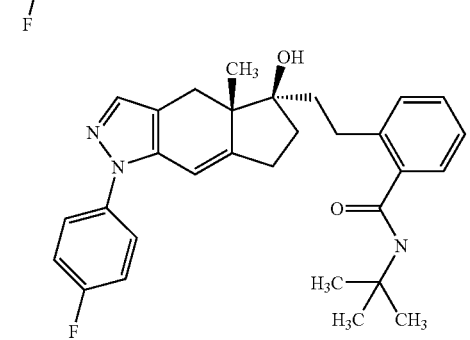 |
| 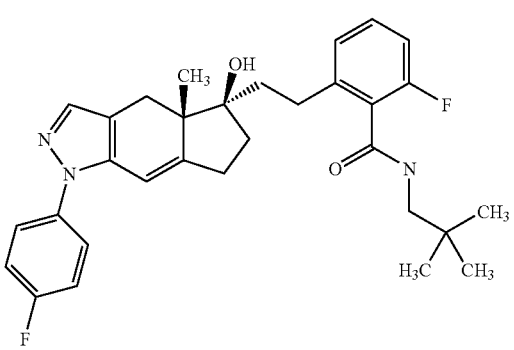 | 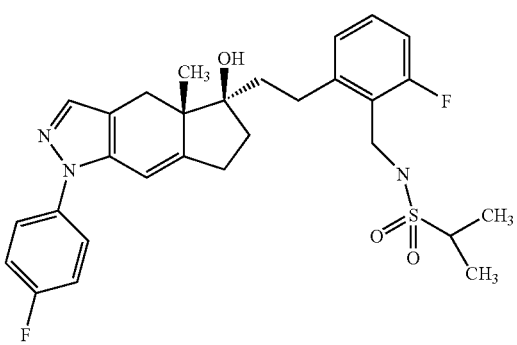 |
| 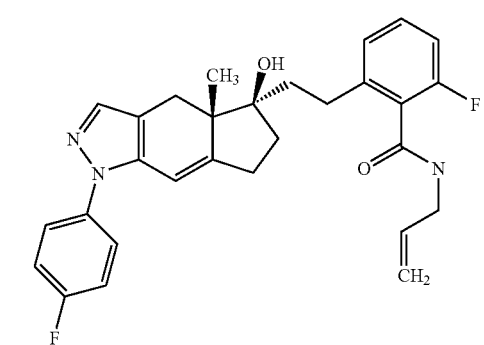 | 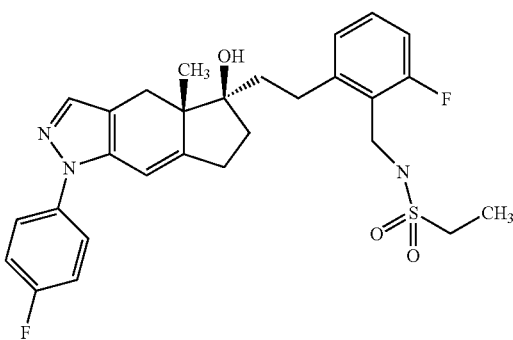 |

193
-continued
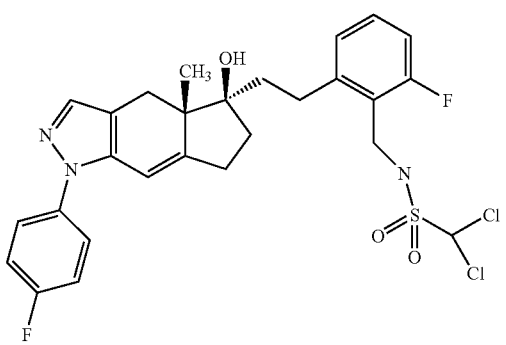
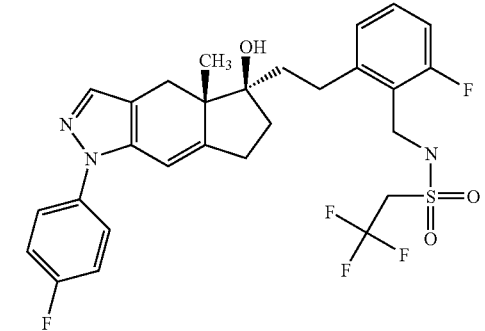
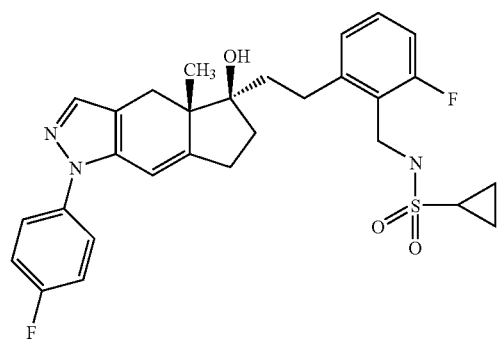
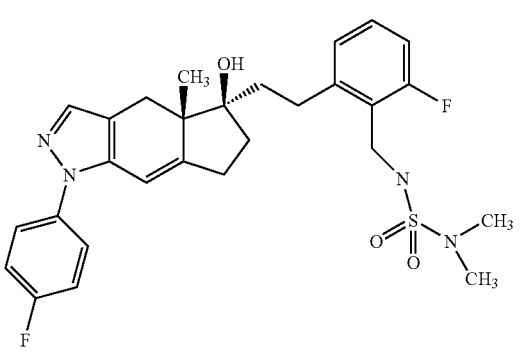
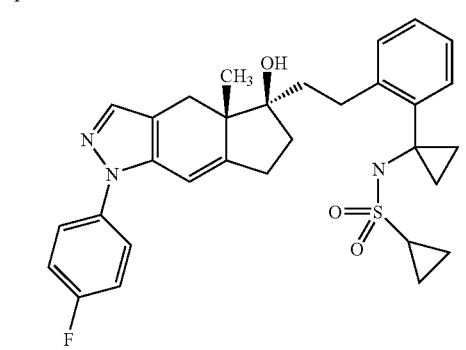
194
-continued
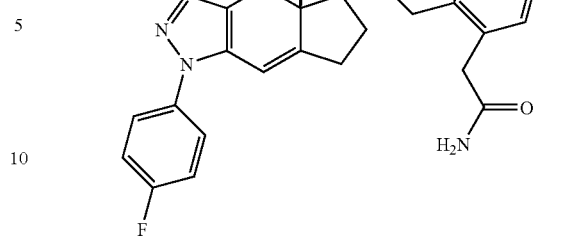
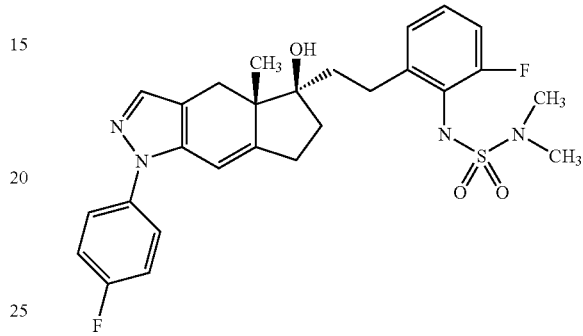
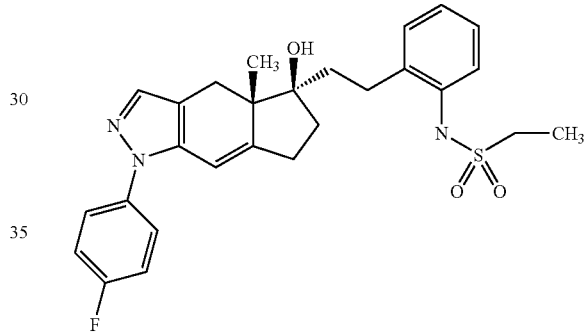
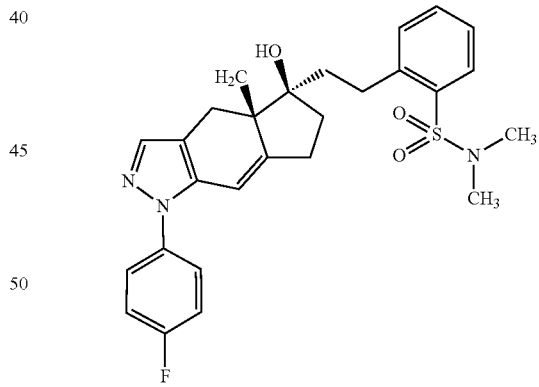
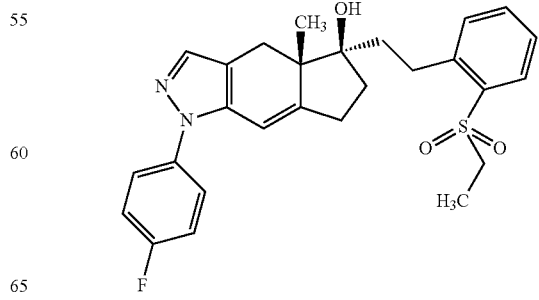

195
-continued
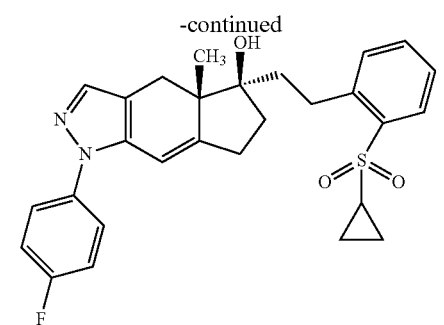
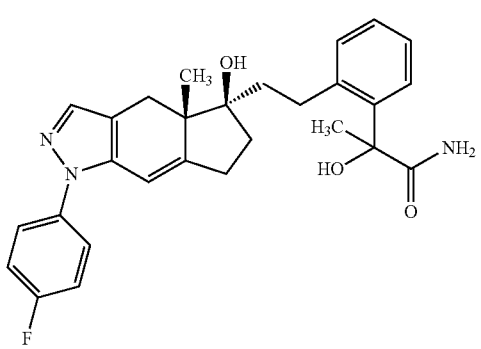
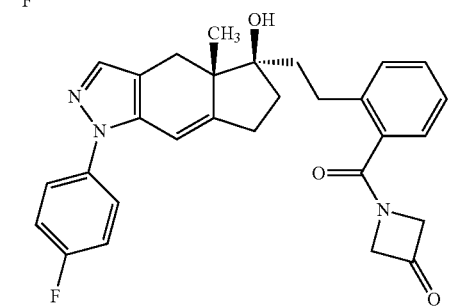
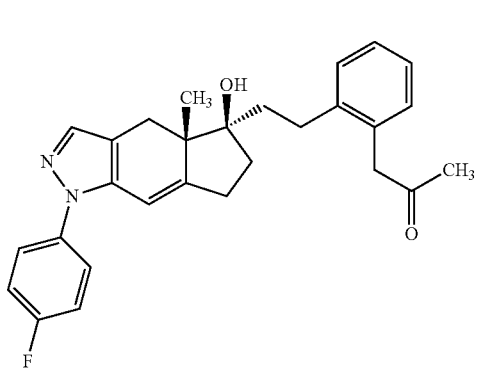
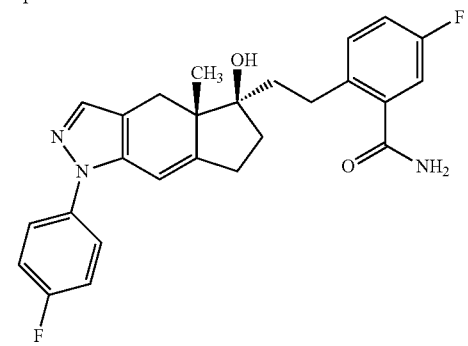
196
-continued
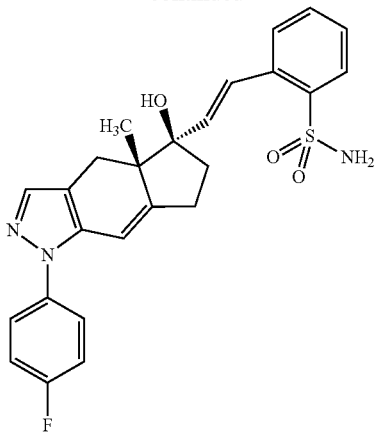
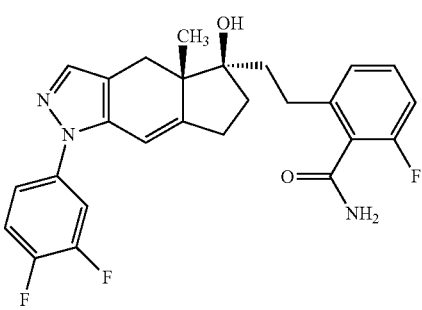
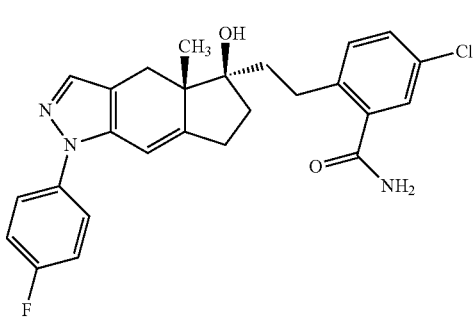
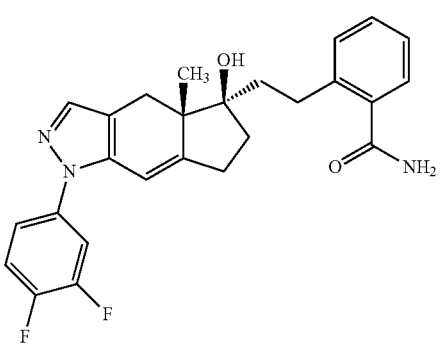

197
-continued
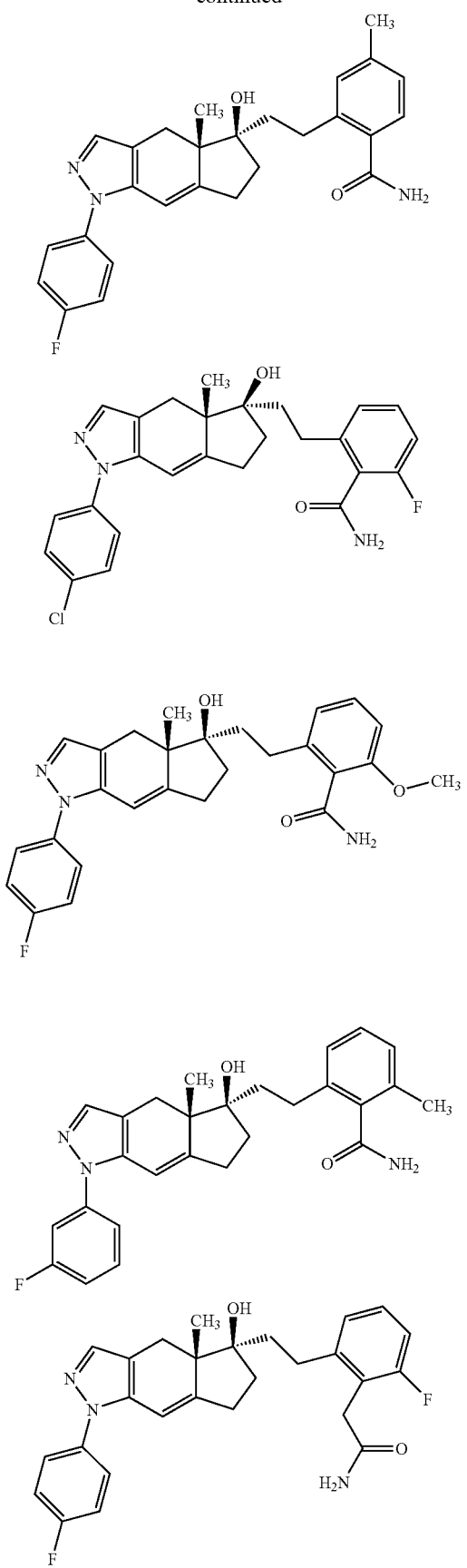
198
-continued
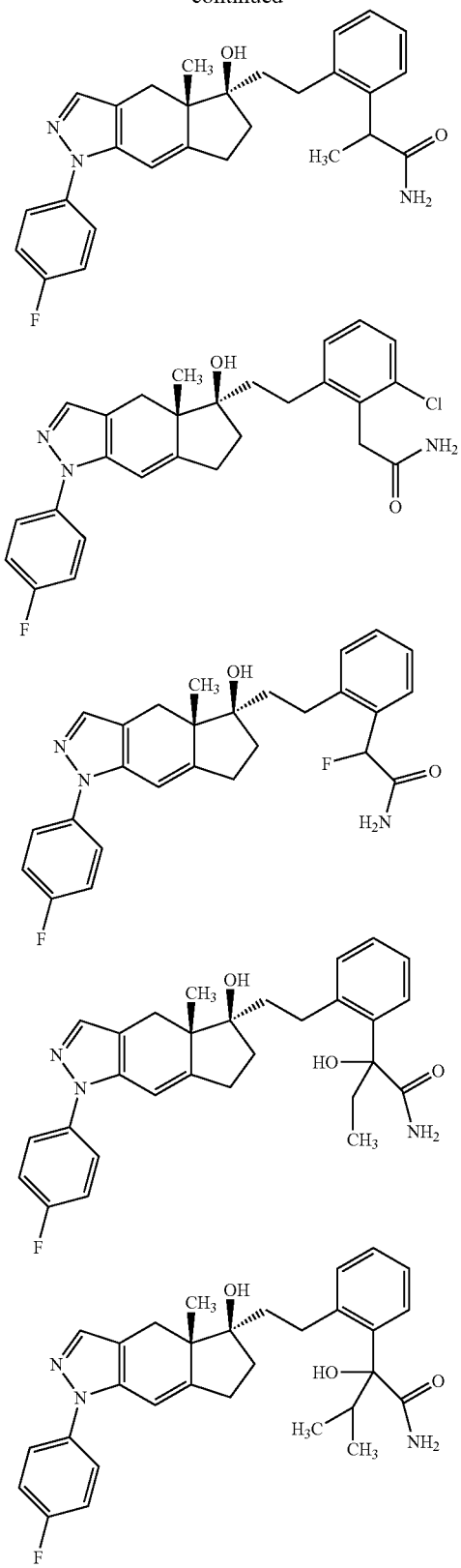
or a pharmaceutically acceptable salt of any of the foregoing compounds.
* * * * *